United States Patent
Buhrlage et al.

(10) Patent No.: US 11,136,291 B2
(45) Date of Patent: Oct. 5, 2021

(54) ANTIFUNGAL COMPOUNDS AND USES THEREOF

(71) Applicants: Dana-Farber Cancer Institute, Inc., Boston, MA (US); Centre Hospitalier Universitaire Vaudois, Lausanne (CH); The General Hospital Corporation, Boston, MA (US); President and Fellows of Harvard College, Cambridge, MA (US)

(72) Inventors: Sara Jean Buhrlage, Somerville, MA (US); Anders Näär, Arlington, MA (US); Gerhard Wagner, Brookline, MA (US); Haribabu Arthanari, Cambridge, MA (US); Joy Luz Nishikawa, Cambridge, MA (US); Andras Pal Boeszoermenyi, Boston, MA (US); Dominique Sanglard, Epalinges (CH)

(73) Assignees: Dana-Farber Cancer Institute, Inc., Boston, MA (US); Centre Hospitalier Universitaire Vaudois, Lausanne (CH); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 48 days.

(21) Appl. No.: 15/998,620

(22) PCT Filed: Feb. 17, 2017

(86) PCT No.: PCT/US2017/018433
§ 371 (c)(1),
(2) Date: Aug. 16, 2018

(87) PCT Pub. No.: WO2017/143230
PCT Pub. Date: Aug. 24, 2017

(65) Prior Publication Data
US 2020/0140381 A1 May 7, 2020
US 2021/0147351 A9 May 20, 2021

Related U.S. Application Data

(60) Provisional application No. 62/296,529, filed on Feb. 17, 2016.

(51) Int. Cl.
*C07C 335/40* (2006.01)
*A61P 31/10* (2006.01)

(52) U.S. Cl.
CPC ............ *C07C 335/40* (2013.01); *A61P 31/10* (2018.01)

(58) Field of Classification Search
None
See application file for complete search history.

(56) References Cited

U.S. PATENT DOCUMENTS 3,455,984 A    7/1969    Laliberte et al.

OTHER PUBLICATIONS

Moussa et al. "Some Thiosemicarbazide Derivatives as Corrosion Inhibitors for Aluminium in Sodium Hydroxide Solution" Bulletin of the Korean Chemical Society, 1988, vol. 9, No. 4, pp. 191-195.*
International Search Report and Written Opinon for PCT/US17/18433, dated Jul. 10, 2017.
Interarntional Preliminary Report on Patentability for PCT/US17/18433, dated Aug. 30, 2018.
[No Author Listed] PubChem-CID-12554290, Create Date: Feb. 8, 2007. p. 4.
[No Author Listed] PubChem-CID-2803556, Create Date: Jul. 19, 2005. p. 4.
[No Author Listed] PubChem-CID-2803611, Create Date: Jul. 19, 2005. p. 4.
Caudle et al., Genomewide expression profile analysis of the Candida glabrata Pdr1 regulon. Eukaryotic Cell Dec. 30, 2010;10(3):373-383.
Derisi et al., Genome microarray analysis of transcriptional activation in multidrug resistance yeast mutants. FEBS Lett. Mar. 24, 2000;470(2):156-60.
Fahmy et al., Synthesis and antimicrobial screening of some novel thiazoles, bisthiazoles, and thiazolylpyridines. Pharmazie 1997;52(10):750-753.
Fahmy et al., Synthesis of some new triazoles as potential antifungal agents. Bollettino Chimico Farmaceutico 2001;140(6):422-427.
Ferrari et al., Contribution of CgPDR1-Regulated Genes in Enhanced Virulence of Azole-Resistant Candida glabrata. PLoS ONE 2011;6(3):e17589. https://doi.org/10.1371/journal.pone.0017589.
Ferrari et al., Gain of Function Mutations in CgPDR1 of Candida glabrata Not Only Mediate Antifungal Resistance but Also Enhance Virulence. PLoS Pathog 2009;5(1): e1000268. https://doi.org/10.1371/journal.ppat.1000268.

(Continued)

*Primary Examiner* — Joseph R Kosack
(74) *Attorney, Agent, or Firm* — Wolf, Greenfield & Sacks, P.C.

(57) ABSTRACT

Provided herein are compounds (e.g., compounds of Formulae (I), (II), and (III)) which are anti-fungal agents and can be used in the treatment of diseases, including infectious diseases. The invention provides methods of treating diseases in a subject (e.g., infectious diseases such as fungal infections), and methods of killing or inhibiting the growth of fungi in or on a subject or biological sample. The compounds may be used in subjects, in clinical settings, or in agricultural settings.

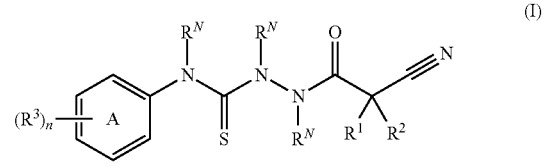

39 Claims, 37 Drawing Sheets

Specification includes a Sequence Listing.

(56) References Cited

OTHER PUBLICATIONS

Katzmann et al., Expression of an ATP-binding cassette transporter-encoding gene (YOR1) is required for oligomycin resistance in *Saccharomyces cerevisiae*. Mol Cell Biol. Dec. 1995;15(12):6875-83.

Kosikowska et al., Inhibitory effect of N-ethyl-3-amino-5-oxo-4-phenyl-2,5-dihydro-1H-pyrazole-1-carbothioamide on *Haemophilus* spp. *planktonic* or biofilm-forming cells. Med Chem Res. 2014;23:1057-1066. Epub Aug. 23, 2013.

Martin et al., the Candida albicans-Specific Gene EED1 Encodes a Key Regulator of Hyphal Extension. PLOS ONE 6(4): e18394. https://doi.org/10.1371/journal.pone.0018394.

Mohareb et al., Uses of 1-cyanoacetyl-4-phenyl-3-thiosemicarbazide in the synthesis of antimicrobial and antifungal heterocyclic compounds. International Research Journal of Pure and Applied Chemistry 2012;2(2):144-155.

Mohareb et al., Uses of 1-cyanoacetyl-4-phenyl-3-thiosemicarbazide in heterocyclic synthesis: Synthesis of thiazole, coumarin, and pyridine derivatives with antimicrobial and antifungal activities. Phosphorus, Sulfur and Silicon and the Related Elements 2007;182(8):1661-1681.

Paul et al., Multidrug resistance in fungi: regulation of transporter-encoding gene expression. Front. Physiol., Apr. 16, 2014 | https://doi.org/10.3389/fphys.2014.00143.

Pfaller et al., Candida bloodstream infections: comparison of species distribution and resistance to echinocandin and azole antifungal agents in Intensive Care Unit (ICU) and non-ICU settings in the SENTRY Antimicrobial Surveillance Program (2008-2009). Int J Antimicrob Agents. Jul. 2011;38(1):65-9. doi: 10.1016/j.ijantimicag. 2011.02.016. Epub Apr. 22, 2011.

Pfaller et al., Frequency of Decreased Susceptibility and Resistance to Echinocandins among Fluconazole-Resistant Bloodstream Isolates of Candida glabrata. J Clin Microbiol. Apr. 2012;50(4):1199-1203. doi: [10.1128/JCM.06112-11].

Pfaller et al., Variation in Susceptibility of Bloodstream Isolates of Candida glabrata to Fluconazole According to Patient Age and Geographic Location in the United States in 2001 to 2007. J. Clin. Microbiol. 2009;47:3185. DOI: 10.1128/JCM.00946-09.

Pitucha et al., Synthesis, structure, and antibacterial evaluation of new N-substituted-3-amino-5-oxo-4-phenyl-2,5-dihydro-1H-pyrazole-1-carbothioamides. Heteroatom Chemistry 2010;21(4):215-221.

Prasad et al., Yeast ATP-Binding Cassette Transporters Conferring Multidrug Resistance. Annual Review of Microbiology Oct. 2012;66:39-63. https://doi.org/10.1146/annurev-micro-092611-150111.

Sanglard et al., The ATP binding cassette transporter gene CgCDR1 from Candida glabrata is involved in the resistance of clinical isolates to azole antifungal agents. Antimicrobial Agents and Chemotherapy Nov. 1, 1999;43(11):2753-2765.

Sanguinetti et al., Mechanisms of azole resistance in clinical isolates of Candida glabrata collected during a hospital survey of antifungal resistance. Antimicrob Agents Chemother. Feb. 2005;49(2):668-79.

Simiti et al., Heterocydes. XXI. Synthesis of hydrazides of 2-arylamino-1,3,4-thiadiazole-5-acetic acids. Farmacia (Bucharest, Romania) 1971;19(9):543-52.

Thakur et al., A nuclear receptor-like pathway regulating multidrug resistance in fungi. Nature. Apr. 3, 2008;452(7187):604-9. doi: 10.1038/nature06836.

Vermitsky et al., Pdr1 regulates multidrug resistance in Candida glabrata: gene disruption and genome-wide expression studies. Mol Microbiol. Aug. 2006;61(3):704-22. Epub Jun. 27, 2006.

Wardakhan et al., New approaches for the synthesis of 1,3,4-thiadiazole and 1,2,4-triazole derivatives with antimicrobial activity. Phosphorus, Sulfur and Silicon and the Related Elements 2009;184(3):790-804.

Extended European Search Report for EP 17753951.7, dated Jul. 3, 2019.

\* cited by examiner

Extended Data Table 1 NMR and refinement statistics for CgGal11A KIX domain

| | Protein |
|---|---|
| NMR distance and dihedral constraints | |
| Distance constraints | |
|   Total NOE | 1718 |
|   Intra-residue | 602 |
|   Inter-residue | 1116 |
|     Sequential ($|i-j| = 1$) | 517 |
|     Medium-range ($|i-j| \leq 4$) | 488 |
|     Long-range ($|i-j| \geq 5$) | 111 |
|   Hydrogen bonds | 0 |
| Total dihedral angle restraints | 158 |
|   phi | 79 |
|   psi | 79 |
| | |
| Structure statistics | |
| Violations (mean and s.d.) | |
|   Distance constraints (Å) | 0.083 ± 0.039 |
|   Dihedral angle constraints (°) | 2.407 ± 0.357 |
|   Max. dihedral angle violation (°) | 10.267 |
|   Max. distance constraint violation (Å) | 0.248 |
| Deviations from idealized geometry | |
|   Bond lengths (Å) | 0.013 |
|   Bond angles (°) | 1.9 |
| Average pairwise r.m.s.d.** (Å) | |
|   Heavy | 1.1 |
|   Backbone | 0.7 |

**Pairwise r.m.s.d. was calculated among ordered residues (3-83) of 10 refined structures.

Figure 5

| Library name | Number of molecules |
| --- | --- |
| Biomol ICCB Known Bioactives3 | 430 |
| Ninds Custom Collection 2 | 1,040 |
| Prestwick 1 Collection | 1,120 |
| Asinex 1 | 12,378 |
| ChemBridge 3 | 10,560 |
| ChemDiv 4 | 14,677 |
| Enamine 2 | 26,576 |
| Life Chemicals 1 | 3,893 |
| Maybridge 5 | 3,212 |
| ChemDiv 3 | 16,544 |
| Maybridge 1 | 8,800 |
| ChemDiv 6 | 44,000 |
|  |  |
| Total number of molecules | 143,280 |
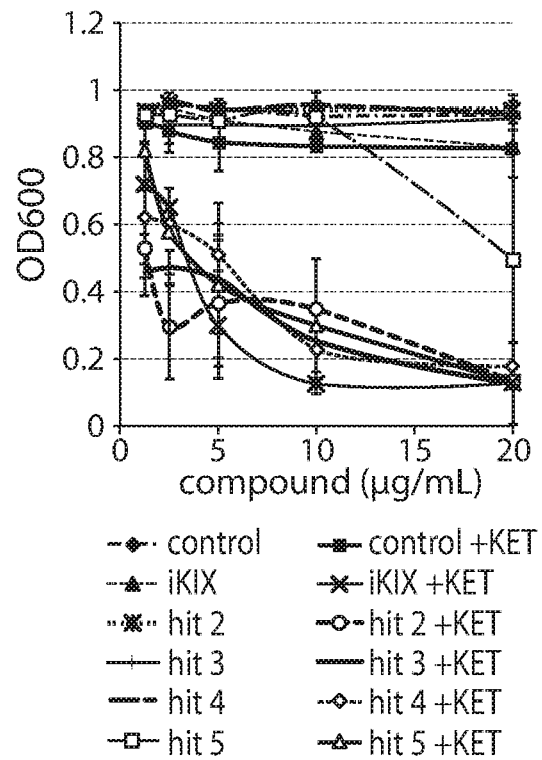
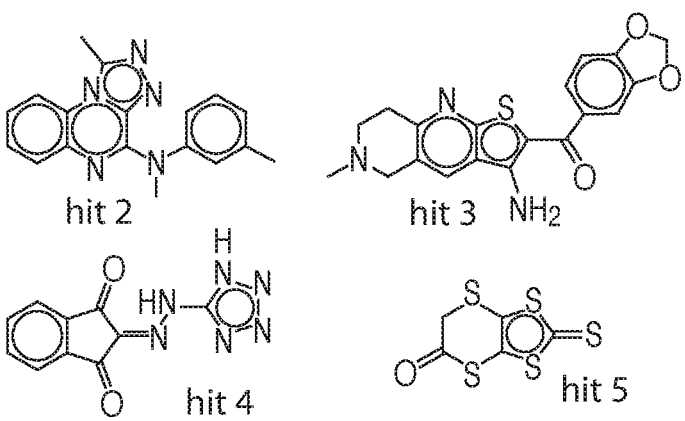
Figure 6

|  | average *CDR1* delta Cp, no KET | standard deviation, no KET | average *CDR1* delta Cp, +KET | standard deviation, +KET |
| --- | --- | --- | --- | --- |
| SFY114 (+) DMSO | 16.00 | 0.32 | 10.59 | 0.18 |
| SFY114 (+) 10 μM iKIX1 | 15.99 | 0.22 | 11.79 | 0.71 |
| SFY114 (+) 30 μM iKIX1 | 15.57 | 0.57 | 13.78 | 0.40 |
| L280F DMSO | 15.59 | 0.52 | 13.26 | 0.39 |
| L280F 10 μM iKIX1 | 15.69 | 0.33 | 13.40 | 0.58 |
| L280F 30 μM iKIX1 | 15.11 | 0.33 | 14.68 | 0.28 |
| Y584C DMSO | 15.10 | 0.35 | 10.35 | 0.21 |
| Y584C 10 μM iKIX1 | 16.09 | 0.17 | 12.36 | 0.36 |
| Y584C 30 μM iKIX1 | 16.14 | 0.20 | 14.51 | 0.19 |
| T588A DMSO | 14.64 | 0.85 | 11.30 | 0.55 |
| T588A 10 μM iKIX1 | 15.52 | 0.34 | 12.60 | 0.52 |
| T588A 30 μM iKIX1 | 15.49 | 0.36 | 14.57 | 0.76 |
| P822L DMSO | 15.05 | 0.70 | 13.13 | 0.33 |
| P822L 10 μM iKIX1 | 15.06 | 0.44 | 14.35 | 0.30 |
| P822L 30 μM iKIX1 | 15.57 | 0.57 | 14.91 | 0.63 |
| D1082G DMSO | 13.89 | 0.13 | 11.96 | 0.37 |
| D1082G 10 μM iKIX1 | 14.15 | 0.20 | 13.05 | 0.35 |
| D1082G 30 μM iKIX1 | 14.37 | 0.41 | 14.52 | 0.48 |

Figure 9D

| IC50 Ket (µM) | IC50 iKIX1 (µM) | CI |
|---|---|---|
| 0 | 5 | 1.00 |
| 0.015625 | 4.5 | 0.96 |
| 0.03125 | 4 | 0.93 |
| 0.125 | 2 | 0.90 |
| 0.125 | 1 | 0.70 |
| 0.25 | 0 | 1.00 |

| IC50 Ket (µM) | IC50 iKIX1 (µM) | CI |
|---|---|---|
| - | 6 | N/A |
| 0.125 | 5 | 0.85 |
| 0.25 | 4 | 0.71 |
| 0.5 | 3 | 0.58 |
| 1 | 2 | 0.50 |
| 2 | 1 | 0.50 |
| 4 | 0.5 | 0.75 |
| 4 | 0.25 | 0.71 |
| 6 | - | N/A |

| Route | Dose (mg/kg) | $T_{max}$ (h) | $C_0/C_{max}$ (ng/mL) | $AUC_{last}$ (hr·ng/mL) | $AUC_{INF}$ (hr·ng/mL) | $T_{1/2}$ (h) | Cl (mL/min/kg) | $V_{ss}$ (L/kg) | F (%) |
|---|---|---|---|---|---|---|---|---|---|
| i.v. | 2 | - | 12674.51 | 1502.00 | 1521.92 | 5.93 | 21.90 | 2.23 | - |
| p.o. | 10 | 0.25 | 336.59 | 455.95 | 456.05 | - | - | - | 6 |

Figure 12H

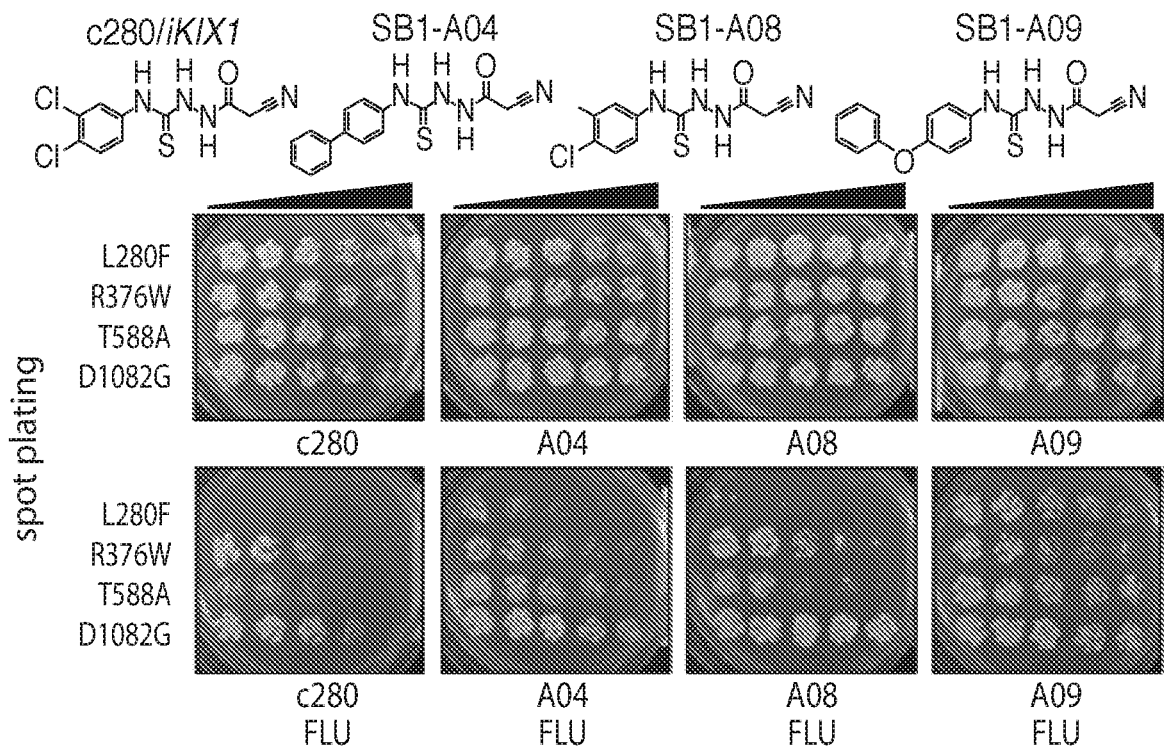
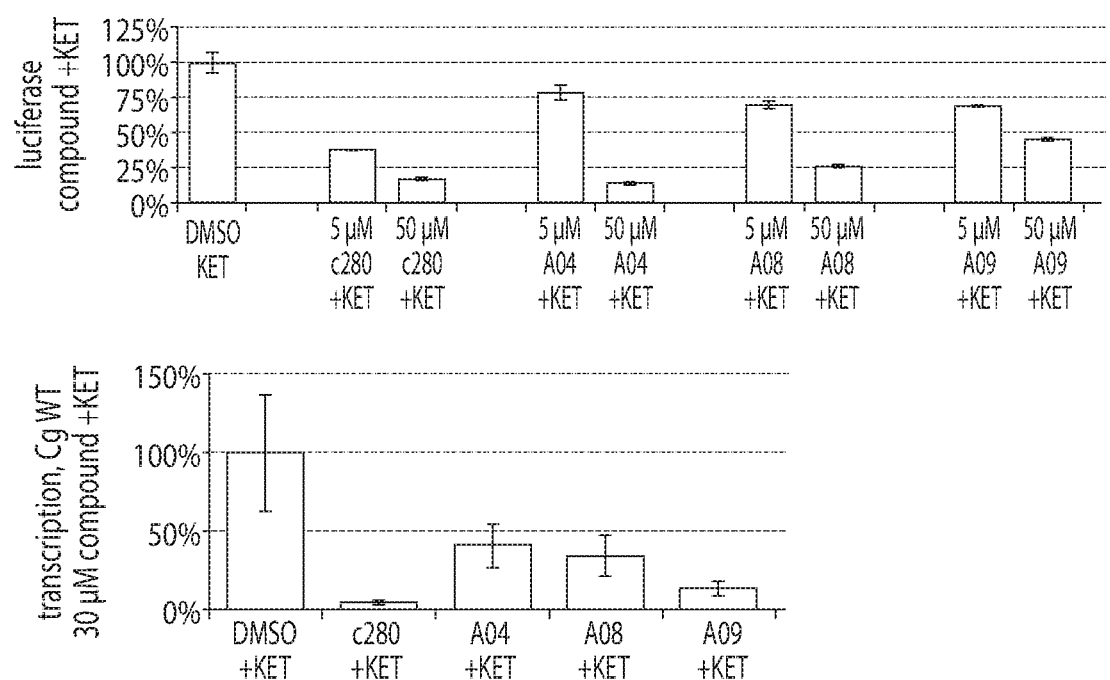
Figure 16

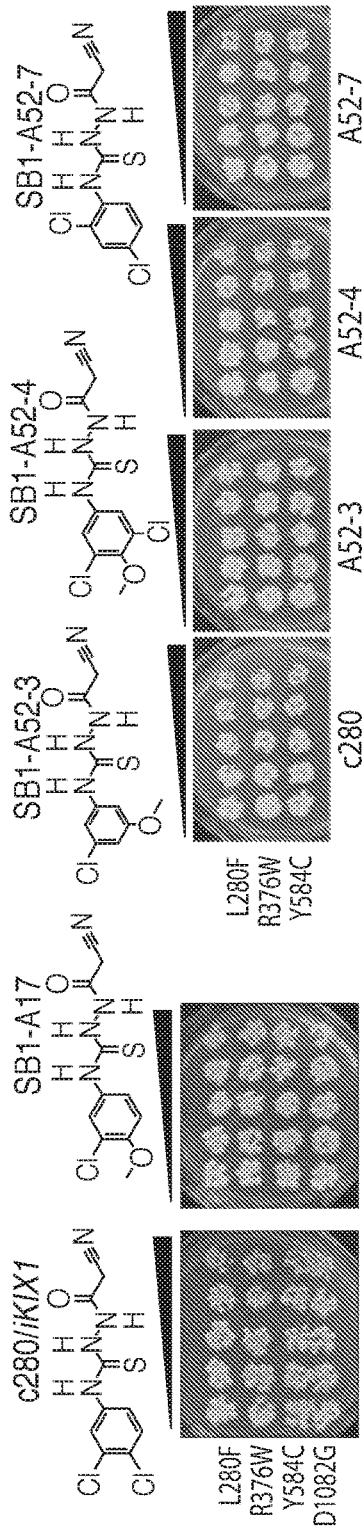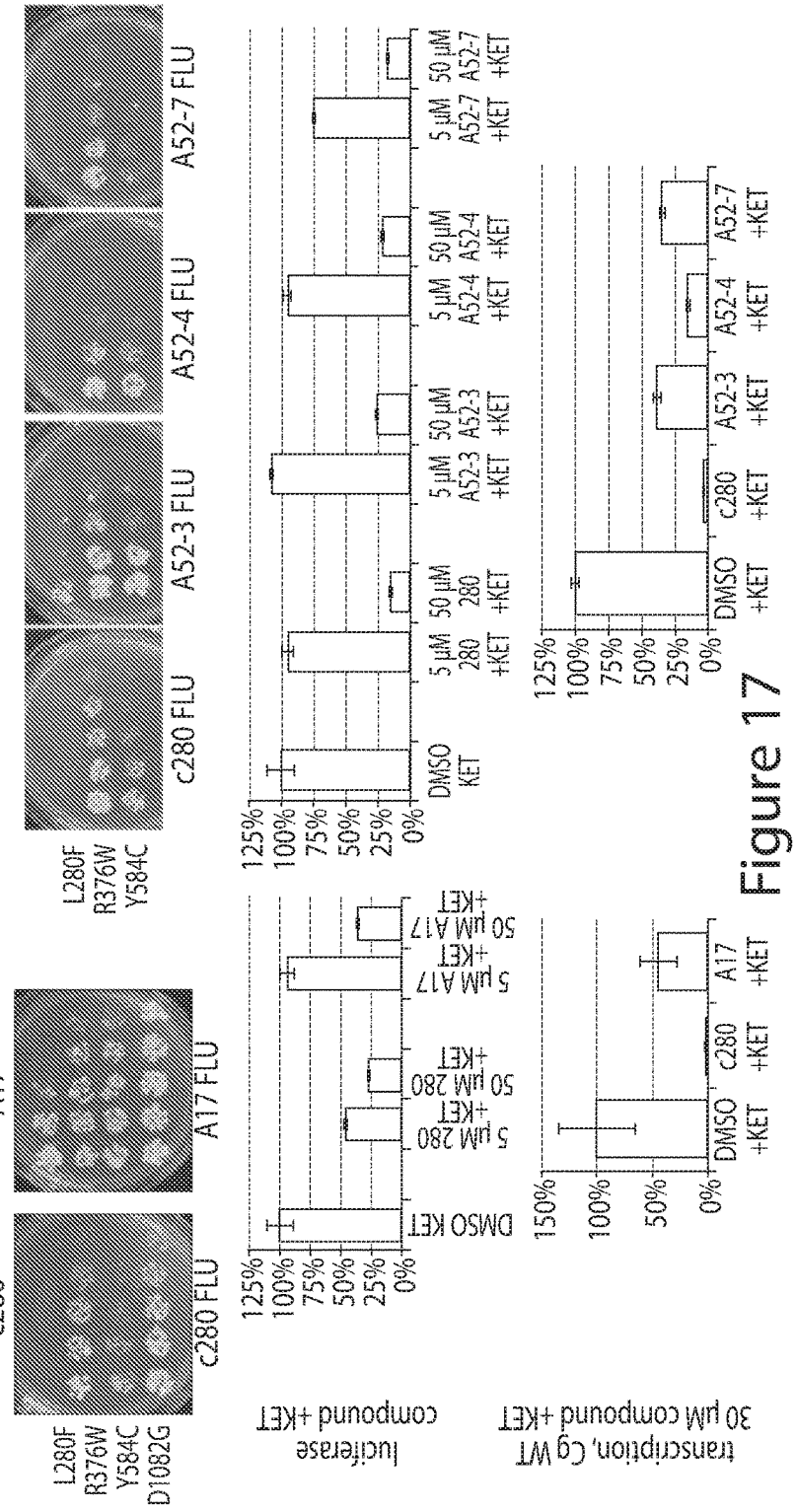
Figure 17

```
                        SEQUENCE LISTING

<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Modified by FITC

<400> SEQUENCE: 1

Leu Gly Thr Leu Asp Glu Phe Val Asn Lys Gly Asp Leu Asn Glu Leu
1               5                   10                  15

Tyr Asn Ser Leu Trp Gly Asp Leu Phe Ser Asp Val Tyr Leu
            20                  25                  30

<210> SEQ ID NO 2
<211> LENGTH: 43
<212> TYPE: PRT
<213> ORGANISM: Saccharomyces cerevisiae

<400> SEQUENCE: 2

Val Gln Asp Lys Asp Thr Leu Ser Asn Ala Glu Arg Ala Lys Asn Val
1               5                   10                  15

Asn Gly Leu Leu Gln Val Leu Met Asp Ile Asn Thr Leu Asn Gly Gly
            20                  25                  30

Ser Ser Asp Thr Ala Asp Lys Ile Arg Ile His
        35                  40

<210> SEQ ID NO 3
<211> LENGTH: 43
<212> TYPE: PRT
<213> ORGANISM: Candida glabrata

<400> SEQUENCE: 3

Met Ser Ser Lys Glu Thr Ile Pro Met His Gln Arg Ser Gln Asn Val
1               5                   10                  15

Ala Glu Leu Leu Thr Val Leu Met Asp Ile Asn Lys Ile Asn Gly Gly
            20                  25                  30

Asp Ser Thr Thr Ala Glu Lys Met Lys Val His
        35                  40

<210> SEQ ID NO 4
<211> LENGTH: 42
<212> TYPE: PRT
<213> ORGANISM: Saccharomyces cerevisiae

<400> SEQUENCE: 4
```

```
Ala Lys Asn Phe Glu Ala Ala Leu Phe Ala Lys Ser Ser Ser Lys Lys
1               5                   10                  15

Glu Tyr Met Asp Ser Met Asn Glu Lys Val Ala Val Met Arg Asn Thr
                20                  25                  30

Tyr Asn Thr Arg Lys Asn Ala Val Thr Ala
            35                  40

<210> SEQ ID NO 5
<211> LENGTH: 43
<212> TYPE: PRT
<213> ORGANISM: Candida glabrata

<400> SEQUENCE: 5

Ala Lys Ser Phe Glu Ala Ala Leu Phe Glu Lys Ser Ser Ser Lys Glu
1               5                   10                  15

Glu Tyr Gln Lys Thr Met Lys Ser Lys Ile Asp Ala Met Arg Ser Thr
                20                  25                  30

Arg Asp Lys Arg Lys Arg Glu Ser Val Gly Ser
            35                  40
```

ANTIFUNGAL COMPOUNDS AND USES THEREOF

RELATED APPLICATIONS

This application is a national stage filing under 35 U.S.C. § 371 of International PCT Application, PCT/US2017/018433, filed Feb. 17, 2017, which claims priority under 35 U.S.C. § 119(e) to U.S. Provisional Patent Application, U.S. Ser. No. 62/296,529, filed Feb. 17, 2016, the entire contents of each of which are incorporated herein by reference.

GOVERNMENT SUPPORT

This invention was made with government support under grant number P01 GM047467 awarded by the National Institutes of Health. The government has certain rights in the invention.

BACKGROUND OF THE INVENTION

Eukaryotic transcription activators stimulate the expression of specific sets of target genes through recruitment of co-activators such as the RNA polymerase II-interacting Mediator complex (see. e.g., Conaway, R. C. & Conaway, J. W. Function and regulation of the Mediator complex. *Current opinion in genetics & development* 21, 225-230, doi:10.1016/j.gde.2011.01.013 (2011); Poss, Z. C., Ebmeier, C. C. & Taatjes, D. J. The Mediator complex and transcription regulation. *Critical reviews in biochemistry and molecular biology* 48, 575-608. doi:10.3109/10409238.2013.840259 (2013)). Aberrant function of transcription activators has been implicated in a number of diseases. However, therapeutic targeting efforts have been hampered by a lack of detailed molecular knowledge of the mechanisms of gene activation by disease-associated transcription activators. An activator-targeted three-helix bundle KIX domain was previously identified in the human MED 15 Mediator subunit that is structurally conserved in Gal11/Med15 Mediator subunits in fungi (See, e.g., Thakur, J. K. et al. A nuclear receptor-like pathway regulating multidrug resistance in fungi. *Nature* 452, 604-609, doi:nature06836 [pii] 10.1038/nature06836 (2008); Yang, F. et al. An ARC/Mediator subunit required for SREBP control of cholesterol and lipid homeostasis. *Nature* 442, 700-704 (2006)). The Gal11/Med15 KIX domain engages pleiotropic drug resistance transcription factor (Pdr1) orthologues, which are key regulators of the multidrug resistance (MDR) pathway in *S. cerevisiae* and in the clinically important human pathogen *Candida glabrata* (see, e.g., Paul, S. & Moye-Rowley, W. S. Multidrug resistance in fungi: regulation of transporter-encoding gene expression. *Frontiers in physiology* 5, 143. doi:10.3389/fphys.2014.00143 (2014); Prasad, R. & Goffeau, A. Yeast ATP-binding cassette transporters conferring multidrug resistance. *Annual review of microbiology* 66, 39-63, doi:10.1146/annurev-micro-092611-150111 (2012)).

The prevalence of *C. glabrata* is rising, partly due to their low intrinsic susceptibility to azoles, the most widely used antifungal (see, e.g., Pfaller, M. A. et al. Variation in susceptibility of bloodstream isolates of *Candida glabrata* to fluconazole according to patient age and geographic location in the United States in 2001 to 2007. *J Clin Microbiol* 47, 3185-3190, doi:JCM.00946-09 [pii] 10.1128/JCM.00946-09 (2009); Pfaller, M. A., Messer, S. A., Moet, G. J., Jones, R. N. & Castanheira, M. Candida bloodstream infections: comparison of species distribution and resistance to echinocandin and azole antifungal agents in Intensive Care Unit (ICU) and non-ICU settings in the SENTRY Antimicrobial Surveillance Program (2008-2009). *Int J Antimicrob Agents* 38, 65-69, doi:S0924-8579(11)00132-4 [pii]10.1016/j.ijantimicag.2011.02.016). Drug-resistant clinical isolates of *C. glabrata* most commonly harbour point mutations in Pdr1 that render it constitutively active suggesting that this transcriptional activation pathway represents a linchpin in *C. glabrata* MDR (see, e.g., Ferrari, S. et al. Gain of function mutations in CgPDR1 of *Candida glabrata* not only mediate antifungal resistance but also enhance virulence. *PLoS Pathog* 5, e1000268, doi:10.1371/journal.ppat.1000268 (2009); Ferrari, S., Sanguinetti, M., Torelli, R., Posteraro, B. & Sanglard, D. Contribution of CgPDR1-regulated genes in enhanced virulence of azole-resistant *Candida glabrata*. *PLoS one* 6, e17589, doi:10.1371/journal.pone.0017589 (2011); Silva, L. V. et al. Milbemycins: more than efflux inhibitors for fungal pathogens. *Antimicrobial agents and chemotherapy* 57, 873-886, doi:10.1128/AAC.02040-12 (2013); Vermitsky, J. P. et al. Pdr1 regulates multidrug resistance in *Candida glabrata*: gene disruption and genome-wide expression studies. *Mol Microbiol* 61, 704-722 (2006); Sanguinetti, M. et al. Mechanisms of azole resistance in clinical isolates of *Candida glabrata* collected during a hospital survey of antifungal resistance. *Antimicrob Agents Chemother* 49, 668-679, doi: 49/2/668 [pii] 10.1128/AAC.49.2.668-679.2005 (2005); Caudle, K. E. et al. Genomewide expression profile analysis of the *Candida glabrata* Pdr1 regulon. *Eukaryot Cell* 10, 373-383, doi:EC.00073-10 [pii] 10.1128/EC.00073-10). Therefore, new anti-infectives are needed for the treatment of infectious diseases, especially those exhibiting multi-drug resistance (MDR).

SUMMARY OF THE INVENTION

As described herein, sequential biochemical and in vivo high-throughput screens have been carried out to identify small molecule inhibitors of the interaction of the *C. glabrata* Pdr1 activation domain with the *C. glabrata* Gal11A KIX domain. The compounds can be used for treating diseases (e.g., infectious diseases) and/or for killing or inhibiting the growth of fungi. In certain embodiments, for example, the compounds inhibit Pdr1-dependent gene activation and re-sensitize drug-resistant *C. glabrata* to azole antifungals in vitro and in animal models for disseminated and urinary tract *C. glabrata* infection. Determining the NMR structure of the *C. glabrata* Gal11A KIX domain provided a detailed understanding of the molecular mechanism of Pdr1 gene activation and MDR inhibition by iKIX1. As described herein, the feasibility of small molecule targeting of a transcription factor-binding site in Mediator as a novel therapeutic strategy in treating diseases (e.g., fungal infectious disease) has been demonstrated.

In one aspect, the present invention provides compounds of Formula (II):

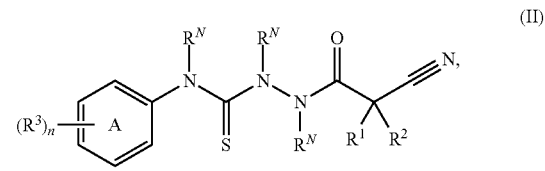

and pharmaceutically acceptable salts, hydrates, solvates, polymorphs, co-crystals, tautomers, stereoisomers, isotopically labeled derivatives, and prodrugs thereof, wherein $R^1$, $R^2$, $R^3$, $R^N$, and n are as defined herein.

Also provided herein are compounds of Formula (III):

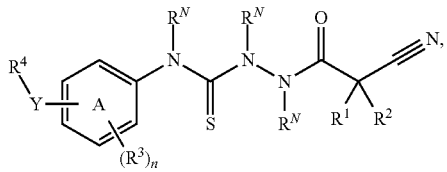

and pharmaceutically acceptable salts, hydrates, solvates, polymorphs, co-crystals, tautomers, stereoisomers, isotopically labeled derivatives, and prodrugs thereof, wherein $R^1$, $R^2$, $R^3$, $R^4$, $R^N$, Y, and n are as defined herein.

Exemplary compounds of the present invention include, but are not limited to, the following:

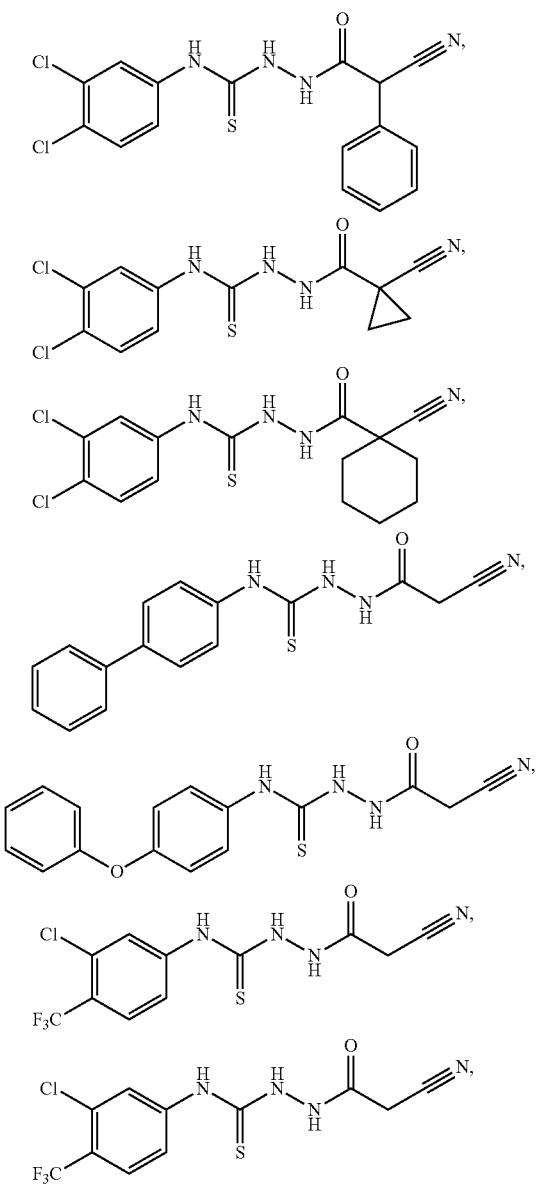

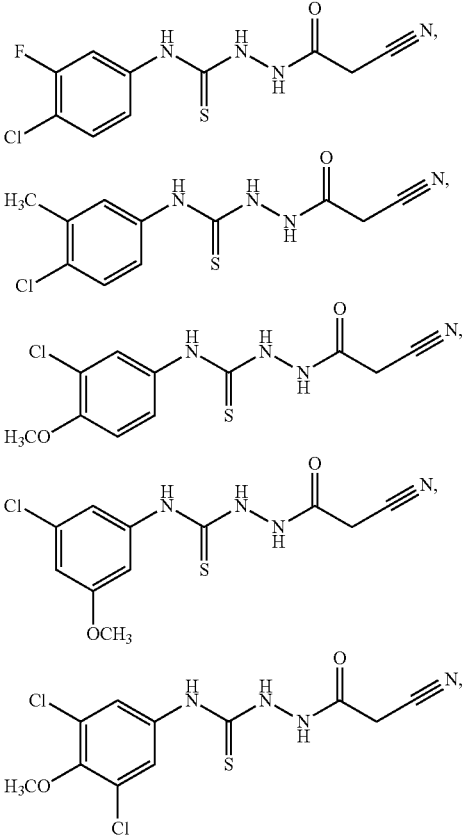

and pharmaceutically acceptable salts, hydrates, solvates, polymorphs, co-crystals, tautomers, stereoisomers, isotopically labeled derivatives, and prodrugs thereof.

In another aspect, the present invention provides pharmaceutical compositions comprising a compound provided herein, or a pharmaceutically acceptable salt, hydrate, solvate, polymorph, co-crystal, tautomer, stereoisomer, isotopically labeled derivative, or prodrug thereof, and a pharmaceutically acceptable excipient. The pharmaceutical composition may comprise an effective amount (e.g., a therapeutically or prophylactically effective amount)

In yet another aspect, the present invention provides uses of the compounds and pharmaceutical compositions described herein for the treatment of diseases (e.g., infectious diseases such an fungal infections), for inhibiting the activity of a fungus in a subject or biological sample, for the killing of a fungus in a subject or biological sample, and/or for inhibiting the growth of a fungus in a subject or a biological sample. The methods of use provided herein may be carried out, for example, in or on a subject, in a clinical setting, or in an agricultural setting (e.g., on a plant). The methods of use provided herein may be carried out in vitro or in vivo.

In yet another aspect, the present invention provides kits (e.g., pharmaceutical packs) comprising a compound described herein, or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the kit comprises an addition therapeutic agent (e.g., an anti-infective agent). In certain embodiments, the kit further comprises instructions for use or administration.

The details of certain embodiments of the invention are set forth in the Detailed Description of Certain Embodiments, as described below. Other features, objects, and advantages of the invention will be apparent from the Definitions, Examples, Figures, and Claims.

Definitions

Chemical Definitions

Definitions of specific functional groups and chemical terms are described in more detail below. The chemical elements are identified in accordance with the Periodic Table of the Elements, CAS version. *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*. 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-4}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

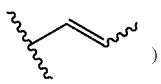
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of)

and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-?}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_4$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C?) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocylyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(═O)R$^{aa}$, —CO$_2$H, —CHO, —C(OR$^{cc}$)$_2$, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —C(═NR$^{bb}$)R$^{aa}$, —C(═NR$^{bb}$)OR$^{aa}$, —OC(═NR$^{bb}$)R$^{aa}$, —OC(═NR$^{bb}$)OR$^{aa}$, —C(═NR$^{bb}$)N(R$^{bb}$)$_2$, —OC(═NR$^{bb}$)N(R$^{bb}$)$_2$, —NR$^{bb}$C(═NR$^{bb}$)N(R$^{bb}$)$_2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —OSO$_2$R$^{aa}$, —S(═O)R$^{aa}$, —OS(═O)R$^{aa}$, —Si(R$^{aa}$)$_3$, —OSi(R$^{aa}$)$_3$—C(═S)N(R$^{bb}$)$_2$, —C(═O)SR$^{aa}$, —C(═S)SR$^{aa}$, —SC(═S)SR$^{aa}$, —SC(═O)SR$^{aa}$, —OC(═O)SR$^{aa}$, —SC(═O)OR$^{aa}$, —SC(═O)R$^{aa}$, —P(═O)(R$^{aa}$)$_2$, —P(═O)(OR$^{cc}$)$_2$, —OP(═O)(R$^{aa}$)$_2$, —OP(═O)(OR$^{cc}$)$_2$, —P(═O)(N(R$^{bb}$)$_2$)$_2$, —OP(═O)(N(R$^{bb}$)$_2$)$_2$, —NR$^{bb}$P(═O)(R$^{aa}$)$_2$, —NR$^{bb}$P(═O)(OR$^{cc}$)$_2$, —NR$^{bb}$P(═O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group ═O, ═S, ═NN(R$^{bb}$)$_2$, ═NNR$^{bb}$C(═O)R$^{aa}$, ═NNR$^{bb}$C(═O)OR$^{aa}$, ═NNR$^{bb}$S(═O)$_2$R$^{aa}$, ═NR$^{bb}$, or ═NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —SO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(CM, alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{gg}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N*-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-niiropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{bb}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fiuoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, tri phenyl methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorxliphenylacelate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*. T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PF$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OdC(CF$_3$)$_3$)$_4{}^-$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4{}^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

An "infectious disease" refers to any disease caused by a pathogen (i.e., pathogenic microorganisms). An infectious disease may be caused by bacteria, viruses, parasites, or fungi. An infectious disease can be a microbial infection. A "microbial infection" refers to an infection with a microorganism, such as a fungus, bacteria or virus. In certain embodiments, the microbial infection is an infection with a fungus, i.e., a fungal infection. In certain embodiments, the microbial infection is an infection with a virus, i.e., a viral infection. In certain embodiments, the microbial infection is an infection with a bacteria, i.e., a bacterial infection. Various microbial infections include, but are not limited to, skin infections, GI infections, urinary tract infections, genito-urinary infections, sepsis, blood infections, and systemic infections. In certain embodiments, the infectious disease is a bacterial infection. In certain embodiments, the infectious disease is a viral infection. In certain embodiments, the infectious disease is a microbial infection.

"Anti-infective agents" and the like include "antibiotics," "antibacterial agents" and "antifungal agents." Anti-infective agents are agents that are capable of killing or inhibiting the growth of pathogens (e.g., bacteria, viruses, parasites, or fungi). In certain embodiments, the anti-infective agent is an antibacterial agent. In certain embodiments, the anti-infective agent is (−)-Florfenicol, Acetylsulfisoxazole, Actinonin, Amikacin sulfate, Benzethonium chloride, Cephalosporins (e.g. 7-Aminocephalosporanic acid, 7-Aminodeacetoxycephalosporanic acid, Cefaclor, Cefadroxil, Cefamnandole, Cefazolin, Cefepime, Cefixime, Cefmenoxinme, Cefmetazole, Cefoperazone, Cefotaxime, Cefotetan, Cefotiam, Cefoxitin, Cefpirome, Cefpodoxime proxetil, Cefsulodin, Cefsulodin sodium, Ceftazidime, Ceftizoxime, Ceftriaxone, Cefuroxime, Cephalexin, Cephaloridine, Cephalosporin C, Cephalothin, Cephalothin sodium, Cephapirin, Cephradine), Cetrimide, Chelerythrine, Chlorhexidine (e.g. Chlorhexidine gluconate), Chlorhexidine acetate, Chlorhexidine gluconate, Chlorothalonil, Ciprofloxacin (e.g. Enrofloxacin), Clarithromycin, Ciavulanic acid (e.g. Amoxicillin-clavulanic acid), Clindamycin, Co-Trimoxazole, Dichlorophene, Didecyldimethylanmnonium chloride, Dihydrostreptomycin, Enoxacin, Ethambutol, Fleroxacin, Furazolidone, Grepafloxacin hydrochloride, Levofloxacin, Linezolid, Lomefloxacin, Methylisothiazolinone, Monolaurin, Oxolinic acid, Pefloxacin, Penicillin (e.g. 6-Aminopenicillanic acid, Amoxicillin (e.g. Amoxicillin-clavulanic acid), Ampicillin, Ampicillin sodium, Azlocillin, Carbenicillin, Cefoxitin, Cephaloridine, Cloxacillin, Dicloxacillin, Mecillinam, Methicillin, Mezlocillin, Nafcillin, Oxacillin, Penicillin G, Penicillin G potassium, Penicillin G procaine Penicillin G sodium, NT2 Penicillin V, Piperacillin, Piperacillin-tazobactam, Sulbactam, Tazobactam, Ticarcillin), Povidone-iodine, Rotproofing agents, Salinomycin, Sparfloxacin, Spirocheticides (e.g. Arsphenamine, Neoarsphenamine), NT1 Sulbactam, NT1 Sulfaquinoxaline, NT1 Tetracyclines (e.g. Achromycin V, Demeclocycline, Doxycycline, Doxycycline monohydrate, Minocycline, Oxytetracycline, Oxytetracycline hydrochloride, Tetracycline, Tetracycline hydrochloride), Thiamphenicol, Tinidazole, Triclosan, Trovafloxacin, Tuberculostatics (e.g. 4-Aminosalicylic acid, AZD 5847, Anminosalicyiic acid, Ethionanmide), Vidarabine, Zinc pyrithione, or Zirconium phosphate. In certain embodiments, the additional pharmaceutical agent is an antiviral agent. In certain embodiments, the additional pharmaceutical agent is (−)-Oseltamivir, β-D-Ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g. Amantadine hydrochloride), Amantadine hydrochloride, anti-HIV agent (e.g. Abacavir, Amprenavir, Atazanavir, Azidothymidine, Bryostatin (e.g. Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciciovir, Integrase inhibitors (e.g. 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin. Vidarabine, or virus entry inhibitor (e.g. Enfuvirtide, Maraviroc). In certain embodiments, the additional pharmaceutical agent is a fungicide. In certain embodiments, the additional pharmaceutical agent is (−)-Fumagillin, (−)-Metalaxyl, 1,2,5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl A1, Griseofulvin, Guanidine (e.g. Agmatine, Amiloride hydrochloride, Biguanide (e.g. Imidodicarbonimidic diamide, N,N-dimethyl-,hydrochloride (1:1) (e.g. Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine. Pentachloronitrobenzene, Prochloraz, Procymidone, Propiconazole, Pyrazophos, Reduced viscotoxin A3, Salicylanilide, Tebuconazole, Terbinafine. Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g. Artemisinin, Chloroquine (e.g. Chloroquine phosphate), Mefloquine, Sulfadoxine), Coccidiostat, Leishmanicide, Trichomonacide, or Trypanosomicide (e.g. Eflornithine). In certain embodiments, the additional pharmaceutical agent is a parasiticide. In certain embodiments, the additional pharmaceutical agent is Anthelmintic (e.g. Abamectin, Dimethylformocarbothialdine, Niclosamide, Schistosomicide), Protozoacide (e.g. Amebicide, Antimalarial (e.g. Artemisinin, Chloroquine (e.g. Chloroquine phosphate), Mefloquine, Sulfadoxine), Coccidiostat. Leishmanicide, Trichomonacide, or Trypanosomicide (e.g. Eflornithine)). In certain embodiments, the additional pharmaceutical agent is a β-lactam antibiotic. Exemplary β-lactam antibiotics include, but are not limited to: β-lactamase inhibitors (e.g., avibactam, clavulanic acid, tazobactam, sulbactam); carbacephems (e.g., loracarbef); carbapenems (e.g., doripenem, imipenem, ertapenem, meropenem); cephalosporins (1st generation) (e.g., cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cephalosporin C); cephalosporins (2nd generation) (e.g., cefaclor, cefamandole, cefbuperzone, cefmetazole, cefonicid, ceforanide, cefotetan, cefotiam, cefoxitin, cefminox, cefprozil, cefuroxime, cefuzonam); cephalosporins (3rd generation) (e.g., cefcapene, cefdaloxime, cefdinir, cefditoren, cefetamet, cefixime, cefmenoxime, cefodizime, cefoperazone, cefotaxime, cefovecin, cefpimizole, cefpiramide, cefpodoxime, cefiamere, ceftazidime, cefteram, ceftibuten, ceftiofur, ceftiolene, ceftizoxime, ceftriaxone, latamoxef); cephalosporins (4th generation) (e.g., cefepime, cefluprenam, cefoselis, cefozopran, cefpirome, cefquinome, flomoxef); cephalosporins (5th generation) (e.g., ceftaroline fosamil, ceftobiprole, ceftolozane); cephems (e.g., cefaloram, cefaparole, cefcanel, cefedrolor, cefempidone, cefetrizole, cefivitril, cefmepidium cefoxazole, cefrotil, cefsulodin, cefsumide, ceftioline, ceftioxime, cefuracetime, nitrocefin); monobactams (e.g., aztreonam, carumonam, norcadicin A, tabtoxinine β-lactam, tigemonam); penicillins/penams (e.g., amoxicillin, amoxicillin/clavulanate, ampicillin, ampicillin/flucloxacillin, ampicillin/sulbactam, azidocillin, azlocillin, bacampacillin, benzathine benzylpenicillin, benzathine phenoxymethylpenicillin, carbenicillin, carindacillin, clometocillin, cloxacillin, dicloxacillin, epicillin, flucloxacillin, hetacllin, mecillinam, mezlocillin, meticillin, metampiciillin, nafcillin, oxacillin, penamacillin, penicillin G, penicillin V, phenaticillin, piperacillin, piperacillin/tazobactam, pivampicillin, pivmeclilllinam, procaine benzylpenicillin, propicillin, sulbenicillin, talampicillin, temocllin, ticarcillin, ticarcillin/clavulanate); and penems/carbapenems (e.g., biapenem, doripenem, ertapenem, faropenem, imipenem, imipenem/cilastatin, lenapenem, meropenem, panipenem, razupenem, tebipenem, thienamycin, tomopenem). In certain embodiments, the additional pharmacetucial agent is a non-β-lactam antibiotic. Exemplary non-β-lactam antibiotics include, but are not limited to: aminoglycosides (e.g., amikacin, dibekacin, gentamicin, kanamycin, neomycin, netilmicin, tobramycin, paromomycin, sisomicin, streptomycin, spectinomycin); ansamycins (e.g., geldanamycin, herbimycin); glycopeptides (e.g., belomycin, dalbavancin, oritavancin, ramoplanin, teicoplanin, televancin, vancomycin); glycylcyclines (e.g., tigecycline); lincosamides (e.g., clindamycin, lincomycin); lipopeptides (e.g., anidulafungin, caspofungin, cilofungin, daptomycin, echinocandin B, micafungin, mycosubtilin); macrolides (e.g., azithromycin, carbomycin A, clarithromycin, dirithromycin, erythromycin, josmycin, kitasamycin, midecamycin, oleandomycin, roxithromycin, solithromycin, spiramycin, troleandomycin, telithromycin, tylosin); nitrofurans (e.g., furazolidone, furylfuramide, nitrofurantoin, nitrofurazone, nifuratel, nifurquinazol, nifurtoinol, nifuroxazide, nifurtimox, nifurzide, ranbezolid); nitroimidazoles (e.g., metronidazole, nimorazole, tinadazole); oxazolidinones (e.g., cycloserine, linezolid, posizolid radezolid, tedizolid); polypeptides (e.g., actinomycin, bacitracin, colistin, polymyxin B); quinolones (e.g., balofloxacin, besifloxacin, cinoxacin, ciprofloxacin, clinafloxacin, danofloxacin, delafloxacin, difloxacin, enoxacin, enrofloxacin, fleroxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin, trovafloxacin); rifamycins (e.g., rifamycin B, rifamycin S, rifamycin SV, rifampicin, rifabutin, rifapentine, rifalazil, rifaximin); sulfonamides (e.g., co-trimoxazole, mafenide, pediazole, sulfacetamide, sulfadiazine, silver sulfadiazine, sulfadimidine, sulfadimethoxine, sulfadoxine, sulfafurazole, sulfamethizole, sulfamethoxazole, sulfamethoxypyridazine, sulfametopyrazine, sulfametoxydiazine, sulfamoxole, sulfanilamide, sulfanitran, sulfasalazine, sulfisomidine, sulfonamidochrysoidine, trimethoprim); tetracyclines (e.g., 6-deoxytetracycline, aureomycin, chlortetracycline, demeclocycline, doxycycline, lymecycline, meclocycline, methacycline, minocycline, oxytetracycline, PTK-0796, sancycline, rolitetracycline, tetracycline, terramycin); tuberactinomycins (e.g., tuberactinomycin A, tuberactinomycin 0, viomycin, enviomycin, capreomycin); arsphenamine; chloramphenicol; dalfoprisitin; fosfomycin; fusidic acid; fidaxomycin, gramicidin; lysozyme; mupirocin; platensimycin; pristinamycin; sparsomycin; quinupristin; quinupristin/dalfopristin; teixobactin; and thiamphenicol.

Antifungal agents include azole antifungal agents. "Azole antifungal agents" are antifungal agents that contain azole moieties (e.g., imidazoles, triazoles, and thiazoles). Azole antifungal agents include, but are not limited to, imidazoles (e.g., Bifonazole, Butoconazole, Clotrimazole, Econazole. Fenticonazole, Isoconazole, Ketoconazole. Luliconazole, Miconazole, Omoconazole, Oxiconazole, Sertaconazole, Sulconazole, Tioconazole), triazoles (e.g., Albaconazole, Efinaconazole, Epoxiconazole, Fluconazole, Isavuconazole, Itraconazole, Posaconazole, Propiconazole, Ravuconazole. Terconazole. Voriconazole), and thiazoles (e.g., Abafungin).

BRIEF DESCRIPTION OF THE DRAWINGS

The accompanying drawings, which constitute a part of this specification, illustrate several embodiments of the invention and together with the description, serve to explain the principles of the invention.

FIG. 1A. Schematic of the screening process.

FIG. 2A. Backbone representation of the 10 lowest energy NMR structures of CgGal11A KIX domain; backbone RMSD~0.7 Å, left. Overlay of CgGal11A (purple) and S. cerevisiae Gal11/Med15 (blue) KIX domains, with an overall RMSD of 2.0 Å, right (see, e.g., Krissinel. E. & Henrick, K. Secondary-structure matching (SSM), a new tool for fast protein structure alignment in three dimensions. Acta Crystallogr D Biol Crystallogr 60, 2256-2268, doi:S0907444904026460 [pii] 10.1107/S0907444904026460 (2004)). FIG. 2B. Chemical shift perturbations (CSPs) on the CgGal11A KIX domain in the presence of CgPdr1 AD (red) or iKIX1 (blue). Residues coloured in red or blue indicate a chemical shift perturbation greater than 2 s.d. Residues highlighted in green (L19, L23 and L51) represent significant CSPs in the side-chain methyl groups of an ILV labeled sample. FIG. 2C. The iKIX1 and CgPdr1 AD target the hydrophobic groove on the CgGal11A KIX domain, which is surrounded by a basic patch. Residues H43, K54, K68, K78, R79, F47 and M72 present a positive electrostatic surface enclosing the binding interface. FIG. 2D, iKIX1 docked to the CgGal11A KIX domain, iKIX1 is depicted as red sticks and spheres. Residues that experience significant methyl CSP upon addition of iKIX1 are depicted as blue sticks.

FIG. 3A, iKIX1 inhibits ketoconazole (KET)-induced upregulation of luciferase activity in a dose-responsive manner in a Sc pdr1Δpdr3Δ strain containing plasmid-borne CgPDR1 and 3×PDRE-luciferase. (UT): untreated control; P<0.001. FIGS. 3B and 3C, iKIX1 prevents the ketoconazole (KET)-induced recruitment of Gal11/Med15/Mediator to the upstream activating sequences (UAS) of the PDRE-regulated promoter ScPDR5 (FIG. 3B), and ScPDR5 induction (FIG. 3C). Representative experiment from two biological replicates (ChIP DNA and RNA from same experiment) is shown. Error bars indicate s.d. of technical replicates; *P<0.00001, **P<0.0005, and *P<0.01 by two-tailed Student's t-test. FIG. 3D, iKIX1 inhibits ketoconazole (KET)-induced transcriptional upregulation of CgCDR1 and CgCDR2 in a CgPDR1 wild-type strain (SFY114). **P<0.005. FIG. 3E. RNA-Seq analysis of a C. glabrata SFY114 (PDR1 wild-type) strain pre-treated with iKIX1 or vehicle alone then induced with ketoconazole (iKIX1+KET and KET, respectively). FIG. 3F, iKIX1 inhibits xenobiotic-induced CgPdr1 transcription in CgPdr1 gain-of-function mutants (amino acid changes indicated). Samples shown were induced with ketoconazole. *P<0.05 and **P<0.01 as compared to DMSO+ketoconazole control. FIG. 3G, iKIX1 inhibits rhodamine 6G efflux in C. glabrata as compared to vehicle control. * P<0.05, **P<0.005 as compared to DMSO+ketoconazole control. Data represent the means of three biological replicates. Two-tailed student's t-test used to determine P values; error bars represent means+/−standard deviation.

FIG. 4A. Schematic showing CgPdr1 gain-of-function alterations in relation to putative functional domains. DBD: DNA-binding domain, ID: inhibitory domain, MHR: middle homology region, AD: activation domain. FIG. 4B, iKIX1 restores the efficacy of azoles towards CgPDR1 gain-of-function mutants. Plates contained increasing concentrations of vehicle control (DMSO) or iKIX1 to 150 µM in the absence or presence of fluconazole (FLU) or ketoconazole (KET). FIG. 4C, iKIX1 in combination with fluconazole but not fluconazole alone significantly extended survival of G. mellonella larvae injected with CgPDR1$^{L280F}$ (SFY115, n=9). For SFY114, n=10. *P<0.05, ***P<0.001 as compared to PBS vehicle control. Statistical differences measured using a log-rank (Mantel-Cox) test. FIG. 4D, iKIX1 combination treatment with 25 mg/kg fluconazole (low FLU) reduces fungal tissue burden in the kidney or spleen of mice injected with CgPDR1 wild-type (SFY114); iKIX1 in combination with 100 mg/kg fluconazole (high FLU) reduces fungal tissue burden in the kidney or spleen of mice injected with CgPDR1$^{L280F}$ (SFY115). N=5 mice for each treatment condition; *P<0.05. P<0.005 and *P<0.0001 as compared to no treatment. Statistical differences measured using a Wilcoxon rank-sum test; error bars represent means+/− standard deviation.

FIG. 5 shows a summary of quality statistics for the ensemble of 10 structures calculated with AMBER explicit water refinement and list of experimental restraints.

FIG. 6. Left: Table of compound libraries that were screened using a fluorescence polarization assay at the Institute of Chemistry & Cell Biology (ICCB) facility at Harvard Medical School. Right: An S. cerevisiae viability screen identifies small molecules that preferentially inhibit growth of S. cerevisiae in a concentration-dependent manner in the presence of 5 µM ketoconazole (KET). Top hits from the screen are shown; OD$_{600}$ values are the average of values from duplicate plates.

FIGS. 9A-D. With iKIX1 pre-treatment, CgPdr1-dependent transcription of (FIG. 9A) CgCDR1 and (FIG. 9B) CgYOR1 remains repressed 120 minutes after ketoconazole induction. SFY114 (PDR1 wild-type) cells were pre-incubated with vehicle (DMSO) or iKIX1 and then induced with 40 µM ketoconazole (+KET). Transcript levels were assessed by quantitative RT-PCR prior to and for 120 minutes following ketoconazole induction. Transcript levels are normalized to CgRDN25-1 and un-induced vehicle control (DMSO) at t=0. FIG. 9C, iKIX1 treatment alone does not have significant effects on CgPdr1 target gene induction either in the presence of wild-type (SFY114) or gain-of-function mutant CgPDR1 (amino acid alterations indicated). FIG. 9D. Table of average CgCDR1 delta Cp values (Cp$_{CgCD1}$-Cp$_{CgRDN25-1}$) and corresponding standard deviation for quantitative real-time PCR experiments. For all panels of FIGS. 9A-9D, average value of three biological replicates is shown and error bars represent+/−standard deviation; *P<0.05, p<0.01, and *p<0.005 as compared to vehicle+ketoconazole control. P values calculated using two-tailed Student's t-test.

FIGS. 11C and 11D. The EUCAST broth microdilution method[27] was used to assess the effects of iKIX1 and ketoconazole combination treatment. Growth, as assessed by OD$_{540}$, was normalized to no drug control. All combination indices (CI) for the CgPDR1$^{L280F}$ mutant were less than 1, indicating synergy. A representative of three biological replicates is shown and the red line indicates a combination index of 1.

FIGS. 12A-12H show electron-withdrawing groups in the aromatic ring of iKIX1 complement the basic binding interface of the CgGal11A KIX domain and thus play a key role in iKIX1 function. A iKIX1 analog (A2) lacking electron-withdrawing groups increases the IC$_{50}$ in the FP assay (FIG. 12A) and abolishes activity in the S. cerevisiae luciferase reporter assay (FIG. 12B), repression of CgCDR1 expression (FIG. 12C), and synergistic C. glabrata cell growth inhibition with azole antifungal agents (FIG. 12D). Error bars in FIGS. 12B and 12C indicate mean+/−s.d. of technical replicates (reads/real-time PCR reactions, respectively).

**P<0.005; statistical differences calculated using two-tailed Student's t-test. FIG. 12E, iKIX1 inhibits viability of HepG2 cells at concentrations>50 µM. The mean of 3 biological replicates is shown; error bars represent means+/−s.d. FIG. 12F, iKIX1 exhibits no effect on transcription of SREBP-target genes in HepG2 cells at concentrations up to 100 µM. Biological duplicates were assessed; representative experiment is shown and error bars represent means+/−s.d. of technical (real-time PCR) replicates. FIG. 12G. Mouse plasma stability of iKIX1 and mouse and human microsomal stability of iKIX1, n=1. FIG. 12H. In vivo pharmacokinetic parameters of iKIX1, n=3 mice per time point.

FIGS. 13A-13F. Statistical differences were measured using a Mann-Whitney/Wilcoxon rank-sum test as compared to no treatment control; error bars represent means+/−standard deviation.

FIGS. 15-18. Top Row. Compound names and structures. Second Row. Spot plating. Candida glabrata PDR1 gain-of-function mutants are sensitive to 200 µM fluconazole in the presence of compound gradients. Plates with compound gradients from approximately 0 to 150 µM are shown on top, plates with compound gradients from approximately 0 to 150 µM in the presence of 200 µM fluconazole (+FLU) are below. Isogenic Candida glabrata PDR1 gain-of-function mutants used in the assays are as follows: L280F-CgPDR1$^{L280F}$ (SFY115), R376W-CgPDR1$^{R376W}$ (SFY101), T588A-CgPDR1$^{T588A}$ (105), Y584C-CgPDR1$^{Y584C}$ (SFY111), D1082G-CgPDR1$^{D1082G}$ (SFY103). Spot plating methods: Strains were inoculated and grown in YPD at 30° C. with shaking overnight and 5 mL of YPD was inoculated with 20 µL of overnight culture. Strains were grown to log phase at 30° C. with shaking and then diluted to an OD$_{600}$ of 0.0004, 3 µL of cell suspension was spotted on plates containing gradients with increasing concentration of compound and a fixed concentration of fluconazole, as indicated. Plates were incubated at 30° C. and growth was assessed after 48 hours. Third Row. Luciferase assays. Compounds reduce azole-induced PDRE-dependent luciferase gene transcription to a similar degree as iKIX1. Y-axis represents luciferase activity, normalized to vehicle (DMSO)+ketoconazole control. Strains were incubated with 5 µM or 50 µM compound in the presence of 40 µM ketoconazole (KET). Luciferase assay methods: An S. cerevisiae pdr1Δ::KANpdr3Δ::KAN strain bearing plasmids carrying CgPDR1-1 and PDRES-luciferase was used for the luciferase assays. Strains were grown overnight in YPD and then washed twice with sterilized Milli-Q water before being resuspended to an OD600 of 0.8 in YP. After 20 hours, cultures were split and iKIX1 or DMSO alone was added to final concentrations as indicated. At the same time, ketoconazole to a final concentration of 40 µM (resuspended in ethanol) or ethanol alone (vehicle) were added to cultures. After 24 hours of treatment, an equal volume of 1 mM d-luciferin (sodium salt) in 0.1 M sodium citrate buffer at pH 5.0 was added to 100 µL aliquots. Luminescent signal was acquired over 10 seconds and RLU (relative light units) presented are normalized to growth (assessed by OD$_{600}$)) and untreated controls. Fourth Row. Compounds reduce azole-induced transcription of CgPdr1 target CgCDR1 in a strain bearing wild-type CgPDR1 (SFY114) to a similar degree as iKIX1. Y-axis represents CDR1 transcription, normalized to vehicle (DMSO)+ketoconazole control. Strains were pre-incubated with 30 µM compound before being induced with 40 µM keotconazole (KET) for 15' prior to harvest. Transcription assays and quantitative real-time PCR methods: Cells were grown in YPD at 30° C. with shaking 24 hours then washed twice in 2× volume of Milli-Q water before being resuspended in YP to an OD$_{600}$ of 0.8. Cells were grown with shaking overnight (~16 hours) before splitting and treatment with vehicle (DMSO) or iKIX1 to concentrations indicated. Cells were grown with shaking another 8 hours before harvest of non-azole induced samples. Remaining cultures were induced to a final concentration of 40 µM ketoconazole and harvested after 15 minutes and subsequent time points, if shown. For harvest and preparation of RNA, cells equivalent to an OD$_{600}$ of 0.4 were centrifuged at 4,000 rpm for 4 minutes and then resuspended in 700 µL Trizol. Cells in Trizol were bead beat with 0.4 mL glass beads for 2×30 seconds and then protocol was followed according to manufacturer's instructions. One µg of RNA was used for DNase I treatment (Roche) and subsequent cDNA synthesis using Roche Transcriptor First Strand cDNA synthesis kit. cDNA was diluted 5× in water and 2.5 µL was used per reaction with Roche SYBR green. Quantitative real-time PCR reactions were run and analyzed on a Roche LightCycler 480 system. Sc transcripts were normalized to ScSCR1 and untreated, uninduced DMSO control; Cg transcripts were normalized to CgRDN25-1 and untreated, uninduced DMSO control.

DETAILED DESCRIPTION OF CERTAIN EMBODIMENTS

Figure 1A:
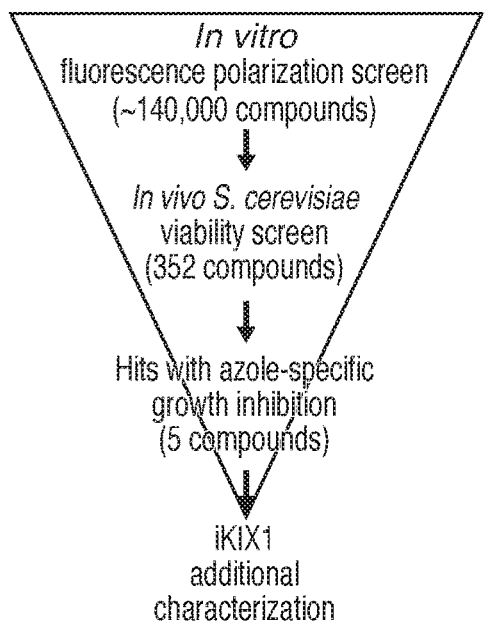
FIGS. 1A-ID show the discovery of inhibitors of the CgGal11A KIX-CgPdr1AD interaction interface.

Provided herein are compounds (e.g., Compounds of Formula (I). (II), and (III)), and pharmaceutically acceptable salts, hydrates, solvates, polymorphs, co-crystals, tautomers, stereoisomers, isotopically labeled derivatives, and prodrugs thereof, and pharmaceutical compositions thereof. In certain embodiments, the compounds are inhibitors of the interaction of the *C. glabrata* Pdr1 activation domain with the *C. glabrata* Gal11A KIX domain. The compounds can therefore be used for treating diseases (e.g., infectious diseases) and/or for killing or inhibiting the growth of pathogens (e.g., fungi). In certain embodiments, for example, the compounds inhibit Pdr1-dependent gene activation and re-sensitize drug-resistant fungi (e.g., *C. glabrata*) to antifungals (e.g., azole antifungals). In another aspect, the present invention provides kits comprising the compounds or pharmaceutical compositions provided herein.

Compounds

Provided herein are compounds of Formula (I):

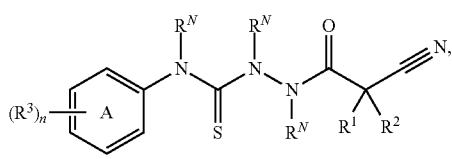

and pharmaceutically acceptable salts, hydrates, solvates, polymorphs, co-crystals, tautomers, stereoisomers, isotopically labeled derivatives, and prodrugs thereof, wherein:

$R^1$ and $R^2$ are independently hydrogen, optionally substituted alkyl, optionally substituted alkenyl, optionally substituted alkynyl, optionally substituted aryl, optionally substituted carbocyclyl, optionally substituted heterocyclyl, or optionally substituted heteroaryl; or optionally $R^1$ and $R^2$ are joined together with the intervening atoms to form optionally substituted carbocyclyl or optionally substituted heterocyclyl;

each instance of $R^N$ is hydrogen, optionally substituted alkyl, or optionally substituted acyl, or a nitrogen protecting group;

each instance of $R^3$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —OR$^{3a}$, —N(R$^{3b}$)$_2$, or —SR$^3$; or optionally two $R^3$ are joined together with the intervening atoms to form optionally substituted carbocyclyl or optionally substituted heterocyclyl;

each instance of $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and n is 1, 2, 3, 4, or 5.

In certain embodiments, a compound of the invention is not one of the following:

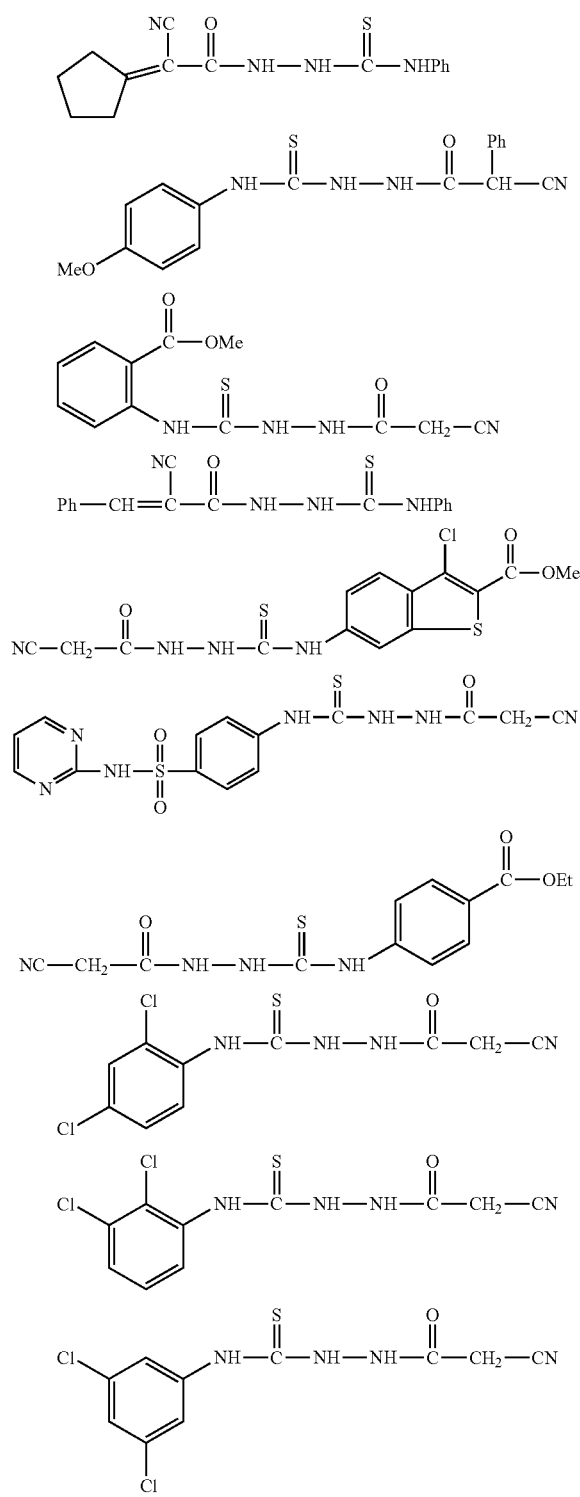

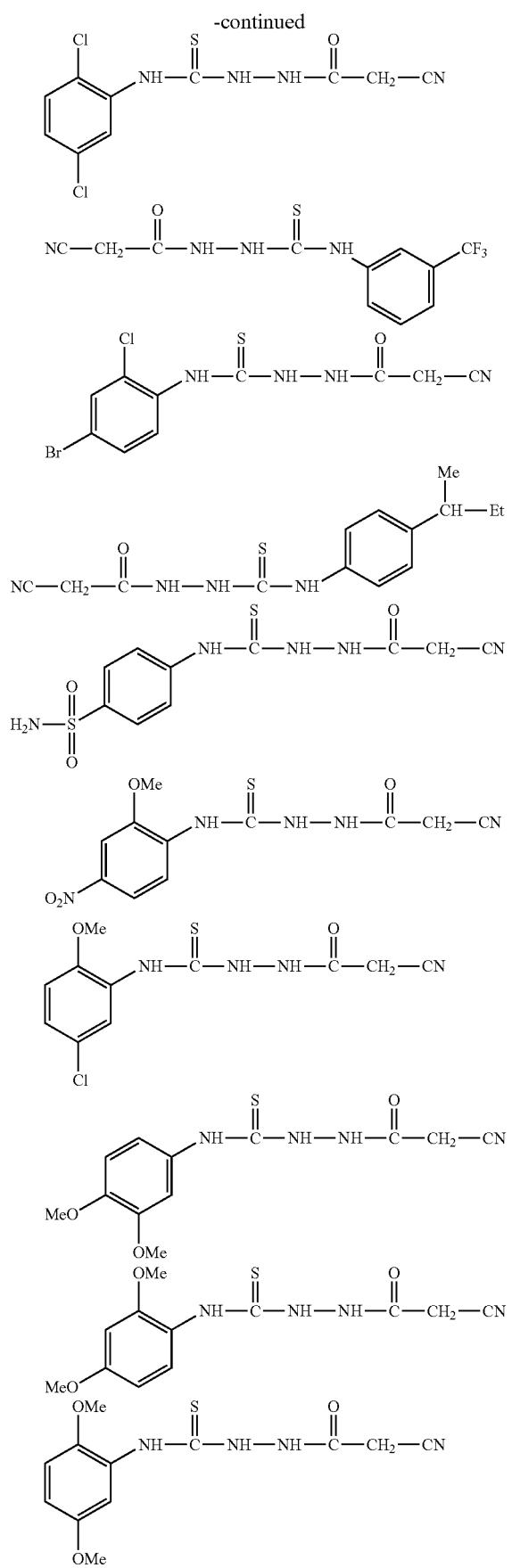
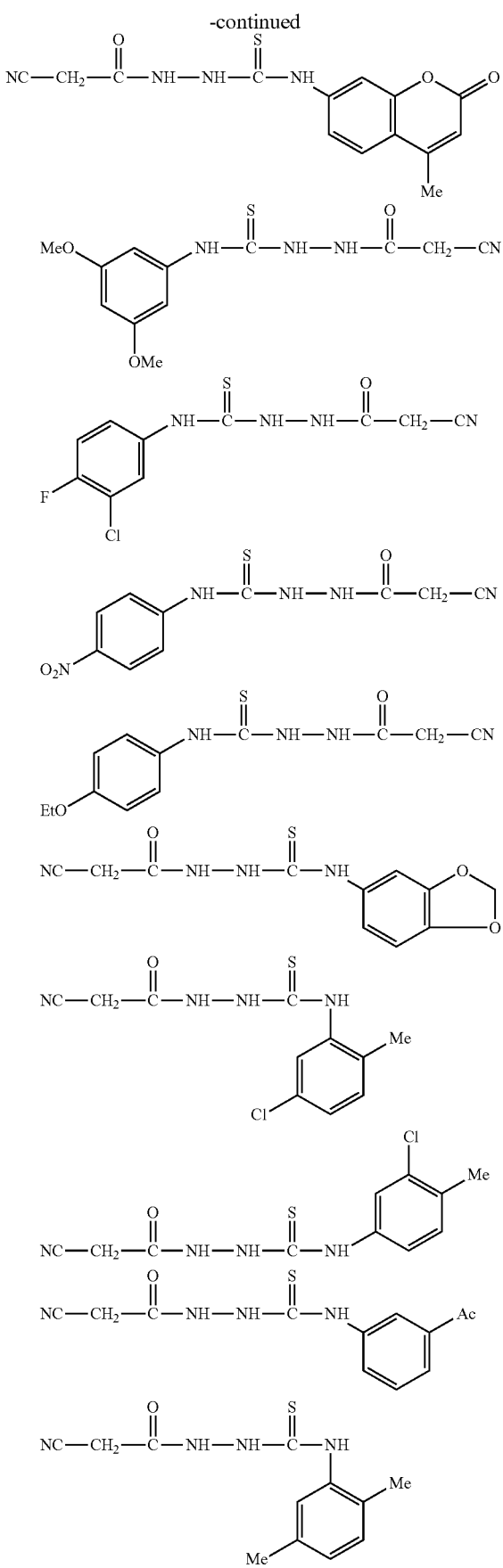

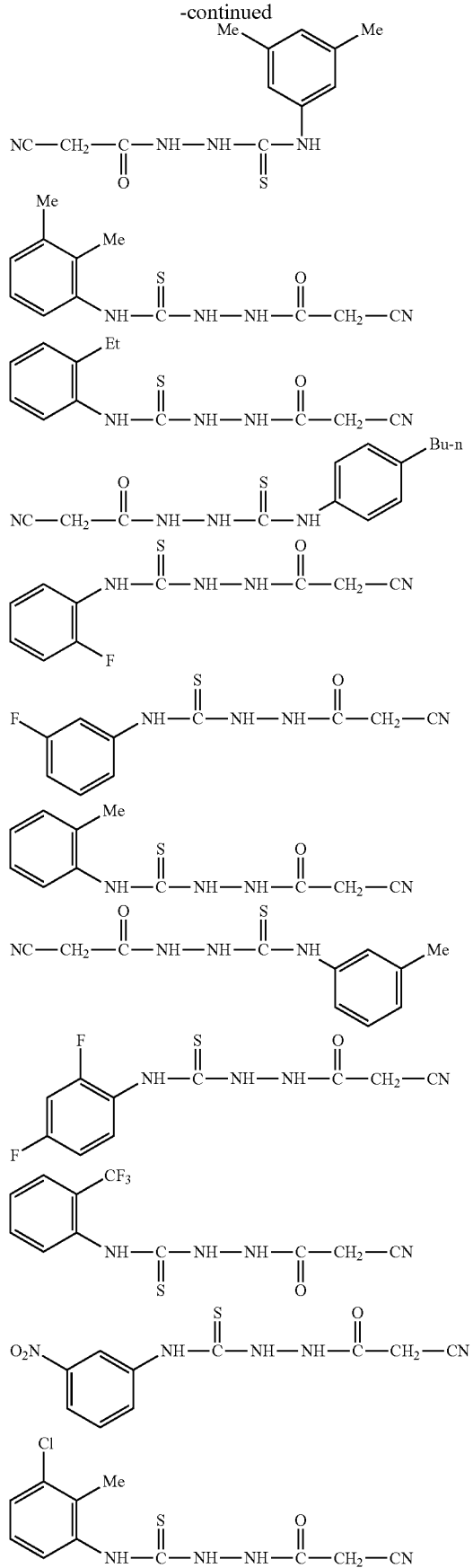
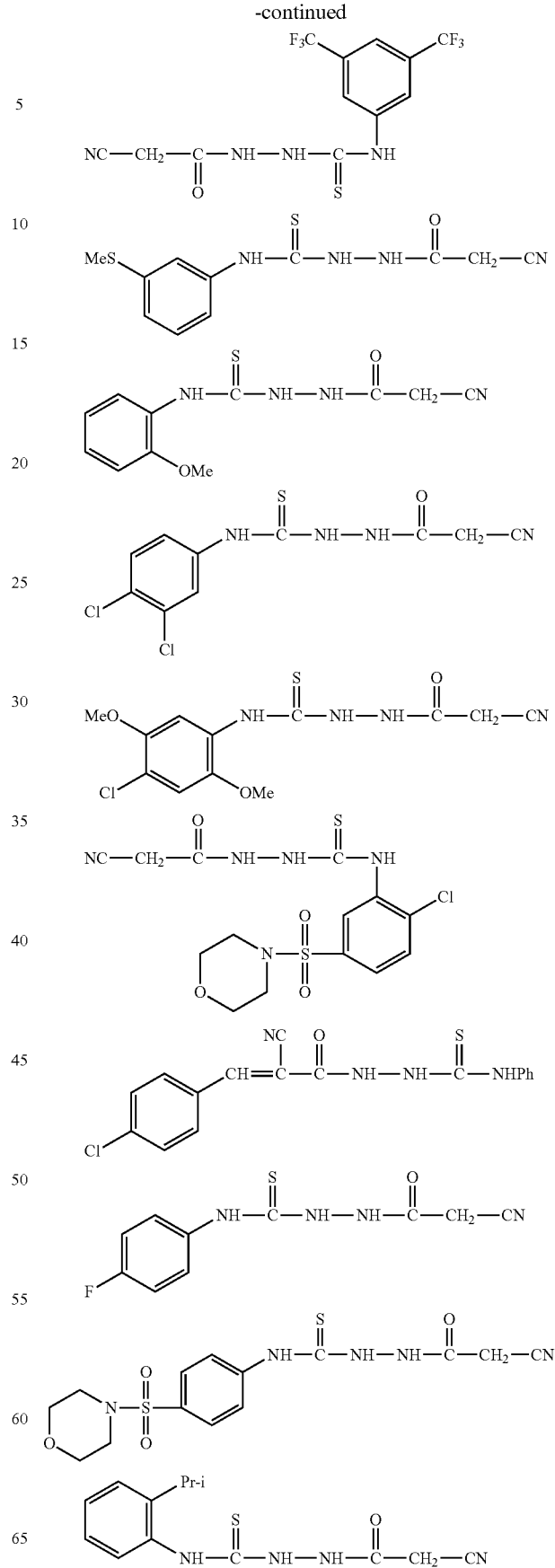

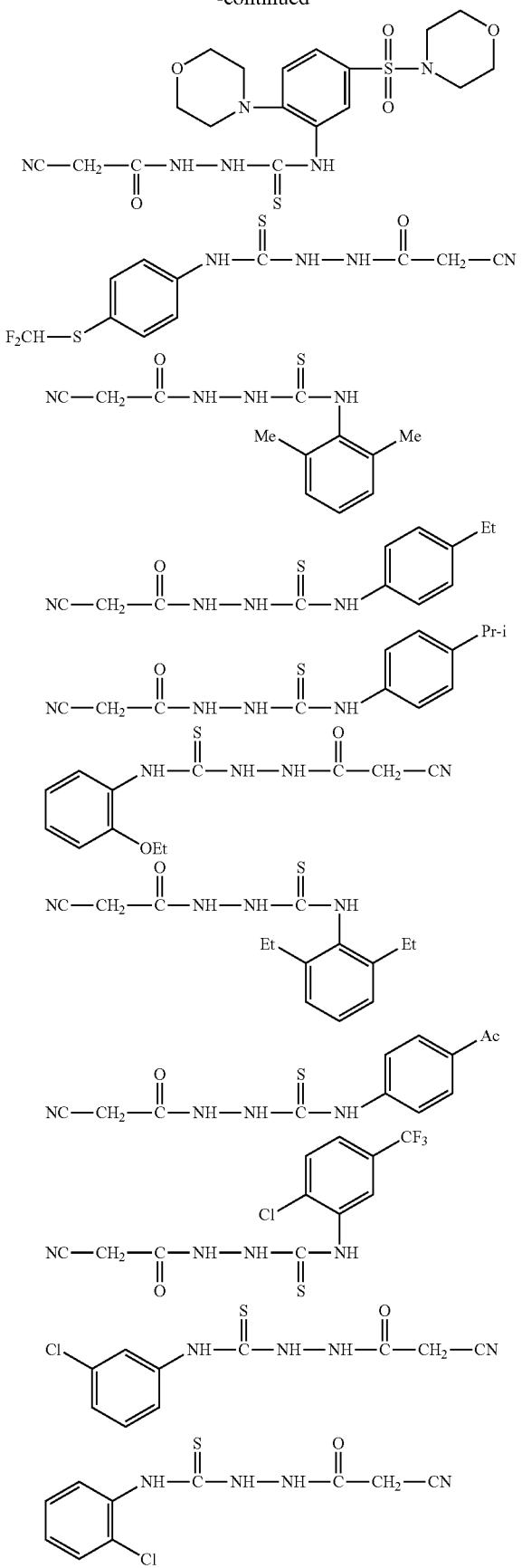
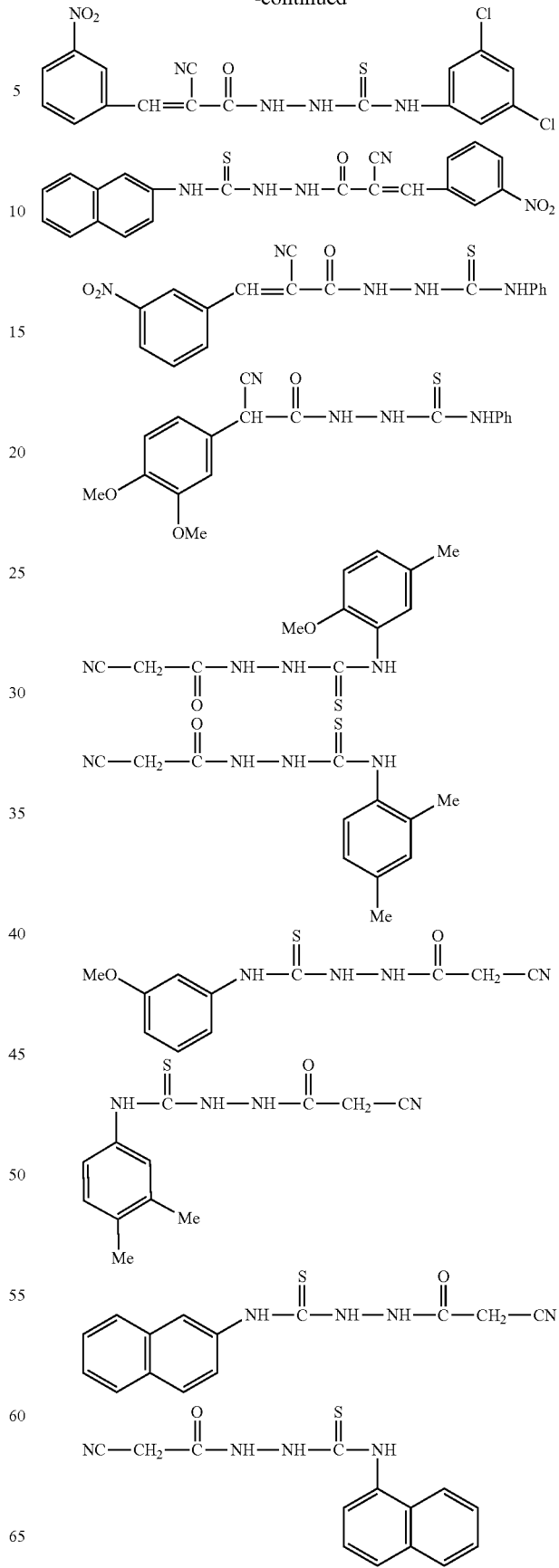

-continued

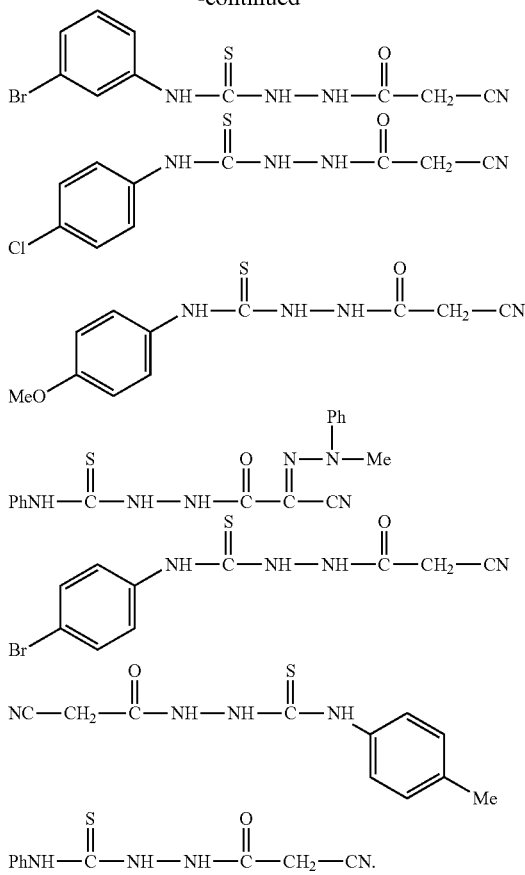

In certain embodiments, the compound of Formula (I) is of Formula (I-a):

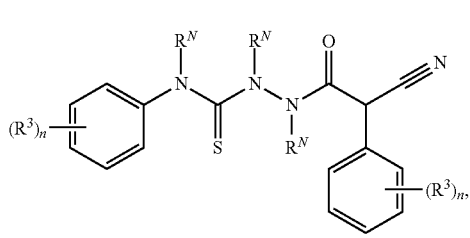
(I-a)

or a pharmaceutically acceptable salt, hydrate, solvate, polymorph, co-crystal, tautomer, stereoisomer, isotopically labeled derivative, or prodrug thereof, wherein:
each instance of n is independently 0, 1, 2, 3, 4, or 5.

In certain embodiments, the compound of Formula (I) is of the following formula:

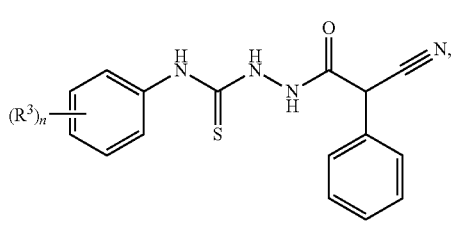

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

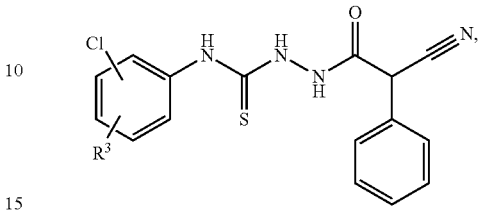

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following

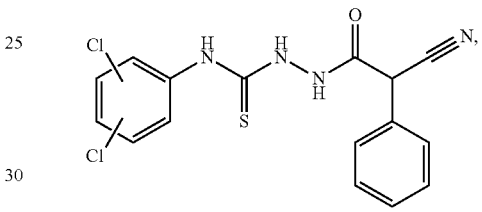

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

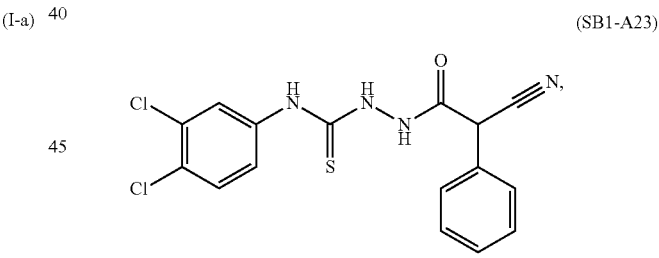
(SB1-A23)

or a pharmaceutically acceptable salt, hydrate, solvate, polymorph, co-crystal, tautomer, stereoisomer, isotopically labeled derivative, or prodrug thereof.

Also provided herein are compounds of Formula (II):

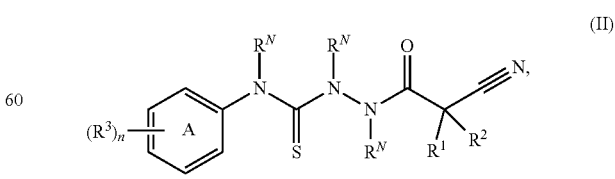
(II)

and pharmaceutically acceptable salts, hydrates, solvates, polymorphs, co-crystals, tautomers, stereoisomers, isotopically labeled derivatives, and prodrugs thereof, wherein:

$R^1$ and $R^2$ are independently hydrogen, halogen, or optionally substituted alkyl, or optionally $R^1$ and $R^2$ are joined together with the intervening atoms to form optionally substituted carbocyclyl or optionally substituted heterocyclyl;

provided that at least one of $R^1$ and $R^2$ is not hydrogen;

each instance of $R^N$ is hydrogen, optionally substituted alkyl, or optionally substituted acyl, or a nitrogen protecting group;

each instance of $R^3$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —OR$^{3a}$, —N(R$^{3b}$)$_2$, or —SR$^{3c}$; or optionally two $R^3$ are joined together with the intervening atoms to form optionally substituted carbocyclyl or optionally substituted heterocyclyl;

each instance of $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and n is 1, 2, 3, 4, or 5.

In certain embodiments. $R^1$ and $R^2$ are independently hydrogen or optionally substituted alkyl; or optionally $R^1$ and $R^2$ are joined together with the intervening atoms to form optionally substituted carbocyclyl or optionally substituted heterocyclyl; provided that at least one of $R^1$ and $R^2$ is not hydrogen.

In certain embodiments, the compound of Formula (II) is of Formula (II-a):

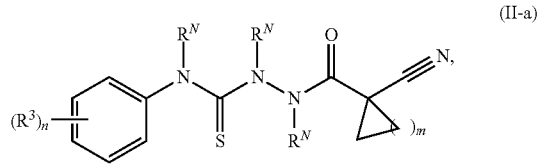

(II-a)

or a pharmaceutically acceptable salt, hydrate, solvate, polymorph, co-crystal, tautomer, stereoisomer, isotopically labeled derivative, or prodrug thereof, wherein:

m is 1, 2, 3, or 4.

As generally defined herein, m is 1, 2, 3, or 4. In certain embodiments, m is 1. In certain embodiments, m is 2. In certain embodiments, m is 3. In certain embodiments, m is 4.

In certain embodiments, the compound of Formula (II) is of one of the following formulae:

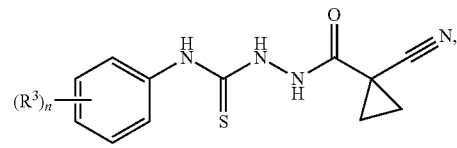

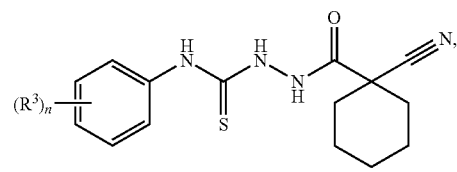

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following

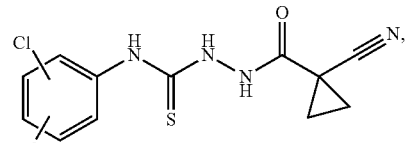

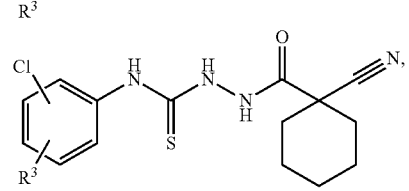

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

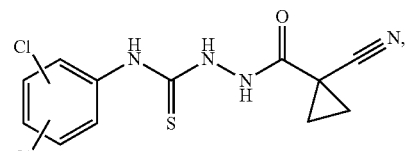

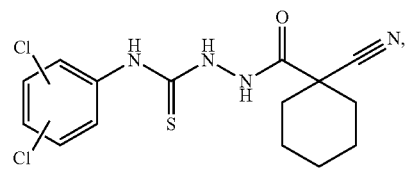

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

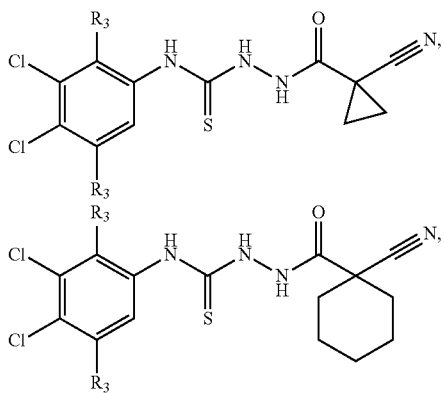

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

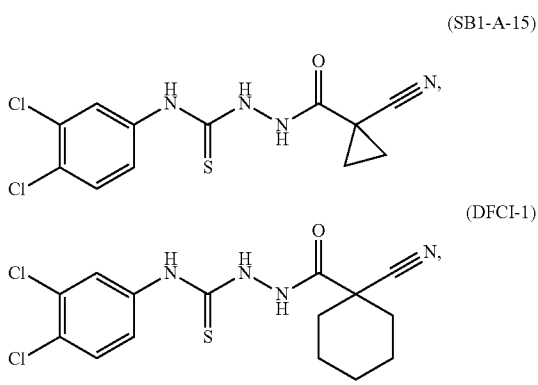

or a pharmaceutically acceptable salt, hydrate, solvate, polymorph, co-crystal, tautomer, stereoisomer, isotopically labeled derivative, or prodrug thereof.

Also provided herein are compounds of Formula (III):

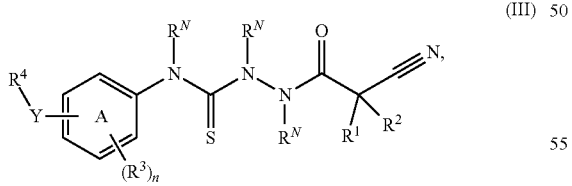

(III)

and pharmaceutically acceptable salts, hydrates, solvates, polymorphs, co-crystals, tautomers, stereoisomers, isotopically labeled derivatives, and prodrugs thereof, wherein:

Y is a bond, optionally substituted alkylene, —O—, —NR$^N$—, or —S—;

R$^1$ and R$^2$ are independently hydrogen, optionally substituted alkyl, optionally substituted alkenyl, optionally substituted alkynyl, optionally substituted aryl, optionally substituted carbocyclyl, optionally substituted heterocyclyl, or optionally substituted heteroaryl; or optionally R$^1$ and R$^2$ are joined together with the intervening atoms to form optionally substituted carbocyclyl or optionally substituted heterocyclyl;

each instance of R$^N$ is hydrogen, optionally substituted alkyl, or optionally substituted acyl, or a nitrogen protecting group;

each instance of R$^3$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —OR$^{3a}$, —N(R$^{3b}$)$_2$, or —SR$^3$; or optionally two R$^3$ are joined together with the intervening atoms to form optionally substituted carbocyclyl or optionally substituted heterocyclyl;

each instance of R$^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of R$^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two R$^{3b}$ are joined together with the intervening atoms to form optionally substituted heterocyclyl or optionally substituted heteroaryl;

each instance of R$^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

R$^4$ is optionally substituted carbocyclyl, optionally substituted heterocyclyl, optionally substituted aryl, or optionally substituted heteroaryl; and n is 1, 2, 3, or 4.

In certain embodiments, the compound of Formula (III) is of the following formula:

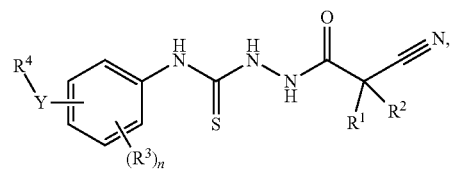

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of one of the following formulae:

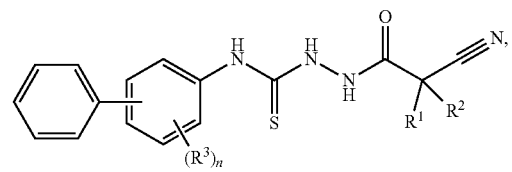

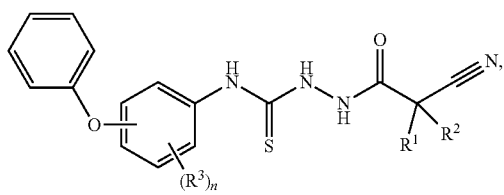

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of one of the following formulae:

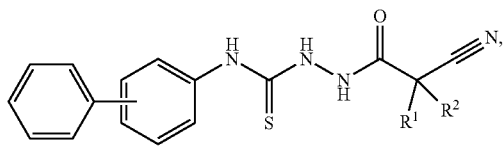

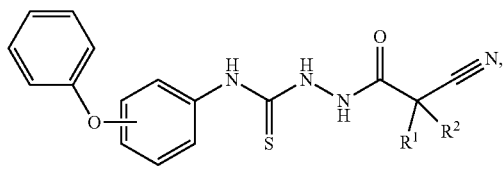

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of one of the following formulae:

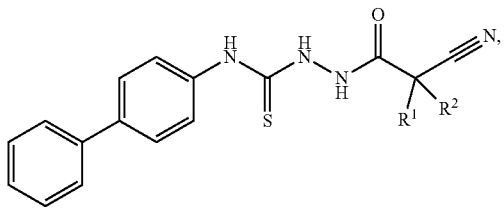

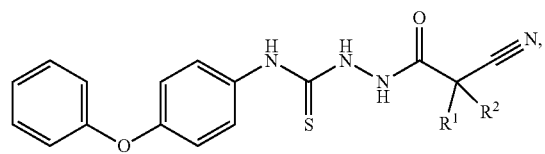

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of one of the following formulae:

(SB1-A04)

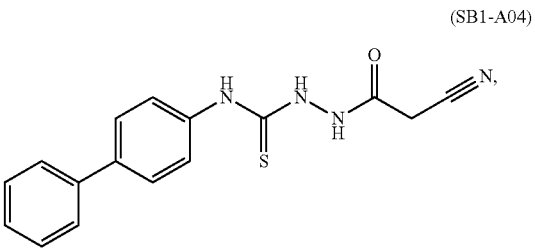

(SB1-A09)

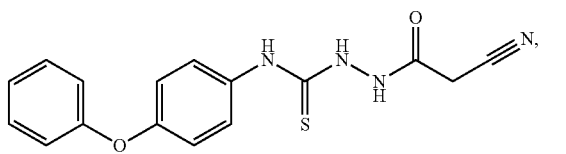

or a pharmaceutically acceptable salt, hydrate, solvate, polymorph, co-crystal, tautomer, stereoisomer, isotopically labeled derivative, or prodrug thereof.

Also provided herein are compounds of one of the following formulae:

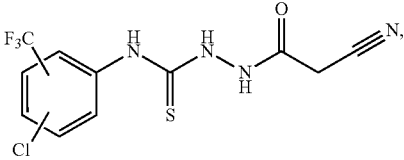

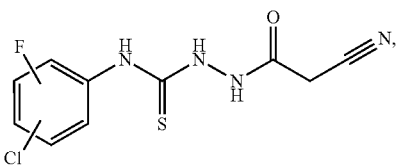

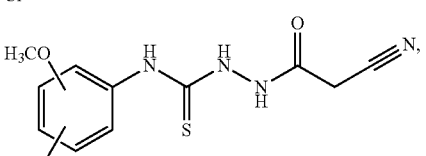

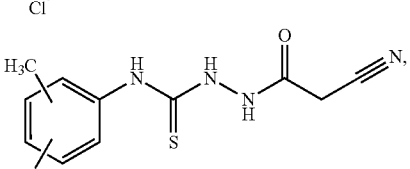

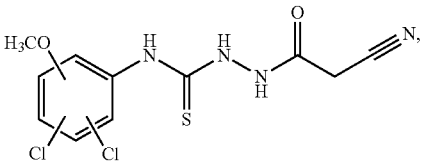

and pharmaceutically acceptable salts, hydrates, solvates, polymorphs, co-crystals, tautomers, stereoisomers, isotopically labeled derivatives, or prodrugs thereof.

In certain embodiments, the compound is selected from the group consisting of:

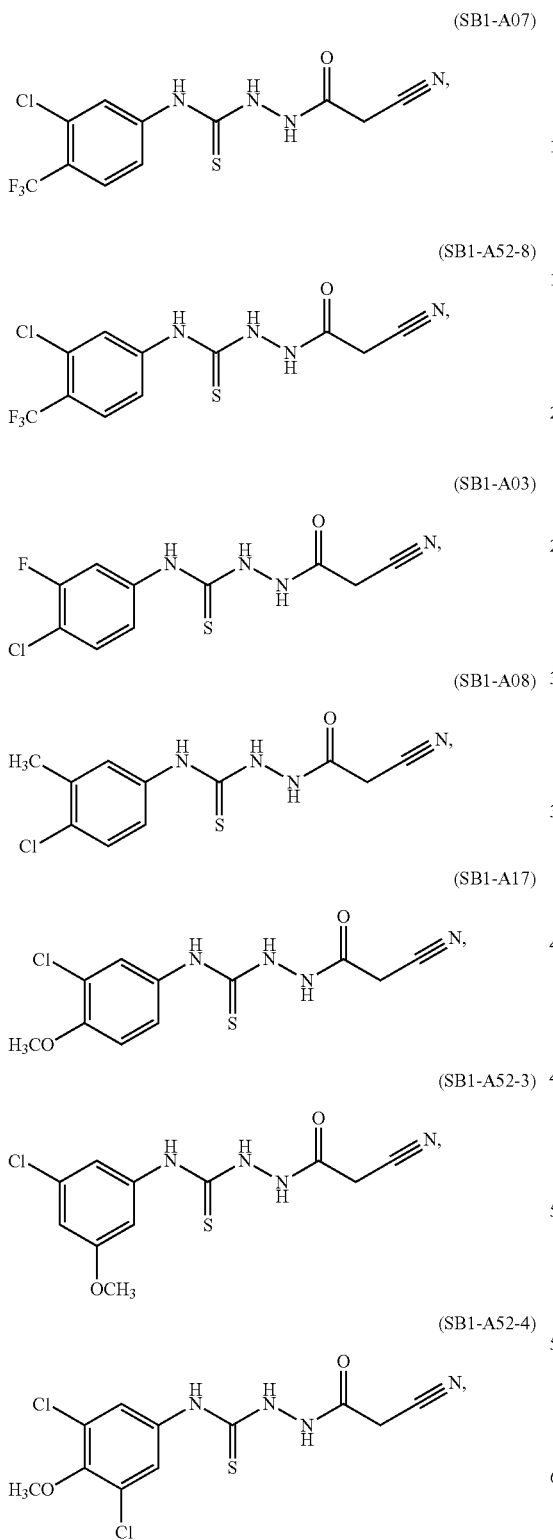

and pharmaceutically acceptable salts, hydrates, solvates, polymorphs, co-crystals, tautomers, stereoisomers, isotopically labeled derivatives, and prodrugs thereof.

As generally defined herein, $R^1$ is hydrogen, optionally substituted alkyl, optionally substituted alkenyl, optionally substituted alkynyl, optionally substituted aryl, optionally substituted carbocyclyl, optionally substituted heterocyclyl, or optionally substituted heteroaryl. In certain embodiments, $R^1$ is hydrogen. In certain embodiments, $R^1$ is optionally substituted alkyl. In certain embodiments, $R^1$ is optionally substituted alkenyl. In certain embodiments, $R^1$ is optionally substituted alkynyl. In certain embodiments, $R^1$ is optionally substituted aryl. In certain embodiments, $R^1$ is optionally substituted carbocyclyl. In certain embodiments, $R^1$ is optionally substituted heterocyclyl. In certain embodiments, $R^1$ is optionally substituted heteroaryl.

As generally defined herein, $R^2$ is hydrogen, optionally substituted alkyl, optionally substituted alkenyl, optionally substituted alkynyl, optionally substituted aryl, optionally substituted carbocyclyl, optionally substituted heterocyclyl, or optionally substituted heteroaryl. In certain embodiments, $R^2$ is hydrogen. In certain embodiments, $R^1$ is optionally substituted alkyl. In certain embodiments, $R^2$ is optionally substituted alkenyl. In certain embodiments, $R^2$ is optionally substituted alkynyl. In certain embodiments, $R^2$ is optionally substituted aryl. In certain embodiments, $R^2$ is optionally substituted carbocyclyl. In certain embodiments, $R^2$ is optionally substituted heterocyclyl. In certain embodiments, $R^2$ is optionally substituted heteroaryl.

In certain embodiments, at last one of $R^1$ and $R^2$ is not hydrogen. In certain embodiments, both $R^1$ and $R^2$ are not hydrogen.

In certain embodiments, $R^1$ and $R^2$ are joined together with the intervening atoms to form optionally substituted carbocyclyl or optionally substituted heterocyclyl. In certain embodiments, $R^1$ and $R^2$ are joined together with the intervening atoms to form optionally substituted carbocyclyl. In certain embodiments, $R^1$ and $R^2$ are joined together with the intervening atoms to form optionally substituted heterocyclyl. In certain embodiments, $R^1$ and $R^2$ are joined together with the intervening atoms to form optionally substituted cyclopropyl. In certain embodiments, $R^1$ and $R^2$ are joined together with the intervening atoms to form optionally substituted cyclobutyl. In certain embodiments, $R^1$ and $R^2$ are joined together with the intervening atoms to form optionally substituted cyclopentyl. In certain embodiments, $R^1$ and $R^2$ are joined together with the intervening atoms to form optionally substituted cyclohexyl. In certain embodiments, $R^1$ and $R^2$ are joined together with the intervening atoms to form:

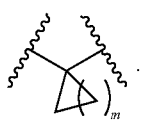

In certain embodiments, $R^1$ and $R^2$ are joined together with the intervening atoms to form:

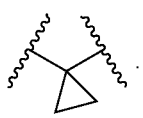

In certain embodiments, $R^1$ and $R^2$ are joined together with the intervening atoms to form:

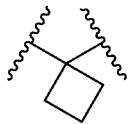

In certain embodiments, $R^1$ and $R^2$ are joined together with the intervening atoms to form:

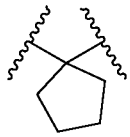

In certain embodiments, $R^1$ and $R^2$ are joined together with the intervening atoms to form:

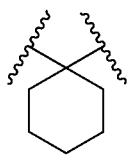

In certain embodiments, at least one of $R^1$ and $R^2$ is optionally substituted phenyl. In certain embodiments, at least one of $R^1$ and $R^2$ is unsubstituted phenyl. In certain embodiments, $R^1$ is phenyl and $R^2$ is hydrogen.

In certain embodiments, at least one of $R^1$ and $R^2$ is halogen (e.g., —Cl, —Br, —I, —F). In certain embodiments, both $R^1$ and $R^2$ are independently halogen. In certain embodiments, $R^1$ and $R^2$ are independently hydrogen or $C_{1-4}$ alkyl; provided that at least one of $R^1$ and $R^2$ is not hydrogen. In certain embodiments. $R^1$ and $R^2$ are independently selected from the group consisting of hydrogen, methyl, ethyl, n-propyl, iso-propyl, n-butyl, iso-butyl, and sec-butyl, each of which is unsubstituted; provided that at least one of $R^1$ and $R^2$ is not hydrogen. In certain embodiments, $R^1$ and $R^2$ are both independently selected from the group consisting of methyl, ethyl, n-propyl, iso-propyl, n-butyl, iso-butyl, and sec-butyl, each of which is unsubstituted. In certain embodiments, $R^1$ and $R^2$ are both unsubstituted methyl.

As generally defined herein, each instance of $R^3$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —OR$^3$, —N(R$^{3b}$)$_2$, or SR$^3$; or optionally two $R^3$ are joined together with the intervening atoms to form optionally substituted carbocyclyl or optionally substituted heterocyclyl. In certain embodiments, at least one instance of $R^3$ is hydrogen. In certain embodiments, at least one instance of $R^3$ is halogen. In certain embodiments, at least one instance of $R^3$ is —CN. In certain embodiments, at least one instance of $R^3$ is —SCN. In certain embodiments, at least one instance of $R^3$ is —NO$_2$. In certain embodiments, at least one instance of $R^3$ is —N$_3$. In certain embodiments, at least one instance of $R^3$ is optionally substituted alkyl. In certain embodiments, at least one instance of $R^3$ is optionally substituted alkenyl. In certain embodiments, at least one instance of $R^3$ is optionally substituted alkynyl. In certain embodiments, at least one instance of $R^3$ is optionally substituted carbocyclyl. In certain embodiments, at least one instance of $R^3$ is optionally substituted heterocyclyl. In certain embodiments, at least one instance of $R^3$ is optionally substituted aryl. In certain embodiments, at least one instance of $R^3$ is optionally substituted heteroaryl. In certain embodiments, at least one instance of $R^3$ is optionally substituted acyl. In certain embodiments, at least one instance of $R^3$ is optionally substituted sulfinyl. In certain embodiments, at least one instance of $R^3$ is optionally substituted sulfonyl. In certain embodiments, at least one instance of $R^3$ is —OR$^{3a}$. In certain embodiments, at least one instance of $R^3$ is —N(R$^{3b}$)$_2$. In certain embodiments, at least one instance of $R^3$ is —SR$^{3c}$. In certain embodiments, two $R^3$ are joined together with the intervening atoms to form optionally substituted carbocyclyl or optionally substituted heterocyclyl.

In certain embodiments, at least one instance of $R^3$ is halogen (e.g., —Cl, —Br, —I, —F). In certain embodiments, at least one instance of $R^3$ is —Cl. In certain embodiments, at least one instance of $R^3$ is —I. In certain embodiments, at least one instance of $R^3$ is —Br. In certain embodiments, at least one instance of $R^3$ is —F.

In certain embodiments, at least one instance of $R^3$ is optionally substituted alkyl. In certain embodiments, at least one instance of $R^3$ is haloalkyl. In certain embodiments, at least one instance of $R^3$ is trihalomethyl. In certain embodiments, at least one instance of $R^3$ is trifluoromethyl (—CF$_3$). In certain embodiments, at least one instance of $R^3$ is optionally substituted $C_{1-6}$ alkyl. In certain embodiments, at least one instance of $R^3$ is optionally substituted $C_{1-3}$ alkyl. In certain embodiments, at least one instance of $R^3$ is unsubstituted $C_{1-3}$ alkyl. In certain embodiments, at least one instance of $R^1$ is selected from the group consisting of methyl, ethyl, n-propyl, iso-propyl, n-butyl, iso-butyl, and sec-butyl. In certain embodiments, at least one instance of $R^3$ is methyl.

In certain embodiments, at least one instance of $R^3$ is —OR$^{3a}$. In certain embodiments, at least one instance of $R^3$ is —O—$C_{1-6}$ alkyl. In certain embodiments, at least one instance of $R^3$ is —O—$C_{1-3}$ alkyl. In certain embodiments, at least one instance of $R^3$ is —OCH$_3$. In certain embodiments, at least one instance of $R^3$ is —O-Ph.

In certain embodiments, at least one instance of $R^3$ is optionally substituted phenyl. In certain embodiments, at least one instance of $R^3$ is unsubstituted phenyl.

In certain embodiments, at least one instance of $R^3$ is an electron-withdrawing group. In certain embodiments, at least two instances of $R^3$ are electron-withdrawing groups. In certain embodiments, at least one instance of $R^3$ is selected from the group consisting of halogen, optionally substituted acyl, optionally substituted sulfinyl, optionally substituted sulfonyl, and haloalkyl. In certain embodiments, at least one instance of $R^3$ is selected from the group consisting of halogen, optionally substituted acyl, and haloalkyl. In certain embodiments, at least two instances of $R^3$ are selected from the group consisting of halogen, optionally substituted acyl, optionally substituted sulfinyl, optionally substituted sulfonyl, and haloalkyl. In certain embodiments, at least two instances of $R^3$ are —F, —Cl, —Br, or —I. In certain embodiments, at least two instances of $R^1$ are —Cl. In certain embodiments, one instance of $R^3$ is —Cl, and another instance of $R^3$ is —F. In certain embodiments, one instance of $R^3$ is —Cl, and another instance of $R^3$ is —CF$_3$. In certain embodiments, one instance of $R^3$ is —Cl, and another instance of $R^3$ is methyl. In certain embodiments, one instance of $R^3$ is —Cl, and another instance of $R^3$ is —OCH$_3$.

As generally defined herein, each instance of $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group.

As generally defined herein, each instance of $R^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl.

As generally defined herein, each instance of $R^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

As generally defined herein, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

In certain embodiments, Ring A is of one of the following formulae:

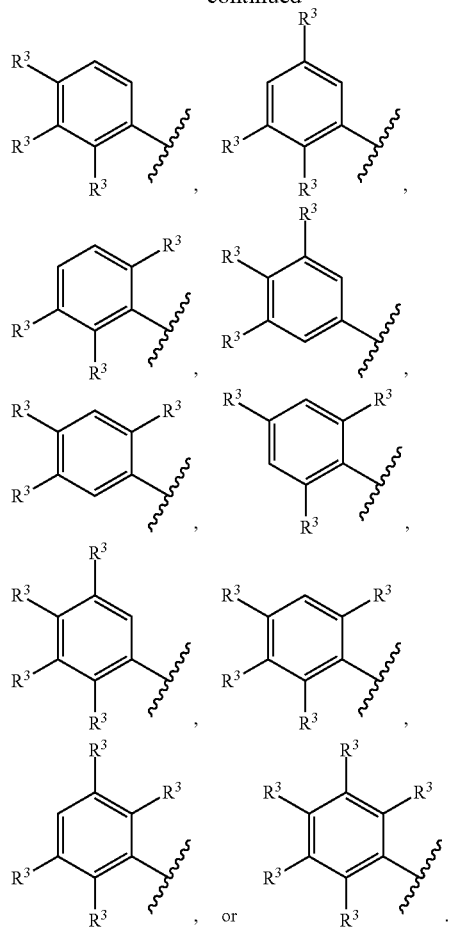

In certain embodiments, Ring A is of one of the following formulae:

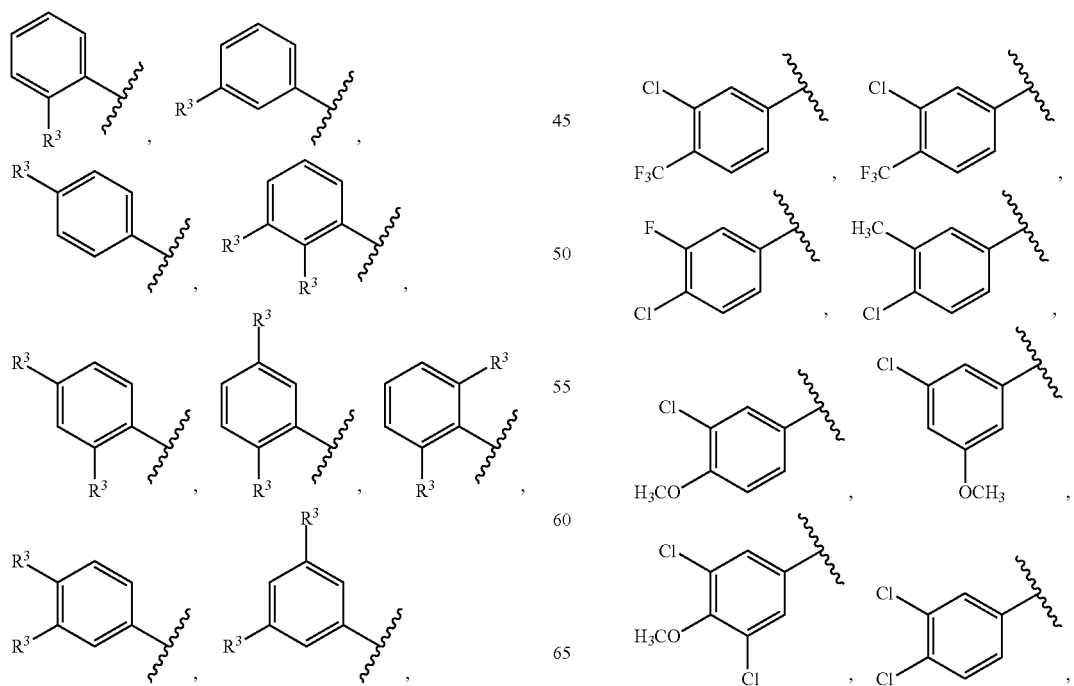

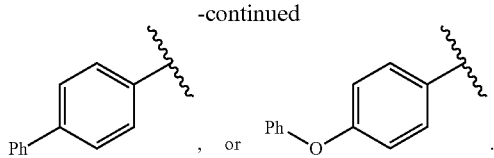

As generally defined herein, Y is a bond, optionally substituted alkylene, —O—, —NR$^N$—, or —S—. In certain embodiments, Y is a bond. In certain embodiments, Y is optionally substituted alkylene. In certain embodiments, Y is —O—. In certain embodiments, Y is —NR$^N$—. In certain embodiments, Y is —S—.

As generally defined herein, R$^4$ is optionally substituted carbocyclyl, optionally substituted heterocyclyl, optionally substituted aryl, or optionally substituted heteroaryl. In certain embodiments, R$^4$ is optionally substituted carbocyclyl. In certain embodiments, R$^4$ is optionally substituted heterocyclyl. In certain embodiments, R$^4$ is optionally substituted aryl. In certain embodiments, R$^4$ is or optionally substituted heteroaryl. In certain embodiments. R$^4$ is optionally substituted phenyl. In certain embodiments, R$^4$ is unsubstituted phenyl.

As generally defined herein, each instance of R$^N$ is hydrogen, optionally substituted alkyl, or optionally substituted acyl, or a nitrogen protecting group. In certain embodiments, at least one instance of R$^N$ is hydrogen. In certain embodiments, at least one instance of R$^N$ is optionally substituted alkyl. In certain embodiments, at least one instance of R$^N$ is optionally substituted acyl. In certain embodiments, at least one instance of R$^N$ is a nitrogen protecting group. In certain embodiments, each R$^N$ is hydrogen.

Pharmaceutical Compositions, Kits, Administration, Methods of Use, and Uses

Provided herein are pharmaceutical compositions comprising a compound provided herein (e.g., a compound of Formula (I), (II), or (III)), or a pharmaceutically acceptable salt, hydrate, solvate, polymorph, co-crystal, tautomer, stereoisomer, isotopically labeled derivative, or prodrug thereof, and a pharmaceutically acceptable carrier or excipient. In certain embodiments, the compound described herein is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus. Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin. (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional agents (e.g., therapeutically and/or prophylactically active agents). The compounds or compositions can be administered in combination with additional agents that improve their activity (e.g., activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-infective agent. In certain embodiments, the additional agent is an antifungal agent. In certain embodiments, the additional agent is an azole antifungal agent. Examples of anti-infective agents, including azole antifungal agents, are provided herein.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease in a subject in need thereof. In certain embodiments, the kits are useful for preventing a disease in a subject in need thereof. In certain embodiments, the kits are useful for reducing the risk of developing a disease in a subject in need thereof. In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease in a subject in need thereof. In certain embodiments, the kits and instructions provide for preventing a disease in a subject in need thereof. In certain embodiments, the kits and instructions provide for reducing the risk of developing a disease in a subject in need thereof. A kit described herein may include one or more additional pharmaceutical agents described herein as a separate composition.

Methods of Treatment and Use

Provided herein is a method for treating a disease in a subject in need thereof, the method comprising administering to the subject a compound provided herein (e.g., a compound of Formula (I), (II), or (III)), or a pharmaceutically acceptable salt, hydrate, solvate, polymorph, co-crystal, tautomer, stereoisomer, isotopically labeled derivative, or prodrug thereof, or a pharmaceutical composition thereof. Also provided are uses of a compound provided herein (e.g., a compound of Formula (I), (II), or (II)), or a pharmaceutically acceptable salt, hydrate, solvate, polymorph, co-crystal, tautomer, stereoisomer, isotopically labeled derivative, or prodrug thereof, or a pharmaceutical composition thereof, for the manufacture of a medicament for treating a disease in a subject.

In certain embodiments, the disease is an infectious disease. In certain embodiments, the disease is a microbial infection. In certain embodiments, the disease is a fungal infection.

In certain embodiments, the infectious disease is caused by a fungus belonging to a genus selected from the group consisting of *Aspergillus, Blastomyces, Candida, Coccidioides, Cryptococcus, Fusarium. Histoplasma, Malassezia, Microsporum, Mucor, Paracoccidioide, Pneumocvstis, Pseudallescheria, Rhizopus, Scedosporium, Sporothrix, Siachybotrys, Saccharomyces, Trichophyton*, and *Trichosporonphylum*; or caused by a fungus belonging to a phylum selected from the group consisting of *Ascomycota, Basidiomyvcota, Chytridiomycota, Glomeromycota*, and *Zygomycota*.

In certain embodiments, the infectious disease is caused by a fungus selected from the group consisting of *C. albicans, C. glabrata, C. krusii, C. rugosa, C. parapsilosis, C. tropicalis, C. dubliniensis, C. lusitaniae, C. guilliermondii, C. famata, C. kefyr, C. pelliculosa, C. lipolytica, C. inconspicua, C. sake, C. lambica, C. norvegensis, C. zeylanoides. Aspergillus terreus, A. clavatus, A. fumigatus, A. niger, A. flavus, Saccharomyces cerevisiae, Blastomyces dermatitidis. Coccidioides immitis, Coccidioides posadasii, Cryptococcus neoformans, C. gattii, C. albidus, C. laurentii, C. uniguttulas, E. floccosum, Fusarium graminearum, Fusarium oxysporum*, fsp. *cubense*, a member of the *Fusarium solani* complex, *Fusarium oxysporum, Fusarium verticillioides, Fusarium proliferatum, Histoplasma capsulatum, Malassezia furfur, M. circinelloides, Paracoccidioides brasiliensis, Penicillium marneffei, Pichia anomala, Pichia guilliermondi, Pneumocystis carinii, Pneumocystis jirovecii, Pseudallescheria boydii, Rhizopus orvzae, Rhodotorula rubra, Scedosporium apiospermum, Schizophyllum commnue, Sporothrix schenckii, Trichophyton mentagrophytes, Trichophyton rubrunm, Trichophyton vernrucosum, Trichophyton tonsurans, Trichophyton violaceum, Trichosporon asahii, Trichosporon culaneum, Trichosporon inkin*, and *Trichosporon mucoides*.

In certain embodiments, the infection disease is caused by a *Candida* species. In certain embodiments, the infectious disease is caused by *C. glabrata*. In certain embodiments, the infectious disease is caused by *S. cerevisiae*.

Also provided herein is a method for inhibiting the activity of a fungus in a subject or a biological sample, the method comprising administering to the subject or contacting the biological sample with a compound provided herein (e.g., a compound of Formula (I), (II), or (III)), or a pharmaceutically acceptable salt, hydrate, solvate, polymorph, co-crystal, tautomer, stereoisomer, isotopically labeled derivative, or prodrug thereof, or a pharmaceutical composition thereof. Also provided are uses of a compound provided herein (e.g., a compound of Formula (I), (H), or (III)), or a pharmaceutically acceptable salt, hydrate, solvate, polymorph, co-crystal, tautomer, stereoisomer, isotopically labeled derivative, or prodrug thereof, or a pharmaceutical composition thereof, for the manufacture of a medicament for inhibiting the activity of a fungus in a subject.

Also provided herein is a method for killing a fungus or inhibiting the growth of a fungus in a subject or a biological sample, the method comprising administering to the subject or contacting the biological sample with a compound provided herein (e.g., a of Formula (I), (II), or (III)), or a pharmaceutically acceptable salt, hydrate, solvate, polymorph, co-crystal, tautomer, stereoisomer, isotopically labeled derivative, or prodrug thereof, or a pharmaceutical composition thereof. Also provided are uses of a compound provided herein (e.g., a compound of Formula (I), (II), or (III)), or a pharmaceutically acceptable salt, hydrate, solvate, polymorph, co-crystal, tautomer, stereoisomer, isotopically labeled derivative, or prodrug thereof, or a pharmaceutical composition thereof, for the manufacture of a medicament for killing a fungus or inhibiting the growth of a fungus.

In certain embodiments, the method is carried out in an agricultural setting (e.g., on a plant). In certain embodiments, the method is carried out in a clinical setting. In certain embodiments, the method is carried out in or on a subject. In certain embodiments, the method is carried out in or on a human subject.

In certain embodiments, the fungus belongs to a genus selected from the group consisting of *Aspergillus, Blasomyces, Candida, Coccidioides, Cryptococcus, Fusarium, Histoplasma, Malassezia. Microsporum. Mucor, Paracoccidioide, Pneumocystis, Pseudallescheria, Rhizopus, Scedosporium, Sporothrix, Stachybotrys, Saccharomyces, Trichophyton*, and *Trichosporonphylum*; or caused by a fungus belonging to a phylum selected from the group consisting of *Ascomycota, Basidiomycota, Chytridiomycota, Glomeromycota*, and *Zygomycota*.

In certain embodiments, the fungus selected from the group consisting of *C. albicans, C. glabrata, C. krusii, C. rugosa, C. parapsilosis, C. tropicalis, C. dubliniensis, C. lusitaniae, C. guilliermondii, C. famata, C. kefyr, C. pelliculosa, C. lipolytica, C. inconspicua, C. sake, C. lambica, C. norvegensis, C. zeylanoides. Aspergillus terreus, A. clavatus, A. fumigatus, A. niger, A. flavus, Saccharomyces cerevisiae, Blastomyces dermatitidis, Coccidioides immitis, Coccidioides posadasii, Cryptococcus neoformans, C. gattii, C. albidus, C. laurentii, C. uniguttulas, E. floccosum. Fusarium graminearum, Fusarium oxysporum*, fsp.

cubense, a member of the *Fusarium solani* complex, *Fusarium oxvsporum, Fusarium verticillioides, Fusarium proliferatum, Histoplasma capsulatum, Malassezia furfur, M. circinelloides, Paracoccidioides brasiliensis, Penicillium marneffei, Pichia anomala, Pichia guilliermondi, Pneumocystis carinii, Pneumocystis jirovecii, Pseudallescheria boydii, Rhizopus oryzae, Rhodotorula rubra, Scedosporium apiospermum, Schizophyllum commune, Sporothrix schenckii, Trichophyton mentagrophytes, Trichophyton rubrum, Trichophyton verrucosum, Trichophyton tonsurans, Trichophyton violaceum, Trichosporon asahii, Trichosporon cutaneum, Trichosporon inkin*, and *Trichosporon mucoides*.

In certain embodiments, the fungus is a *Candida* species. In certain embodiments, the fungus is *C. glabrata*. In certain embodiments, the fungus *S. cerevisiae*.

In certain embodiments, the methods provided herein further comprise administering to a subject, or contacting a plant or biological sample, with an additional agent. In certain embodiments, the additional agent is an anti-infective agent. In certain embodiments, the additional agent is an antifungal agent. In certain embodiments, the additional agent is an azole antifungal agent.

Examples

Antifungal Hit Identification

Figure 1B:
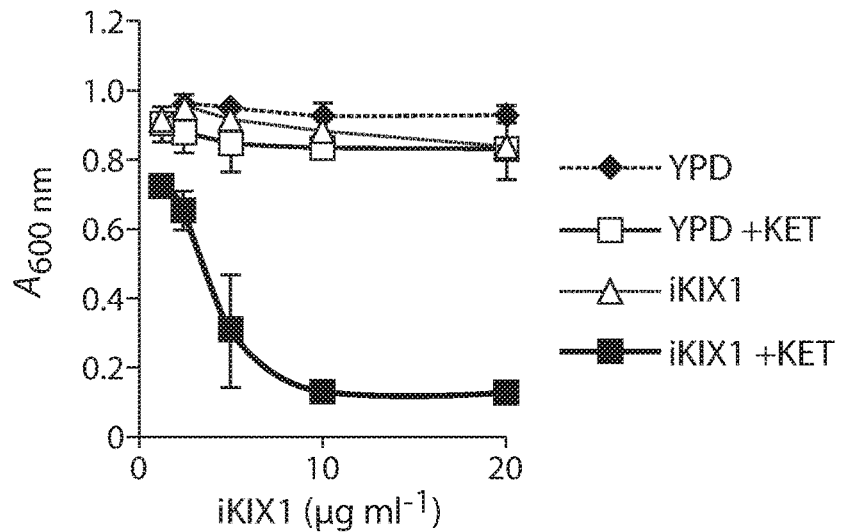
FIG. 1B, iKIX1 inhibits cell growth in a concentration-dependent manner in the presence of 5 μM ketoconazole (KET); error bars represent means+/−s.d. from duplicate plates.
Figure 1C:
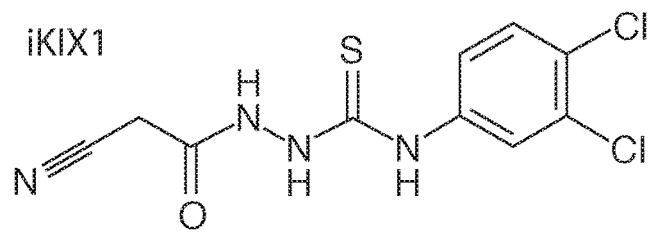
FIG. 1C. iKIX1 structure.
Figure 1D:
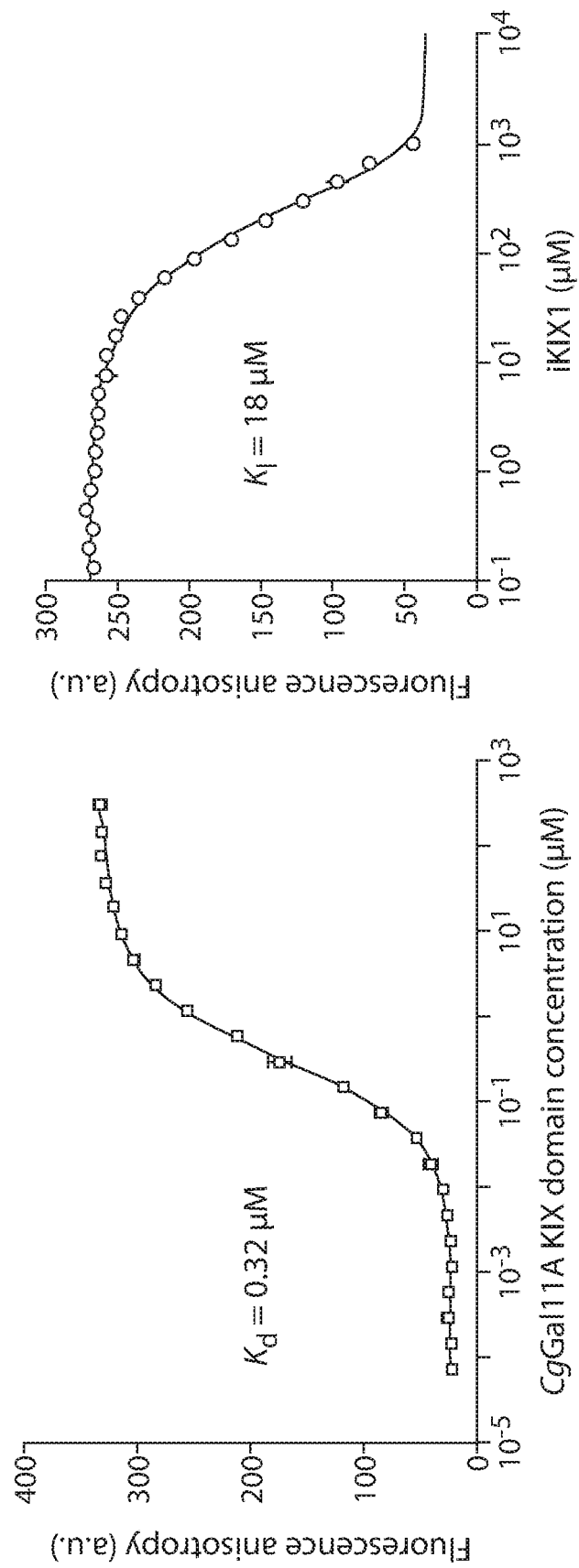
FIG. 1D. FP titration curve showing the interaction of CgGal11A KIX domain with CgPdr1 AD30 fitted to a $K_d$ of 319.7 nM±9.5 nM (left), iKIX1 competes out CgPdr1 AD30 with an $IC_{50}$ of 190.2 μM±4.1 μM (right). The measured $K_i$ and $IC_{50}$ values were used to calculate an apparent Ki of 18.1 μM for iKIX1. Data represent mean of two replicates and standard error from the fit is shown.

Based on the previous findings that deletion of the KIX domain of *Saccharomyces cerevisiae* GAL11 or *Candida glabrata* GAL11A abrogates Pdr1-dependent transcriptional responses and xenobiotic tolerance, it was hypothesized that the CgPdr1-CgGal11A interaction interface might serve as a promising target for novel anti-MDR compounds (see, e.g., Thakur, J. K. et al. A nuclear receptor-like pathway regulating multidrug resistance in fungi. *Nature* 452, 604-609, doi:nature06836 [pii] 10.1038/nature06836 (2008)). A fluorescently tagged CgPdr1 activation domain (AD) was used in an in vitro fluorescence polarization (FP) screen of ~140,000 chemically diverse compounds to identify small molecules that block the interaction between the CgGal11A KIX domain and the CgPdr1 AD (FIG. 6) (see. e.g., Roehrl, M. H., Wang, J. Y. & Wagner, G. A general framework for development and data analysis of competitive high-throughput screens for small-molecule inhibitors of protein-protein interactions by fluorescence polarization. *Biochemistry* 43, 16056-16066 (2004)). Based on the high degree of conservation between *S. cerevisiae* and *C. glabrata*, the top hits from the FP screen with an azole growth inhibition screen in *S. cerevisiae* were considered to identify hits with in vivo efficacy (FIG. 1A). Compounds that reproducibly inhibited growth in a concentration-dependent manner only in the presence of ketoconazole (FIG. 6) were identified. The most potent compound is referred to as iKIX1 (FIG. 1B, 1C). In vitro binding studies revealed that the Kd of the CgPdr1 AD for the CgGal11A KIX domain is 0.32 µM and the apparent Ki for iKIX1 is 18 µM (FIG. 1D).

Figure 2A:
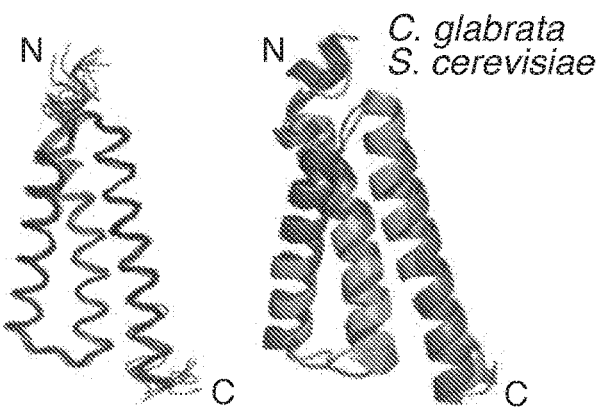
FIGS. 2A-2D show elucidation of the CgGal11A KIX domain structure; CgPdr1 AD and iKIX1 bind to a similar interface on the CgGal11A KIX domain.
Figure 2B:
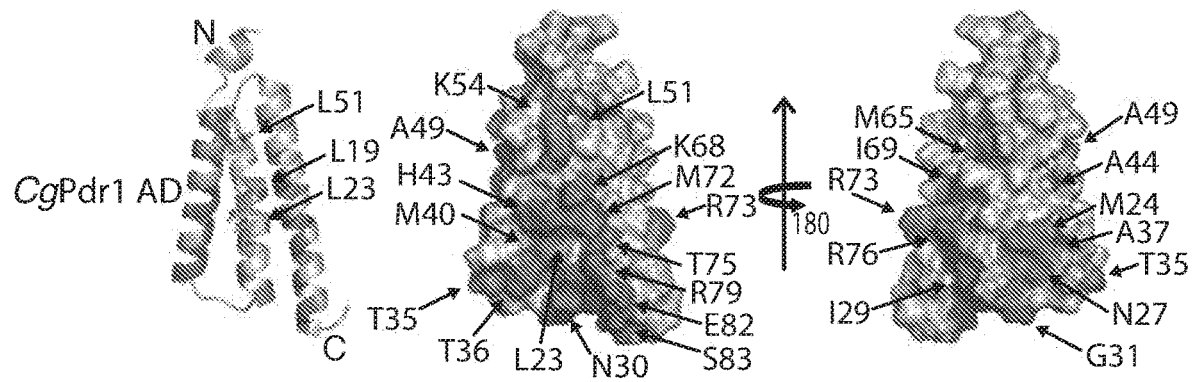
Figure 2C:
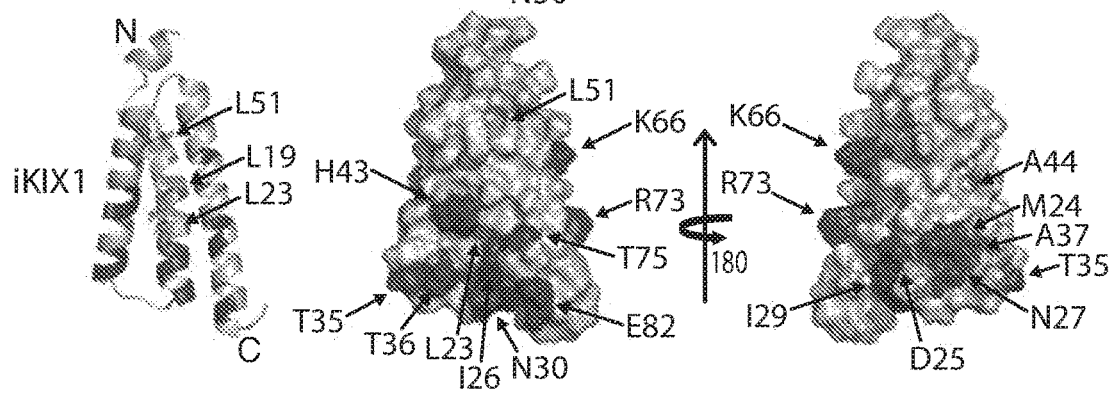
Figure 2D:
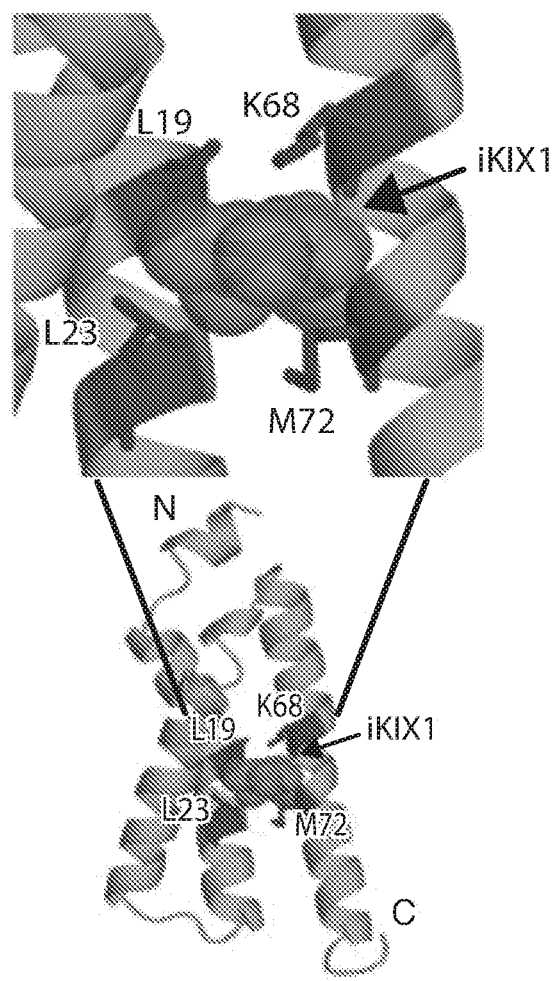
Figure 7A:
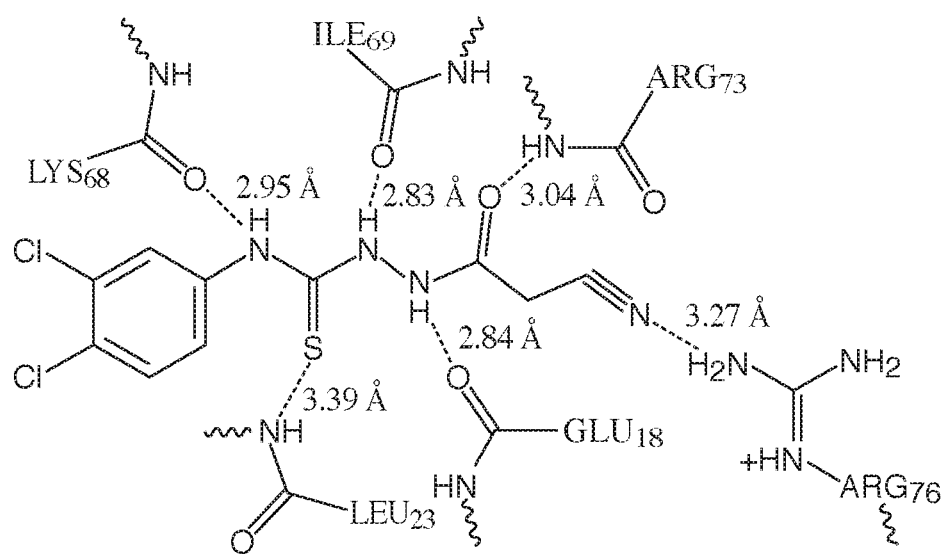
FIG. 7A. 2-dimensional representation of the H-bonding network between the CgGal11A KIX domain and iKIX1 based on docking studies.
Figure 7B:
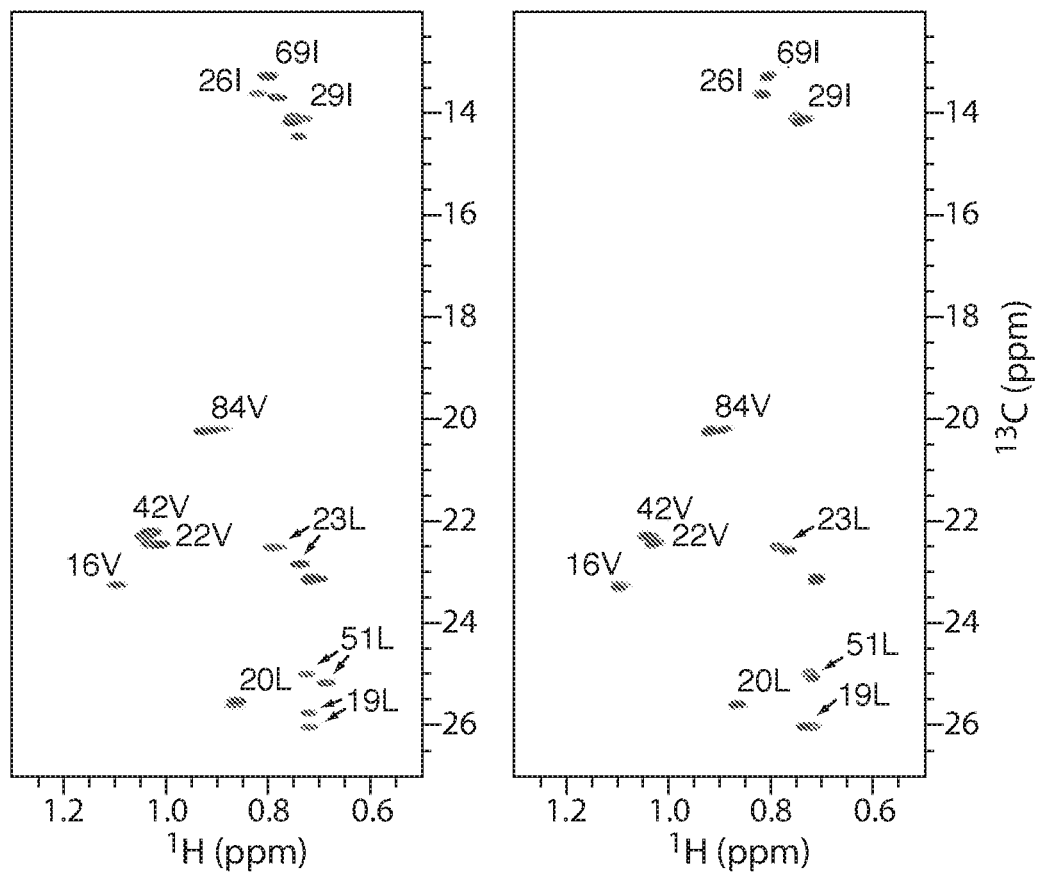
FIG. 7B. Chemical shift perturbations (CSPs) of ILV methyl resonances. Left: $^1$H-$^{13}$C HSQC showing ILV methyl resonances of CgGal11A KIX domain in presence (brown) and absence (teal) of CgPdr1 AD (2-fold excess). Right: $^1$H-$^{13}$C HSQC showing ILV methyl resonances of CgGal11A KIX domain in presence (purple) and in absence (teal) of iKIX1 (4-fold excess). Three leucines (L19, L23, L51) show significant CSPs in both spectra.
Figure 7C:
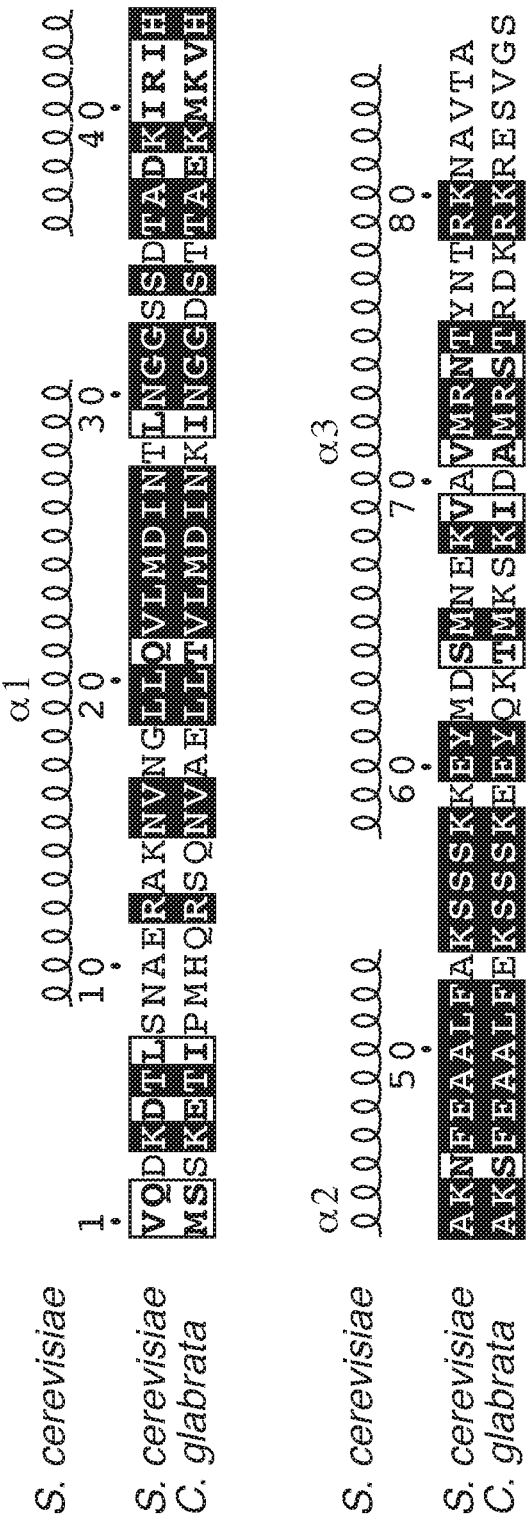
FIG. 7C. Sequence alignment of the C. glabrata Gal11A and S. cerevisiae Gal11/Med15 KIX domains (see, e.g., Robert, X. & Gouet, P. Deciphering key features in protein structures with the new ENDscript server. Nucleic acids research 42, W320-324, doi:10.1093/nar/gku316 (2014)).

To facilitate the elucidation of the mechanism of action of iKIX1, the high-resolution solution structure of the CgGal11A KIX domain with a backbone RMSD of 0.7 Å was determined (FIGS. 2A-2D and FIG. 5; PDB #4D7X). The CgGal11A KIX domain has 51% sequence identity and 61% similarity with the *S. cerevisiae* Gal11/Med15 KIX domain with an overall RMS deviation of 2.0 Å (FIG. 2A and FIG. 7C). The CgGal11A KIX domain forms a three-helix bundle harbouring an extensively hydrophobic core and a short helix at the N-terminus (FIG. 2A). Interaction interfaces of the CgGal11A KIX domain with the CgPdr1 AD and iKIX1 (FIG. 2B) were determined by chemical shift perturbation (CSP) analysis. The CgPdr1 AD and iKIX1 target the same large hydrophobic groove harboured by the three helices. Residues from all three helices constitute the interaction interface, and titration of an ILV-methyl labeled CgGal11A KIX domain reveals large CSPs on the three leucines (L19, L23 and L51) upon addition of CgPdr1 AD and iKIX1 (FIG. 7B). The basic interaction interface on the KIX domain complements the acidic residues of CgPdr1 AD (FIG. 2C). Residues of the CgGal11A KIX domain that interact with CgPdr1 AD and iKIX1 overlap strongly, suggesting direct competitive binding as the mechanism of inhibition. Docking of iKIX1 to the CgGal14A KIX domain suggests extensive hydrogen bonding and hydrophobic interactions between iKIX1 and KIX domain residues (FIG. 2D and FIG. 7A), matching the interaction interface mapped by CSP analysis.

Figure 3A:
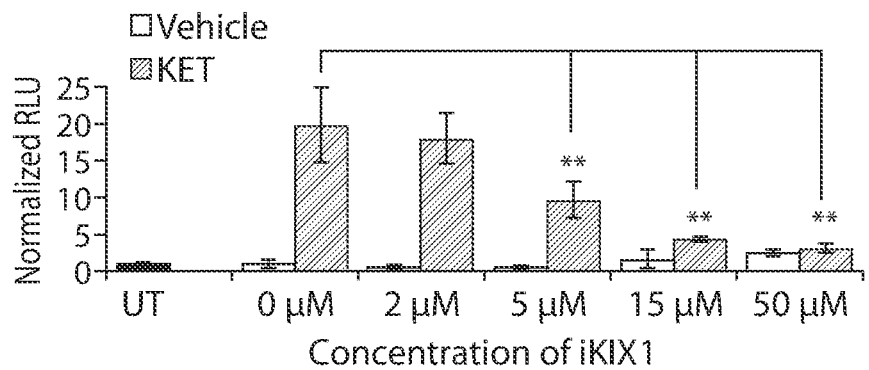
FIGS. 3A-3G show iKIX1 blocks Gal11/Med15 recruitment and upregulation of Pdr1 target genes.

To assess the in vivo effects of iKIX1 on Pdr1-dependent transcription, a strain was initially utilized in which the two *S. cerevisiae* PDR1 orthologues (ScPDR1 and ScPDR3) are deleted and which carries a plasmid expressing CgPDR1, and a heterologous luciferase gene driven by 3 pleiotropic drug response elements (PDREs). Luciferase activity was strongly induced by ketoconazole treatment; iKIX1 co-treatment was able to block this induction in a concentration-dependent manner (FIG. 3A).

Figure 3B:
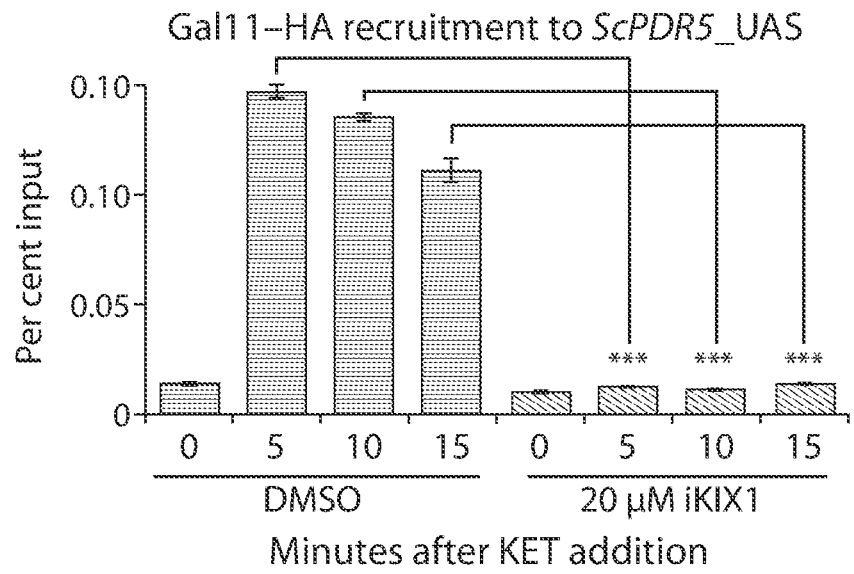
Figure 3C:
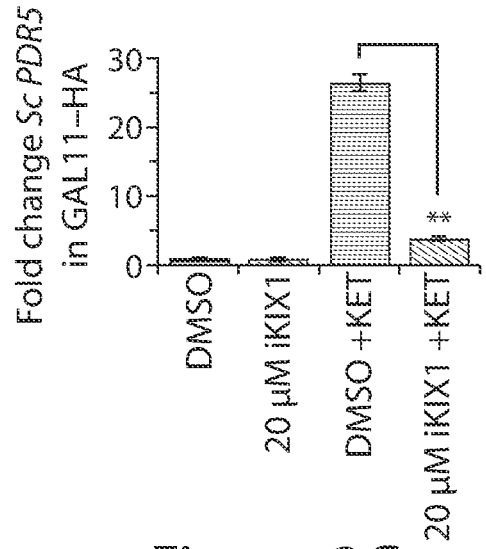
Figure 8A:
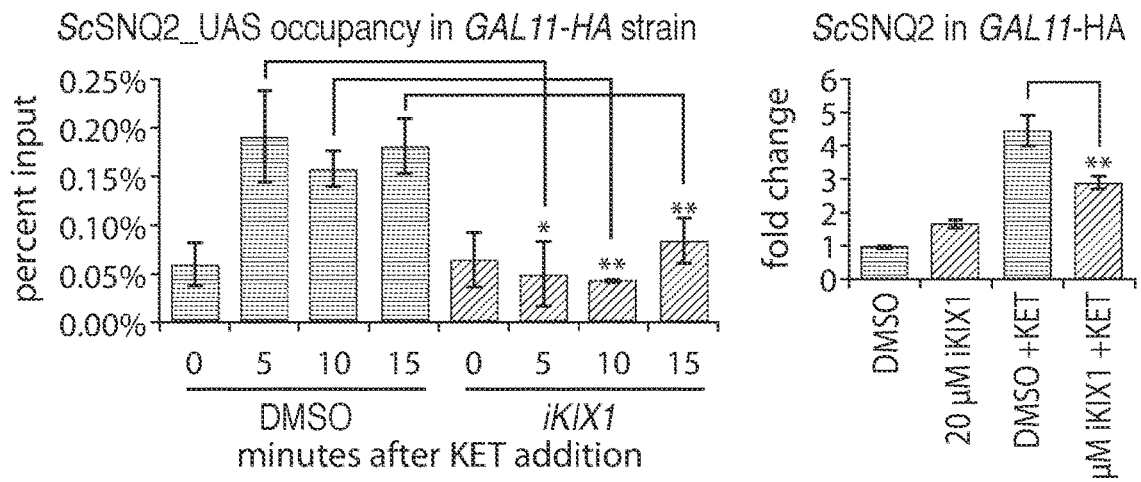
FIG. 8A, iKIX1 prevents the ketoconazole (KET)-induced recruitment of ScGal11/Med15/Mediator to the upstream activating sequences (UAS) of the PDRE-regulated promoter ScSNQ2 and transcriptional upregulation of ScSNQ2.
Figure 8B:
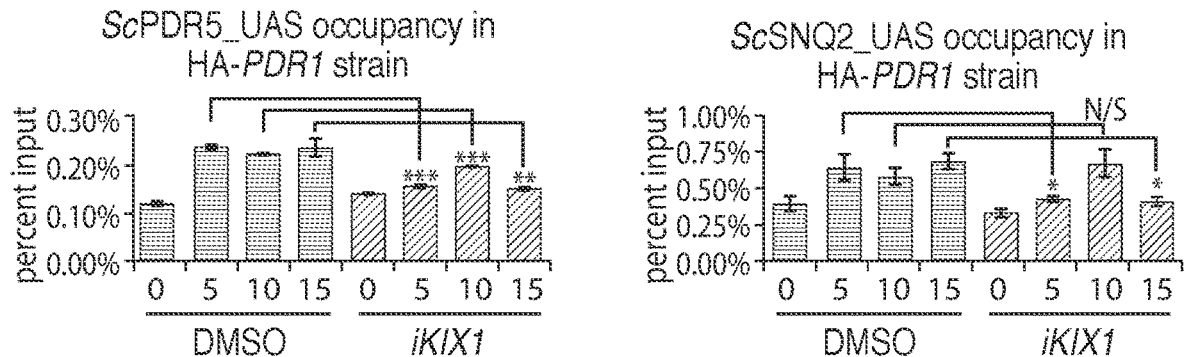
FIG. 8B. HA-Pdr1 occupies PDRE-regulated promoters of ScPDR5 and ScSNQ2 in the presence of 20 µM iKIX1 or vehicle (DMSO) control prior to and following ketoconazole (KET) addition.
Figure 8C:
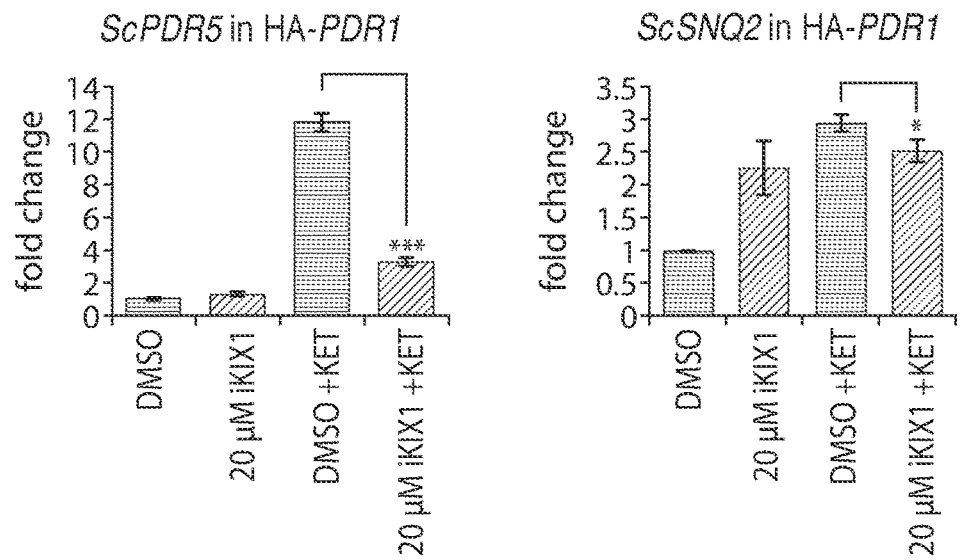
FIG. 8C. 20 µM iKIX1 inhibits ketoconazole-induced upregulation of ScPdr1 target genes ScPDR5 and ScSNQ2 in the HA-Pdr1 strain. RNA was harvested concurrently with representative chromatin immunoprecipitation experiment shown FIG. 8B at t=0 min. (DMSO, 20 µM iKIX1) and t=15 min. after ketoconazole induction (DMSO+KET, 20 µM iKIX1+KET). Transcripts are normalized to ScSCR1 and un-induced DMSO control. (a-c) Representative experiment from two biological replicates is shown. Error bars represent mean+/−s.d. of technical replicates; *P<0.05, P<0.01 and *P<0.001 as calculated by two-tailed Student's t-test.

A chromatin immunoprecipitation (ChIP) assay was used to examine Gal11/Med15 recruitment to Pdr1-regulated target genes in *S. cerevisiae* after iKIX) treatment. Gal11/Med15 was rapidly recruited to the promoters of the Pdr1 target genes PDR5 and SNQ2 after ketoconazole addition; in contrast, ketoconazole-induced recruitment of Gal11/Med15 was abrogated when the cells were pre-treated with iKIX1 (FIG. 3B and FIG. 8A), iKIX1 did not impede the constitutive occupancy of Pdr1 at the same Pdr1-regulated target genes (FIG. 88). Consistent with the ChIP data, iKIX1 strongly inhibited azole-induced transcription of ScPdr1 target genes (FIG. 3C, FIG. 8A, FIG. 80.

Figure 3D:
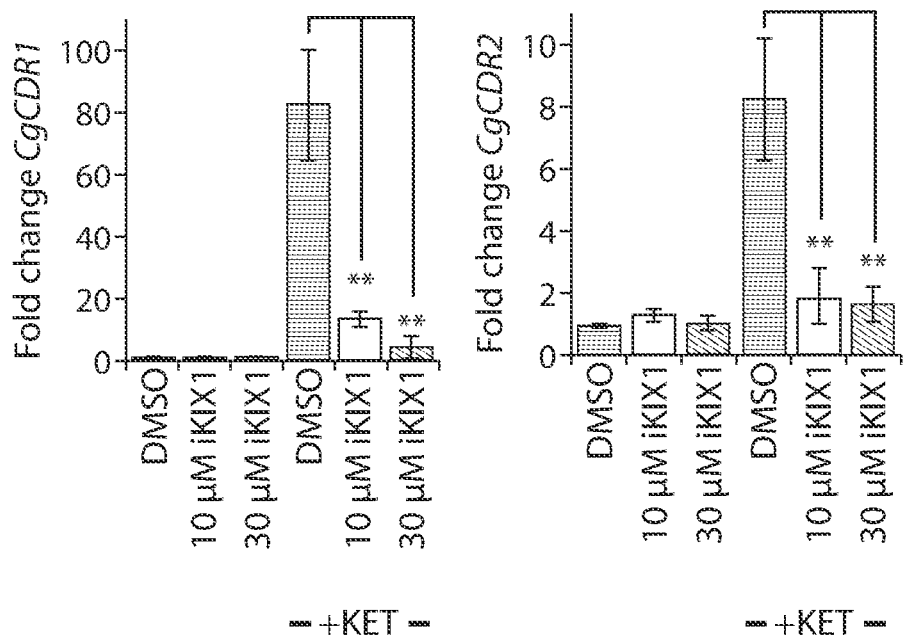
Figure 9A:
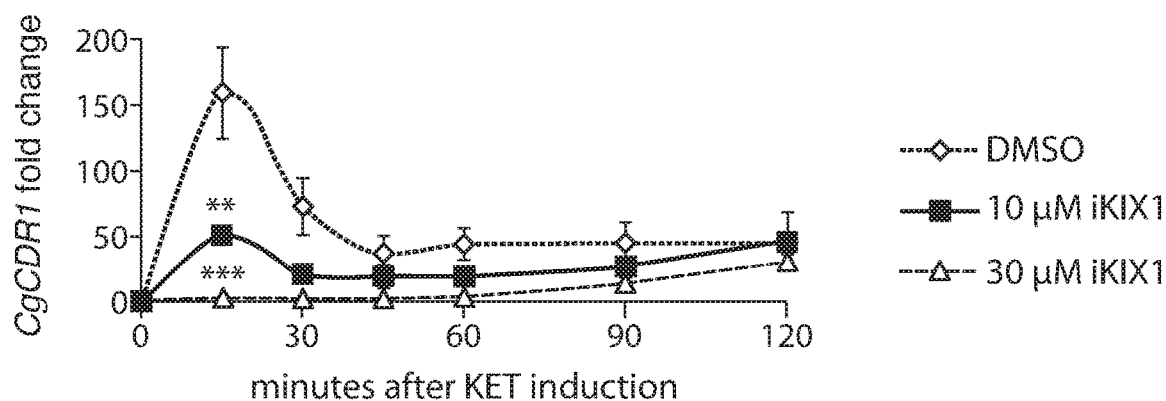
Figure 9B:
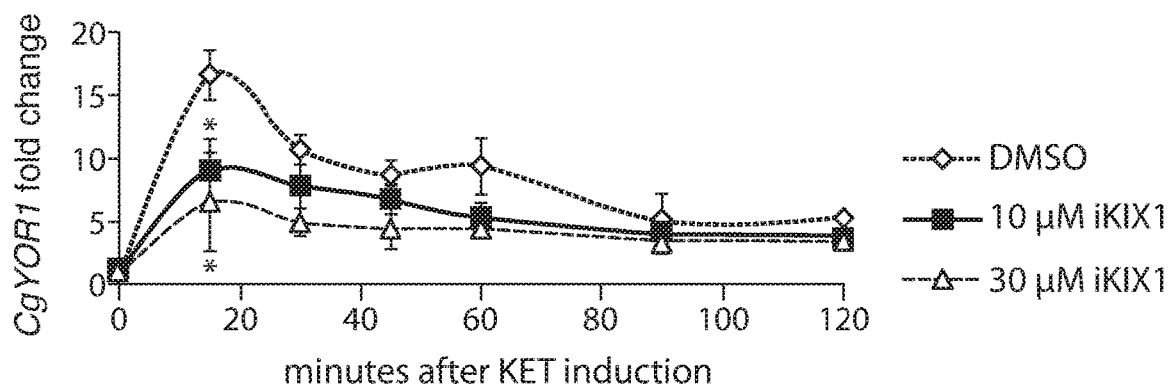
Figure 9C:
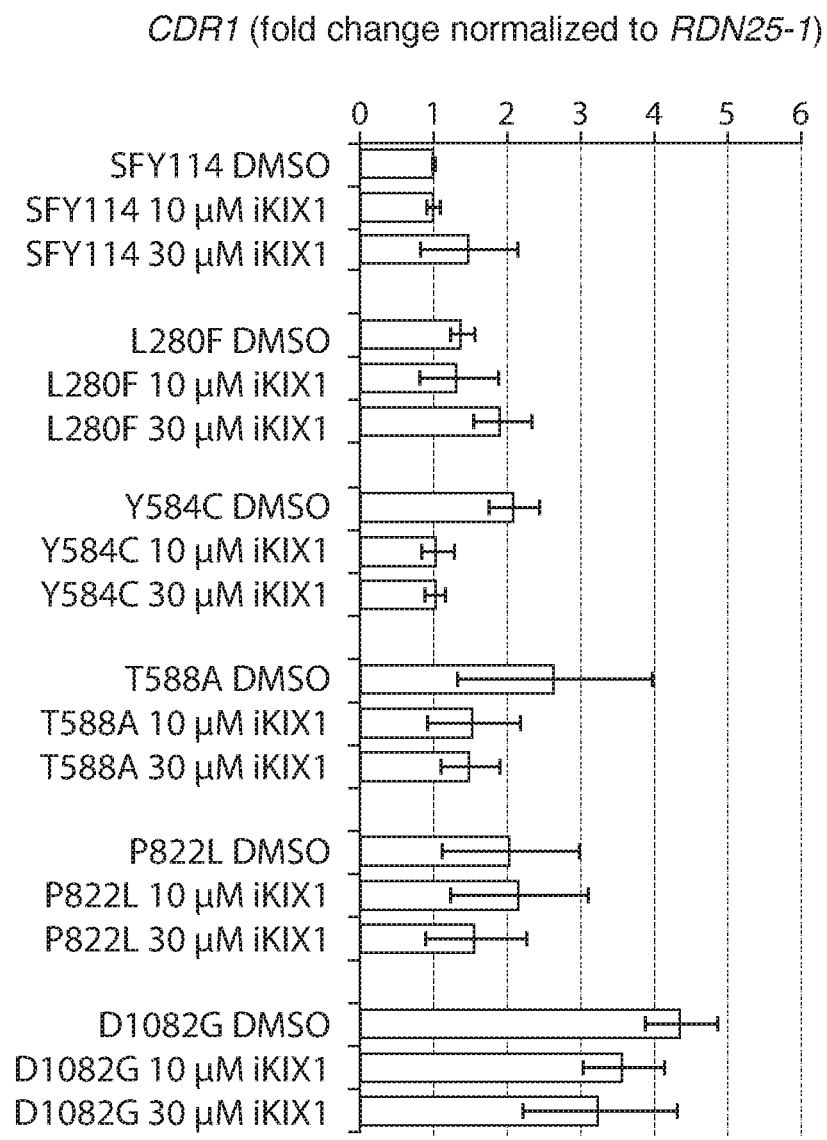

Next, the effect of iKIX1 on the transcription of *C. glabrata* Pdr1-regulated genes involved in drug efflux and MDR (CgCDR1. CgCDR2 and CgYOR1) was determined. CgPdr1 targets were strongly up-regulated after ketoconazole treatment (see, e.g., Vermitsky, J. P. et al. Pdr1 regulates multidrug resistance in *Candida glabrata*: gene disruption and genome-wide expression studies. *Mol Microbiol* 61, 704-722 (2006); Ferrari, S., Sanguinetti, M., Torelli, R., Posteraro, B. & Sanglard, D. Contribution of CgPDR1-regulated genes in enhanced virulence of azole-resistant *Candida glabrata. PLoS One* 6, e17589, doi:10.1371/journal.pone.0017589). However, pre-treatment with iKIX1 reduced target gene induction in a durable and concentration-dependent manner (FIG. 3D and FIG. 9A, FIG. 9B). Treatment with iKIX1 alone did not significantly affect Pdr1-target gene induction (FIG. 9C, FIG. 9D).

Figure 3E:
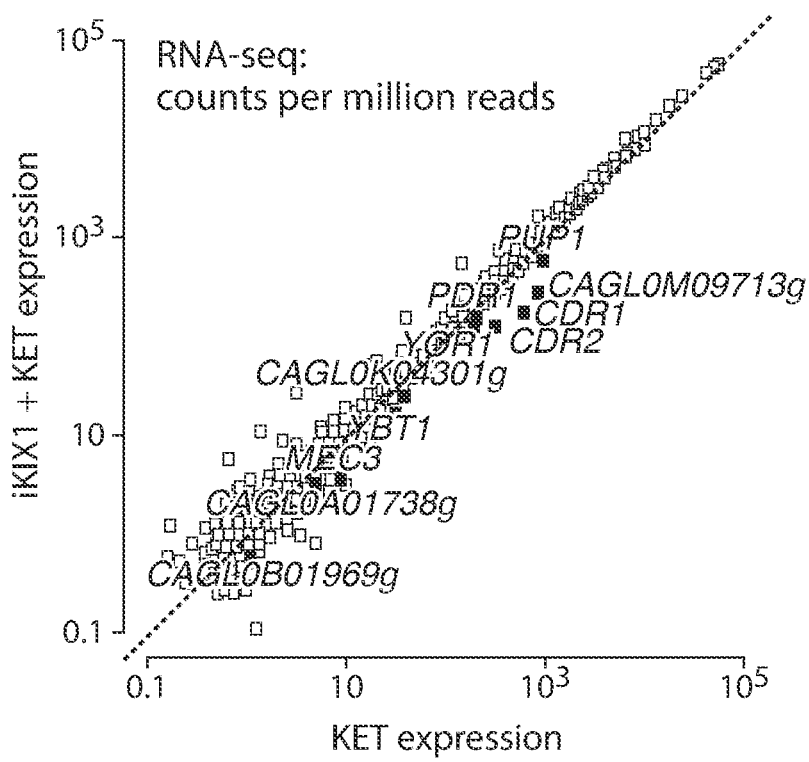
Figure 8D:
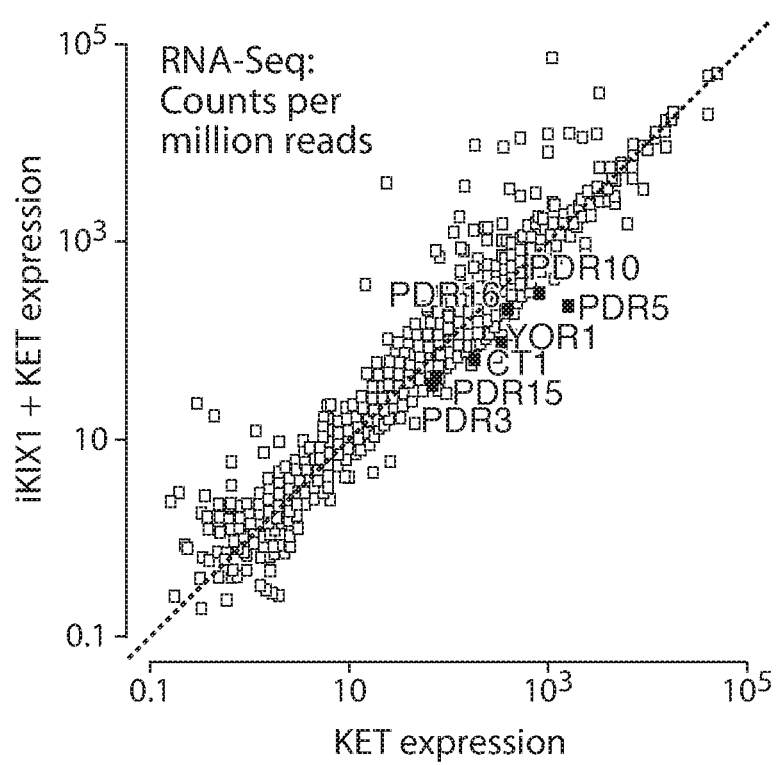
FIG. 8D. RNA-Seq analysis of a wild-type S. cerevisiae strain (BY4741) pre-treated with iKIX1 or vehicle alone then induced with ketoconazole (iKIX1+KET and KET, respectively) demonstrate a blunted induction of Pdr1 target genes following iKIX1 pre-treatment. Data represents means of three biological replicates.
Figure 8E:
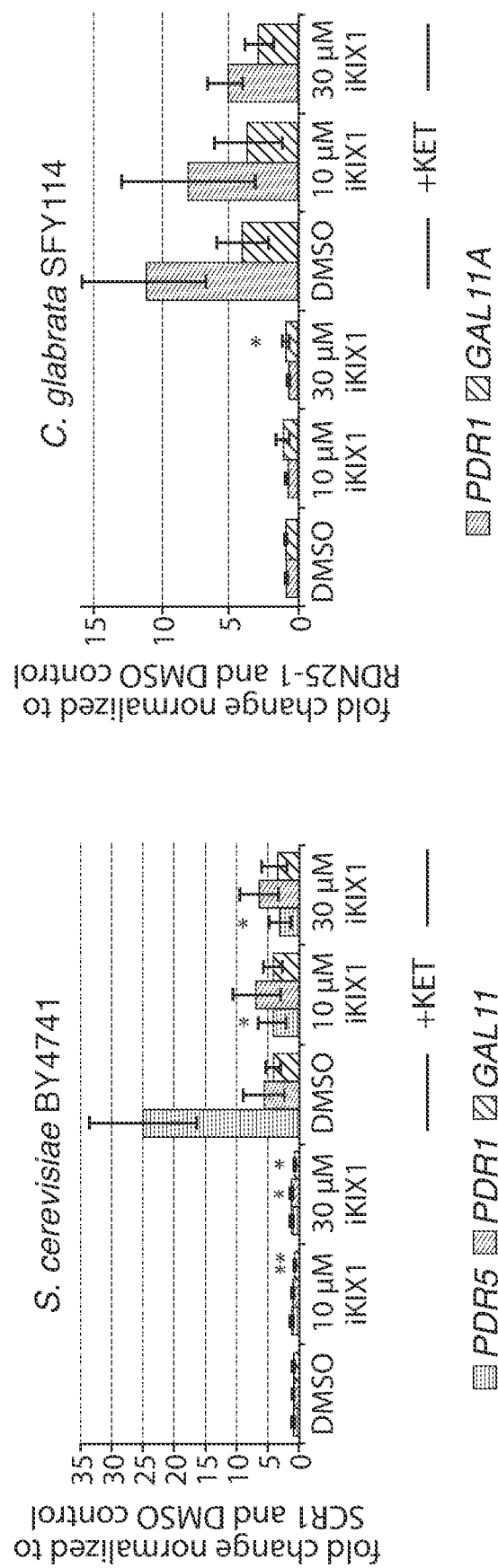
FIG. 8E, iKIX1 pre-treatment does not significantly alter the transcript levels of PDR1 or GAL11/GAL11A in S. cerevisiae or C. glabrata after azole induction. Cells were pre-incubated with vehicle (DMSO) or iKIX1 and then induced with 40 µM ketoconazole (+KET) for 15 minutes before harvest. Average value of three biological replicates is shown and error bars represent mean+/−standard deviation; *P<0.05, **P<0.001 as compared to DMSO or DMSO+ KET control, calculated by two-tailed Student's t-test.

Next generation RNA sequencing (RNA-Seq) was employed to query the genome-wide effects of iKIX1 and azole treatments alone and in combination on the transcriptome in both *S. cerevisiae* and in *C. glabrata*. In accord with previous reports, azole treatment up-regulates Pdr1-dependent genes in both yeasts, such as the drug efflux pumps ScPDR5 and CgCDR1 (see, e.g., Ferrari, S., Sanguinetti, M., Torelli, R., Posteraro, B. & Sanglard, D. Contribution of CgPDR1-regulated genes in enhanced virulence of azole-resistant *Candida glabrata. PLoS One* 6, e17589. doi: 10.1371/journal.pone.0017589; DeRisi, J. et al. Genome microarray analysis of transcriptional activation in multidrug resistance yeast mutants. *FEBS Lett* 470, 156-160, doi:S0014-5793(00)01294-1 [pii] (2000)). Combined azole and iKIX1 treatment strongly blunted expression of many azole-activated and Pdr1-dependent genes in both *S. cerevisiae* and *C. glabrata* (FIG. 3E, FIG. 8D). consistent with prior data and the proposed mechanism of action of iKIX1, iKIX1 alone affected very different sets of genes in *S. cerevisiae* and *C. glabrata*. Treatment of *S. cerevisiae* and *C. glabrata* cells with iKIX1 did not significantly alter the expression of PDR1 or GAL11/MED15 after azole treatment (FIG. 8E). Together, these findings suggest that the primary mechanism of synergistic antifungal effects of iKIX1 with azoles is through blocking the azole-stimulated and Pdr1-dependent drug efflux pathway.

Figure 3F:
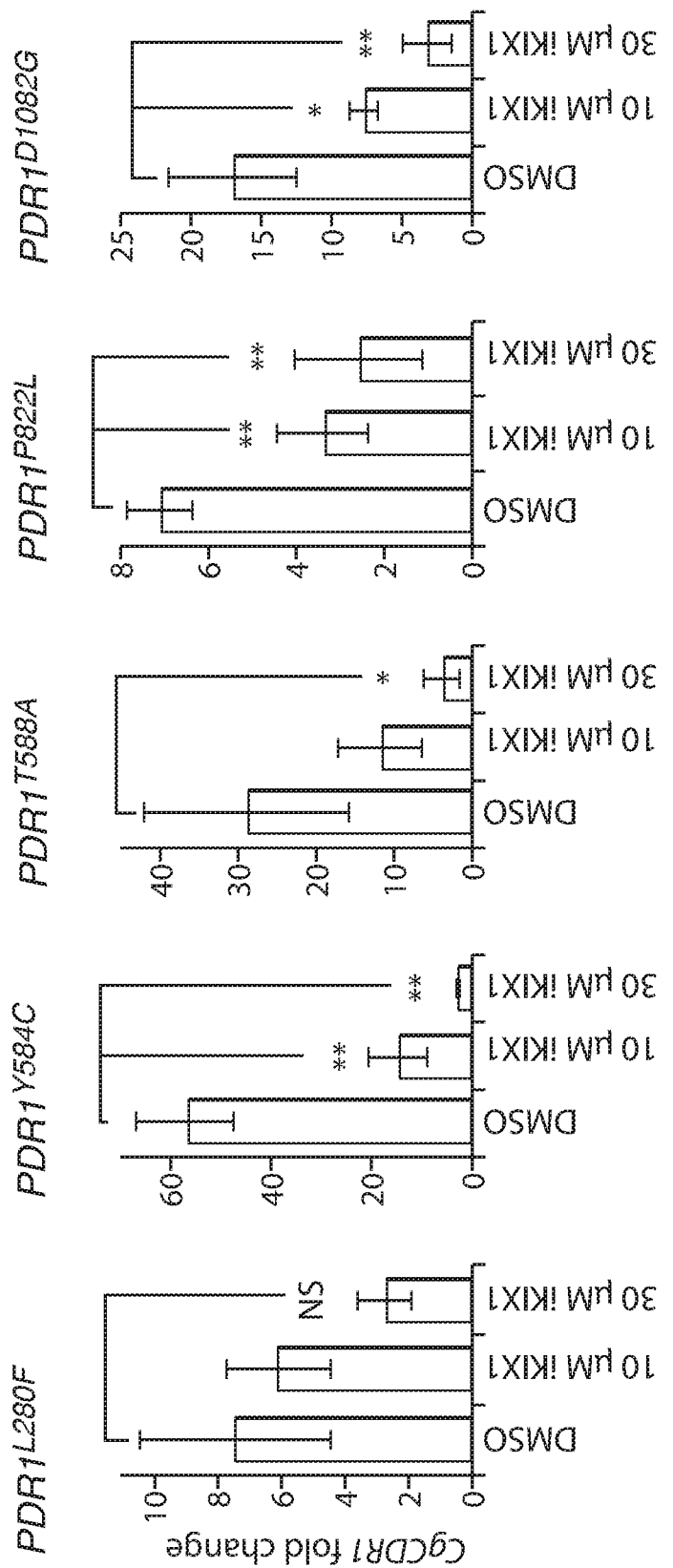
Figure 3G:
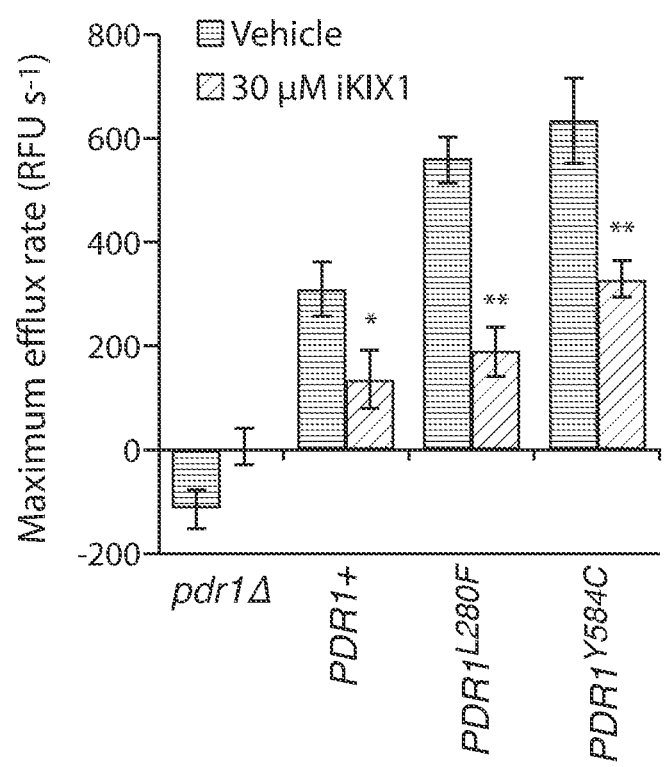

To ascertain iKIX1 efficacy in azole-resistant *C. glabrata* strains, the effects of iKIX1 was examined on CgPdr1 target gene expression in a set of isogenic strains with gain-of-function CgPDR1 mutations originally identified in azole-resistant *C. glabrata* clinical isolates (see, e.g., Ferrari, S. et al. Gain of function mutations in CgPDR1 of *Candida glabrata* not only mediate antifungal resistance but also enhance virulence. PLoS Pathog 5, e1000268, doi:10.1371/journal.ppat.1000268 (2009)), iKIX1 reduced azole-induced transcription of CgPdr1 target genes (e.g., CgCDR1) in a concentration-dependent manner in all strains tested (FIG. 3F and FIG. 9D).

Figure 10:
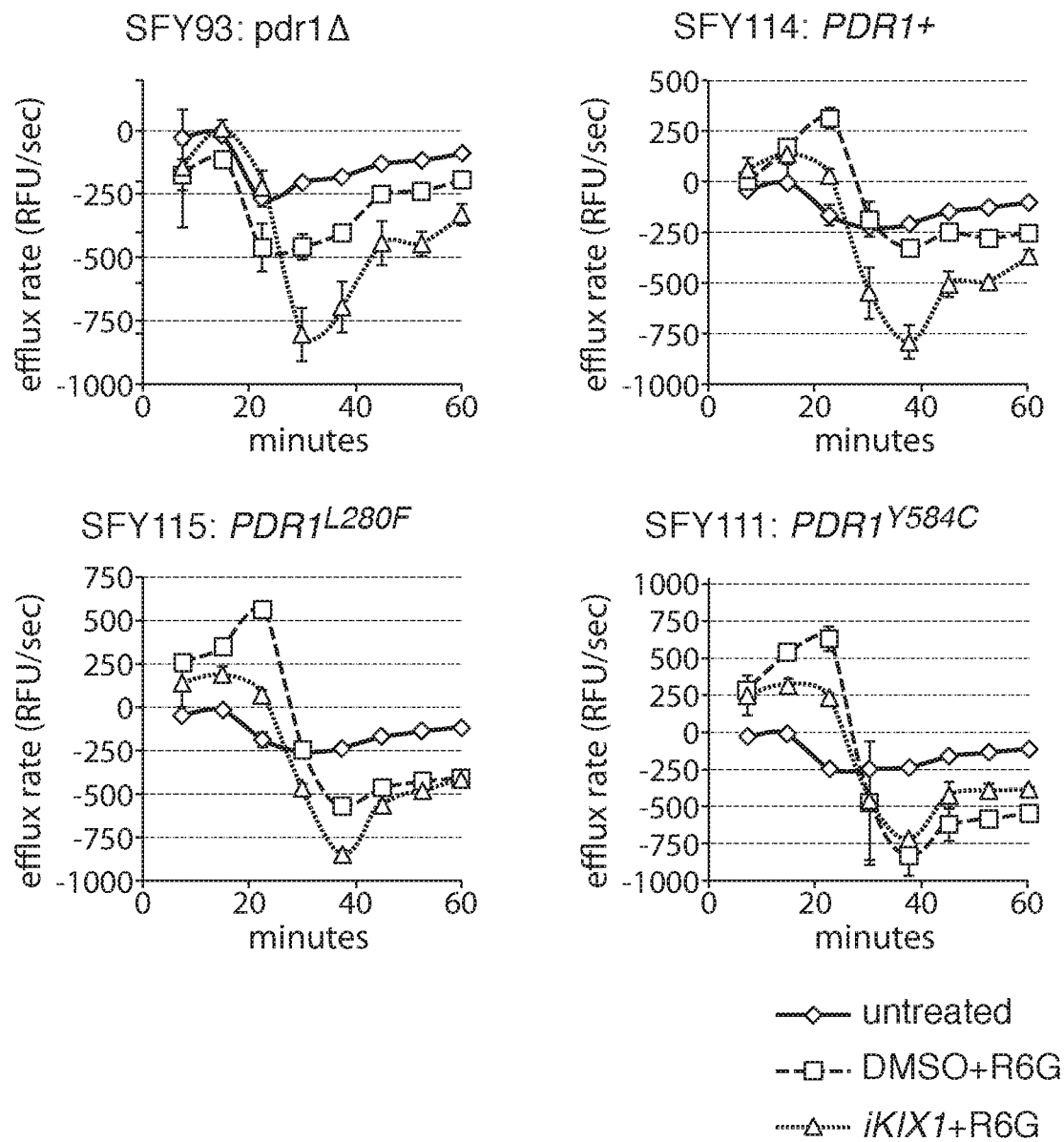
FIG. 10 shows iKIX1 inhibits efflux of rhodamine 6G in PDR1 wild-type, PDR1$^{L280F}$ and PDR1$^{Y584C}$ strains. Data points indicate mean of three biological replicates and error bars represent mean+/−s.d.

To investigate whether these transcriptional effects translated to functional effects on drug efflux rates, the fluorescent compound rhodamine 60, a substrate of the i efflux pump, was utilized (see, e.g., Sanglard, D., Ischer. F., Calabrese, D., Majcherczyk, P. A. & Bille, J. The ATP binding cassette transporter gene CgCDR1 from *Candida glabrata* is involved in the resistance of clinical isolates to azole antifungal agents. Antimicrobial agents and chemotherapy 43, 2753-2765 (1999); Silva, L. V. et al. Milbemycins: more than efflux inhibitors for fungal pathogens. Antimicrob Agents Chemother 57, 873-886, doi:AAC.02040-12 [pii]10.1128/AAC.02040-12). Maximum efflux rates were significantly decreased in PDR1 wild-type or gain-of-function strains pre-treated with iKIX1, as compared to vehicle control (FIG. 3D and FIG. 10).

Figure 4A:
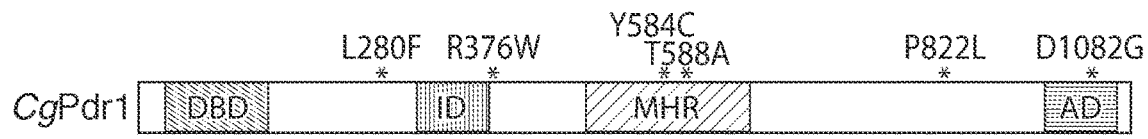
FIGS. 4A-4D show iKIX1 as a co-therapeutic in models of C. glabrata disseminated disease.
Figure 4B:
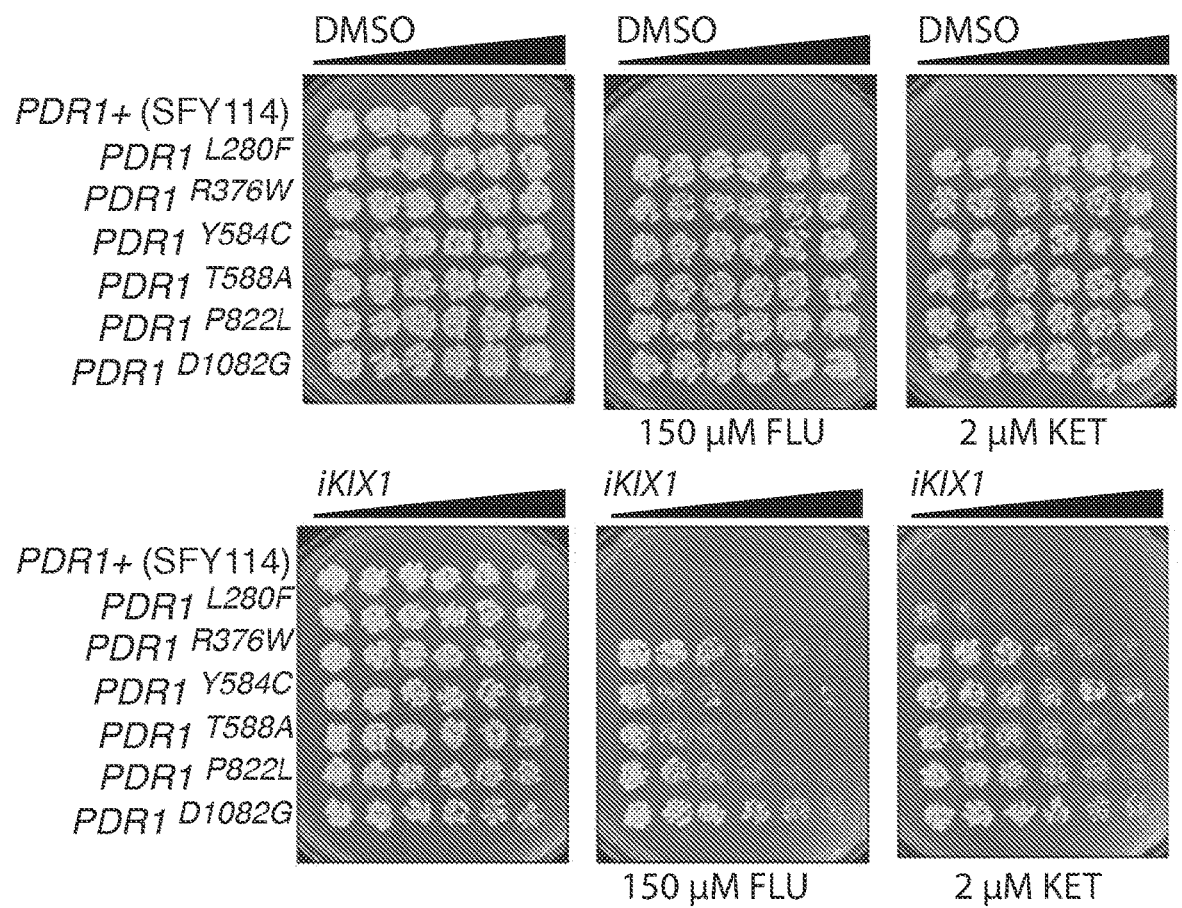
Figure 11A:
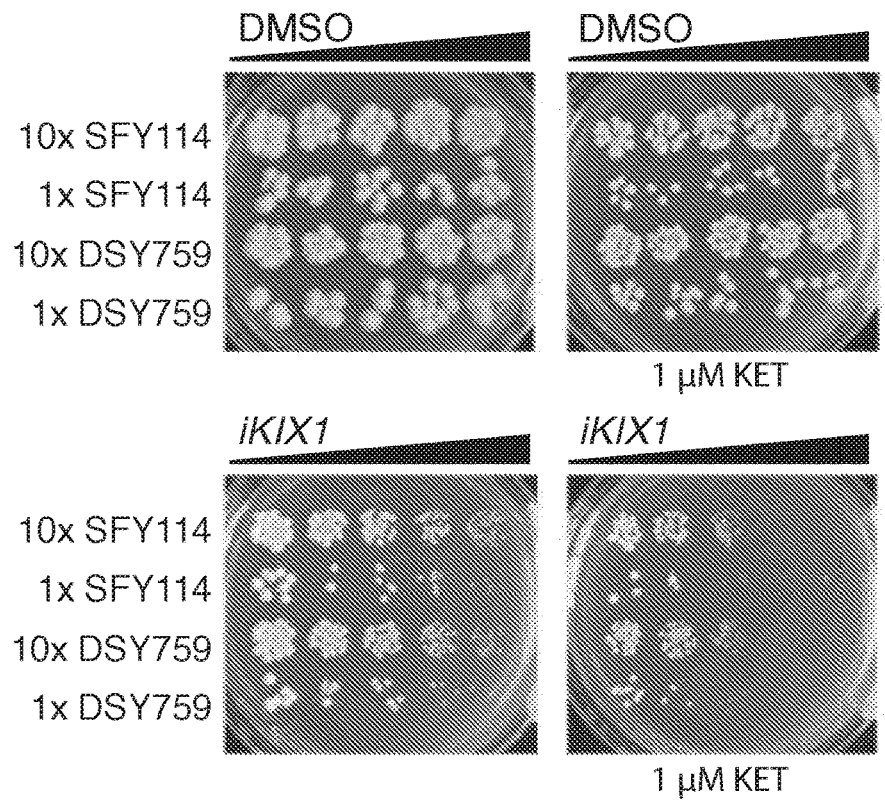
FIGS. 11A and 11B, iKIX1 increases the sensitivity of Cg strains bearing wild-type CgPDR1 to azole treatment. Two strains bearing wild-type CgPDR1 alleles (SFY114. DSY759) were plated at concentrations differing by ten-fold (10×, 1×) on plates containing increasing concentrations of (FIG. 11A) iKIX1 to 300 µM in the presence or absence of 1 µM ketoconazole (KETO) or (FIG. 11B) iKIX1 to 250 µM in the presence or absence of 50 µM fluconazole (FLU).
Figure 11B:
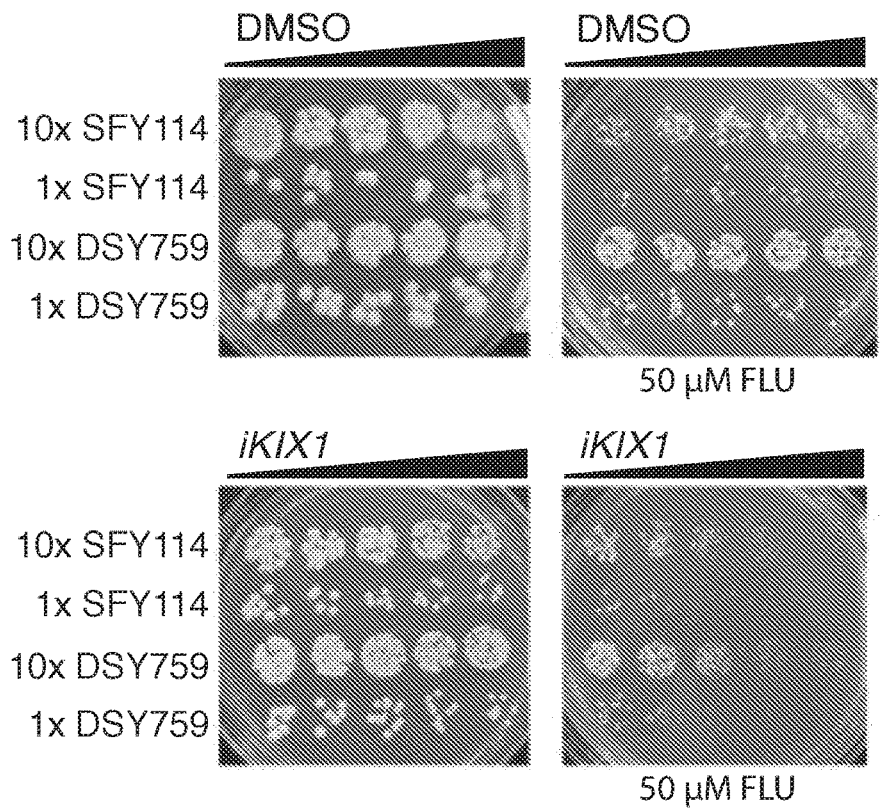

Due to its ability to reduce efflux pump gene expression and pump activity, it was predicted that iKIX1 could restore azole-sensitivity to CgPDR1 gain-of-function mutant strains. Isogenic *C. glabrata* strains with wild-type or single gain-of-function alterations across CgPdr1 (FIG. 9A) were tested for their sensitivity to fluconazole or ketoconazole on gradient plates with increasing concentrations of iKIX1 or vehicle. As expected, a CgPDR1 wild-type strain was sensitive to both fluconazole and ketoconazole, whereas CgPDR1 gain-of-function mutant strains grew robustly in the presence of azoles, iKIX1 restored azole-sensitivity to PDR1 gain-of-function mutant strains in a concentration-dependent manner (FIG. 4B). CgPDR1 wild-type strains also exhibited increased growth inhibition in the presence of both iKIX1 and azole versus single agents alone (FIG. 11A. FIG. 11B).

Figure 11C:
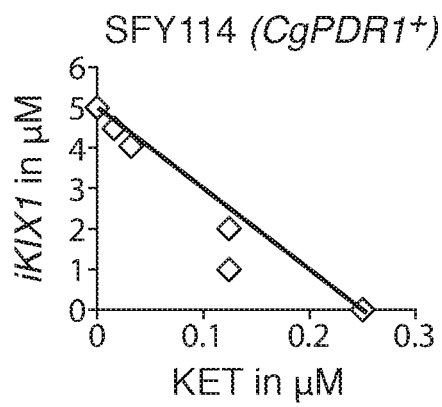
FIG. 11C, iKIX1 and ketoconazole (KET) have additive effects on the growth of a CgPDR1 wild-type strain.
Figure 11D:
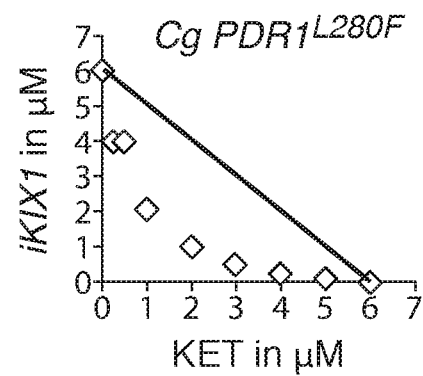
FIG. 11D, iKIX1 and ketoconazole (KET) synergistically inhibit the growth of the CgPDR1$^{L280F}$ mutant.

Based on the strong combination effect of azoles and iKIX1 in the CgPDR1$^{L280F}$ mutant follow-up studies were focused on this mutant strain. To investigate whether azoles and iKIX1 act in a synergistic or additive manner in CgPDR1 wild-type and CgPDR1$^{L280F}$ mutant strains, growth in checkerboard assays was assessed with ketoconazole and iKIX1. In the wild-type CgPDR1 strain, the combination of ketoconazole and iKIX1 was additive (FIG. 11C). However, the CgPDR1$^{L280F}$ mutant exhibited synergistic growth inhibition with iKIX1 and ketoconazole combination treatment, with combination indices <1 (FIG. 11D). in concordance with the spot-plating assay.

A limited analysis was carried out exploring the chemical space around the iKIX1 scaffold using commercial and custom synthesized iKIX1 analogs, identifying several compounds that lost activity in all assays; one analog (A2) is shown in Extended Data FIG. 7a-d. This example, together with data from iKIX1 analogs and the docked structure of iKIX1 to the CgGal11A KIX domain, supports a model where iKIX1 engages the core of the KIX domain using an array of hydrophobic and hydrogen bond contacts.

Figure 4C:
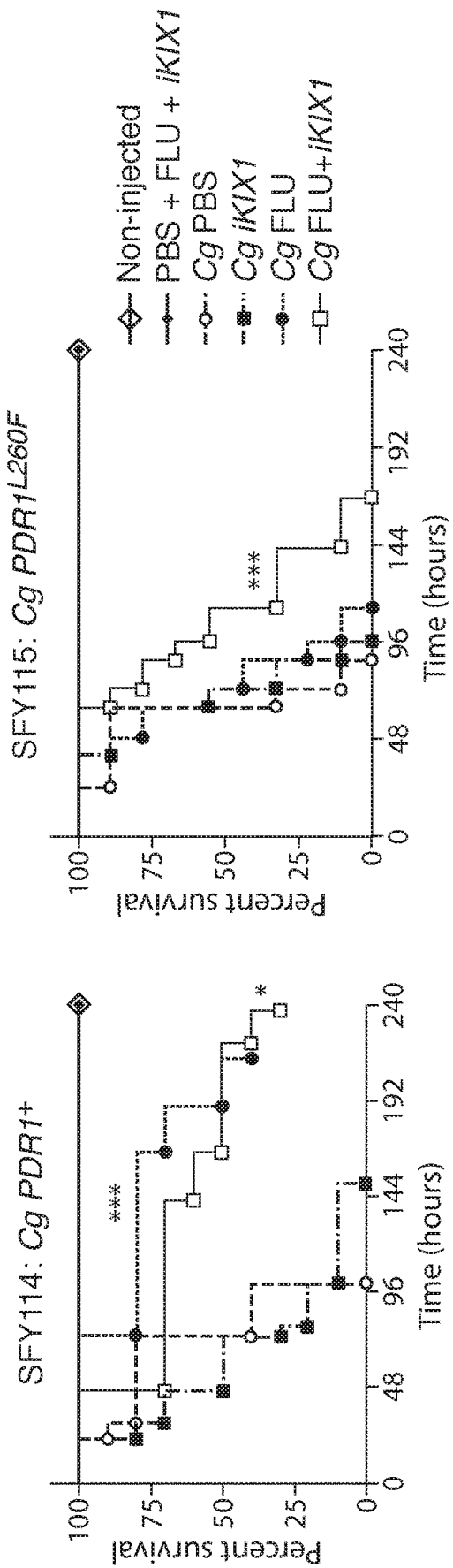

Two metazoan model systems were utilized to evaluate the potential utility of iKIX1 as a co-therapeutic with fluconazole to treat disseminated *C. glabrata* infection. The larvae of the moth *Galleria mellonella* has been used as a model to test the pathogenicity of a wide variety of human pathogens (see, e.g., Arvanitis, M., Glavis-Bloom, J. & Mylonakis, E. Invertebrate models of fungal infection. Biochimica et biophysica acta 1832, 1378-1383, doi: 10.1016/j.bbadis.2013.03.008 (2013)). A *G. mellonella* survival assay was utilized to determine the virulence of *C. glabrata* PDR1 wild-type or PDR1$^{L280F}$ strains in the presence of fluconazole, iKIX1, or a combination of the two (FIG. 4C). Larvae were injected with *C. glabrata* and a single injection of fluconazole (50 mg/kg), iKIX1 (25 mg/kg). a combination of the two, or vehicle; survival was monitored every 24 hours. *G. mellonella* injected with wild-type CgPDR1 was sensitive to fluconazole alone, and exhibited no significant alterations in survival with a fluconazole-iKIX1 combination. However, in *G. mellonella* larvae injected with a CgPDR1$^{L280F}$ strain, whereas the single agents fluconazole or iKIX1 did not significantly increase survival compared to vehicle, co-treatment with iKIX1 and fluconazole significantly increased survival (P<0.001).

Figure 12A:
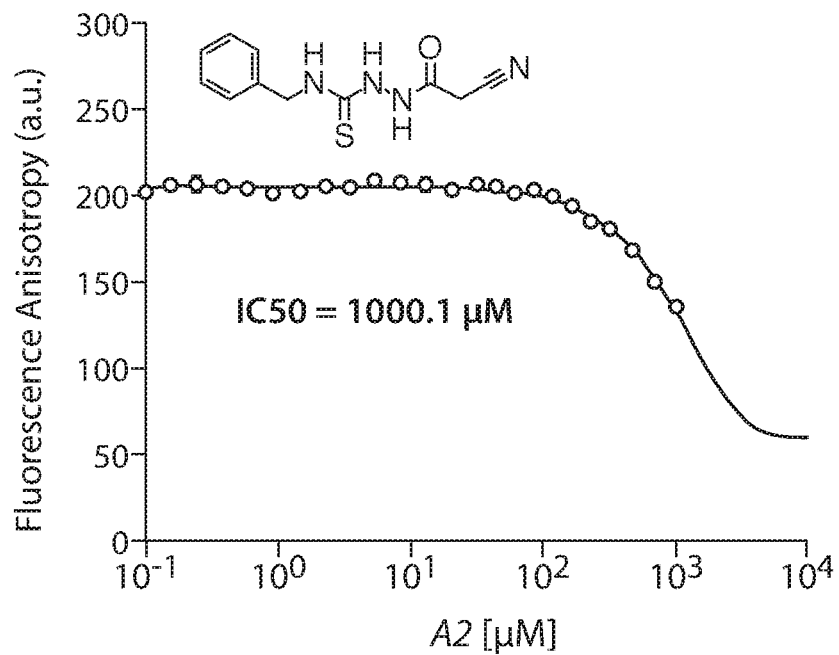
Figure 12B:
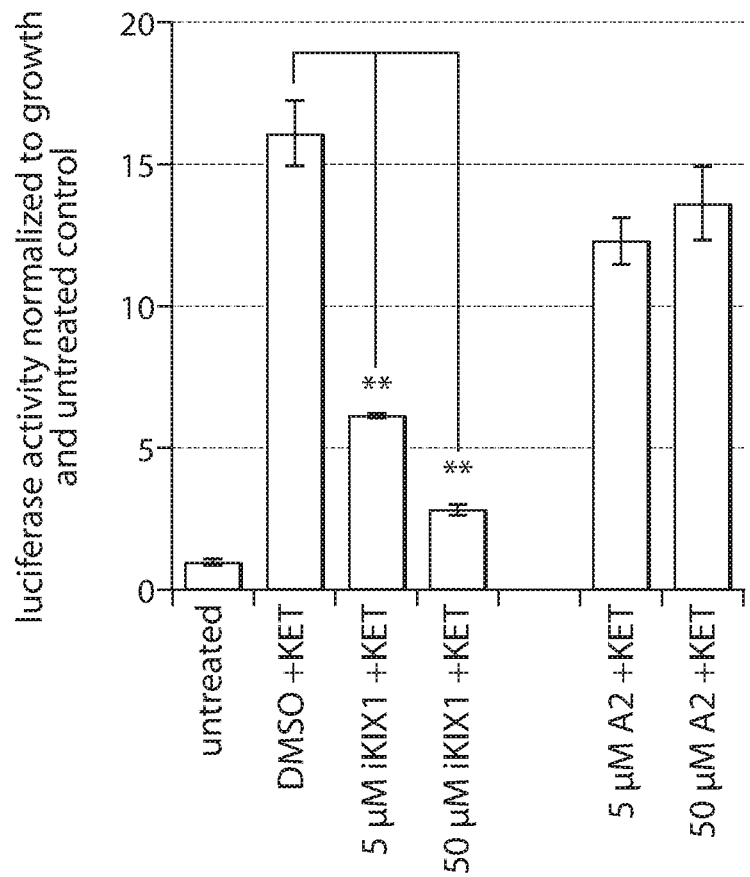
Figure 12C:
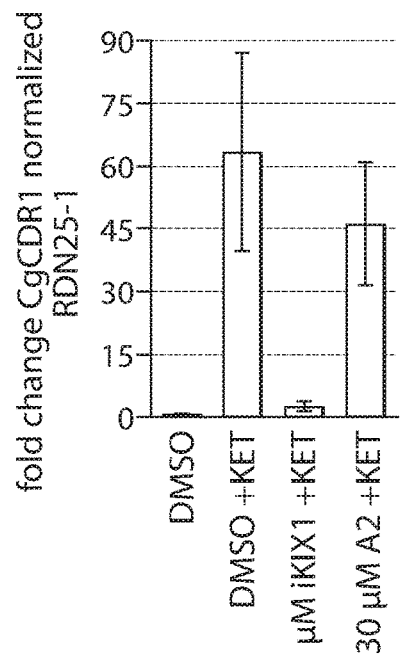
Figure 12D:
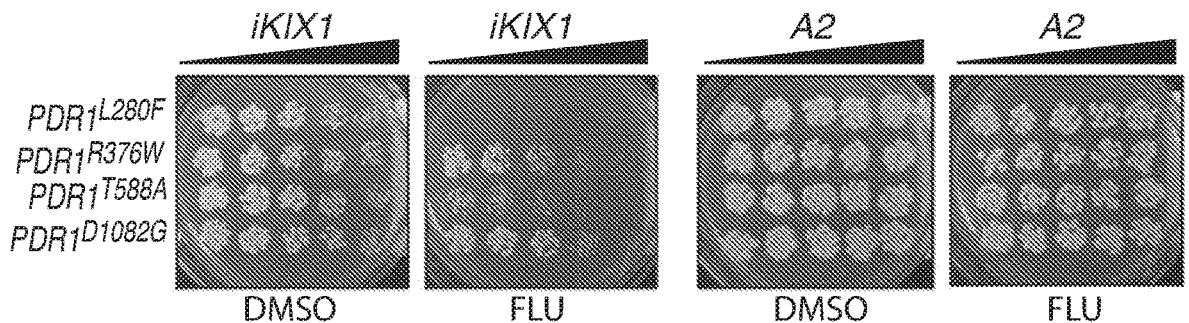
Figure 12E:
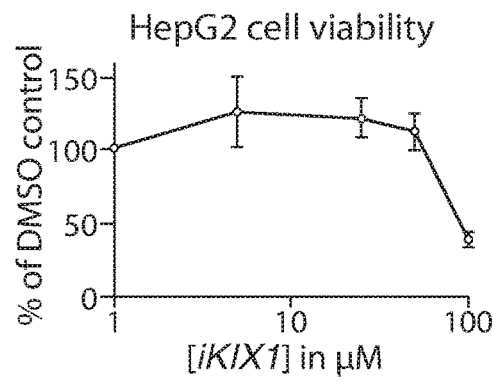
Figure 12F:
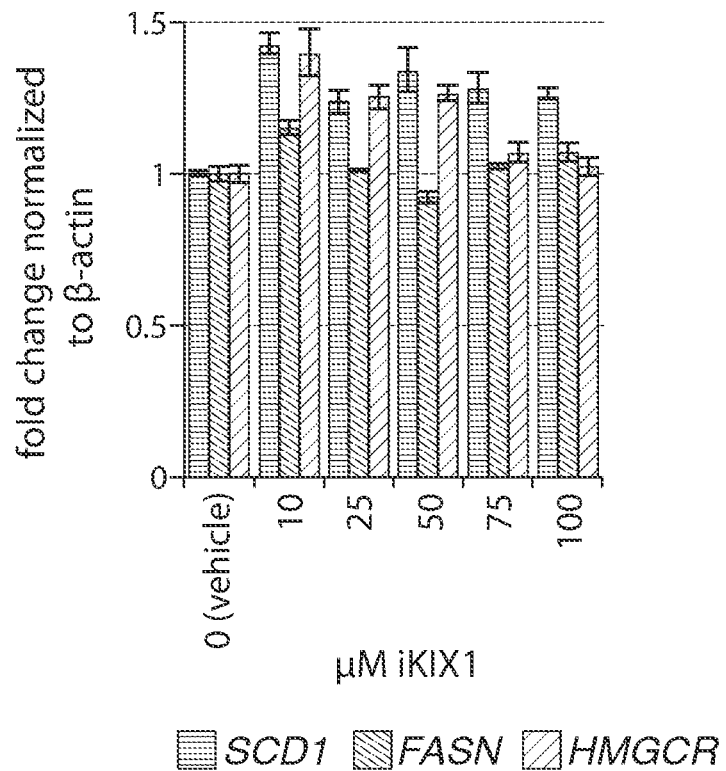
Figure 12G:
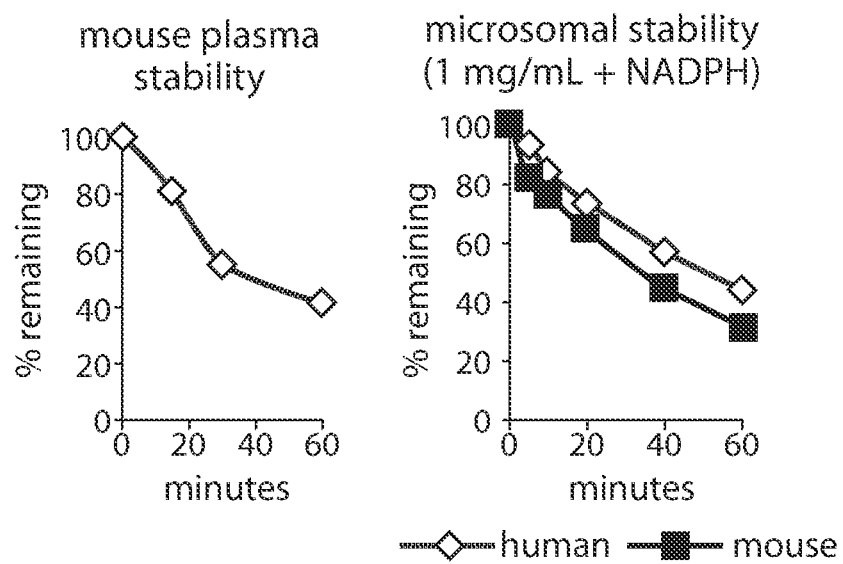

Prior to mammalian studies, the potential toxicity of iKIX1 was evaluated in mammalian cells (FIG. 12E, FIG. 12F). Human HepG2 cells treated with iKIX1 revealed toxicity only at high concentrations of iKIX1 (IC50~100 μM), iKIX1 had no effect on the transcription of SREBP-target genes at concentrations up to 100 μM, indicating its specificity for the fungal Gal11/Med15 KIX domain (see. e.g., Yang. F. et al. An ARC/Mediator subunit required for SREBP control of cholesterol and lipid homeostasis. Nature 442, 700-704 (2006)). Also assessed was the in vitro stability and in vivo mouse pharmacokinetics of iKIX1 and found that iKIX1 exhibited favorable drug-like properties and in vivo exposure in these studies (FIG. 13G, FIG. 13H).

Figure 4D:
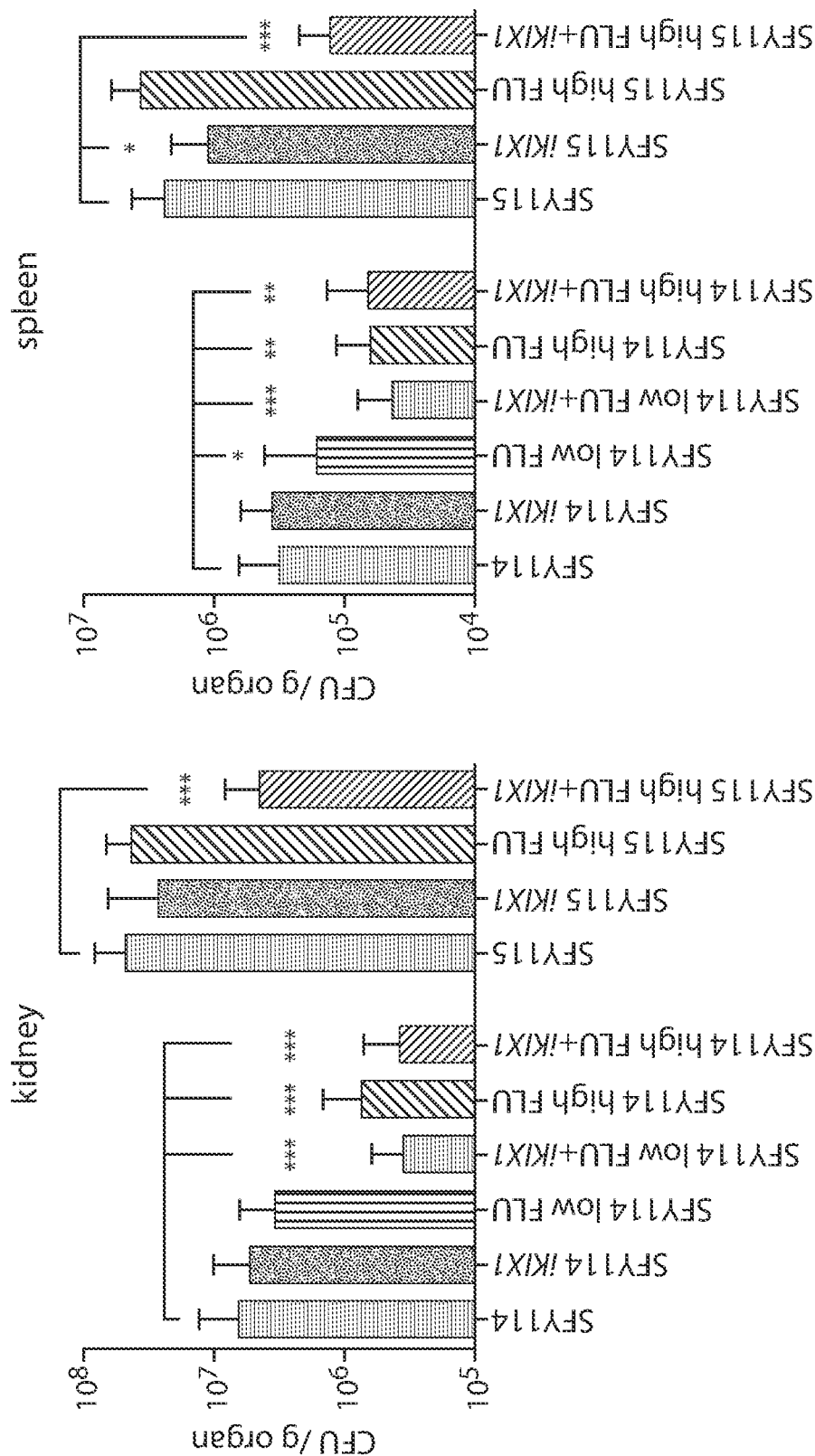
Figure 13A:
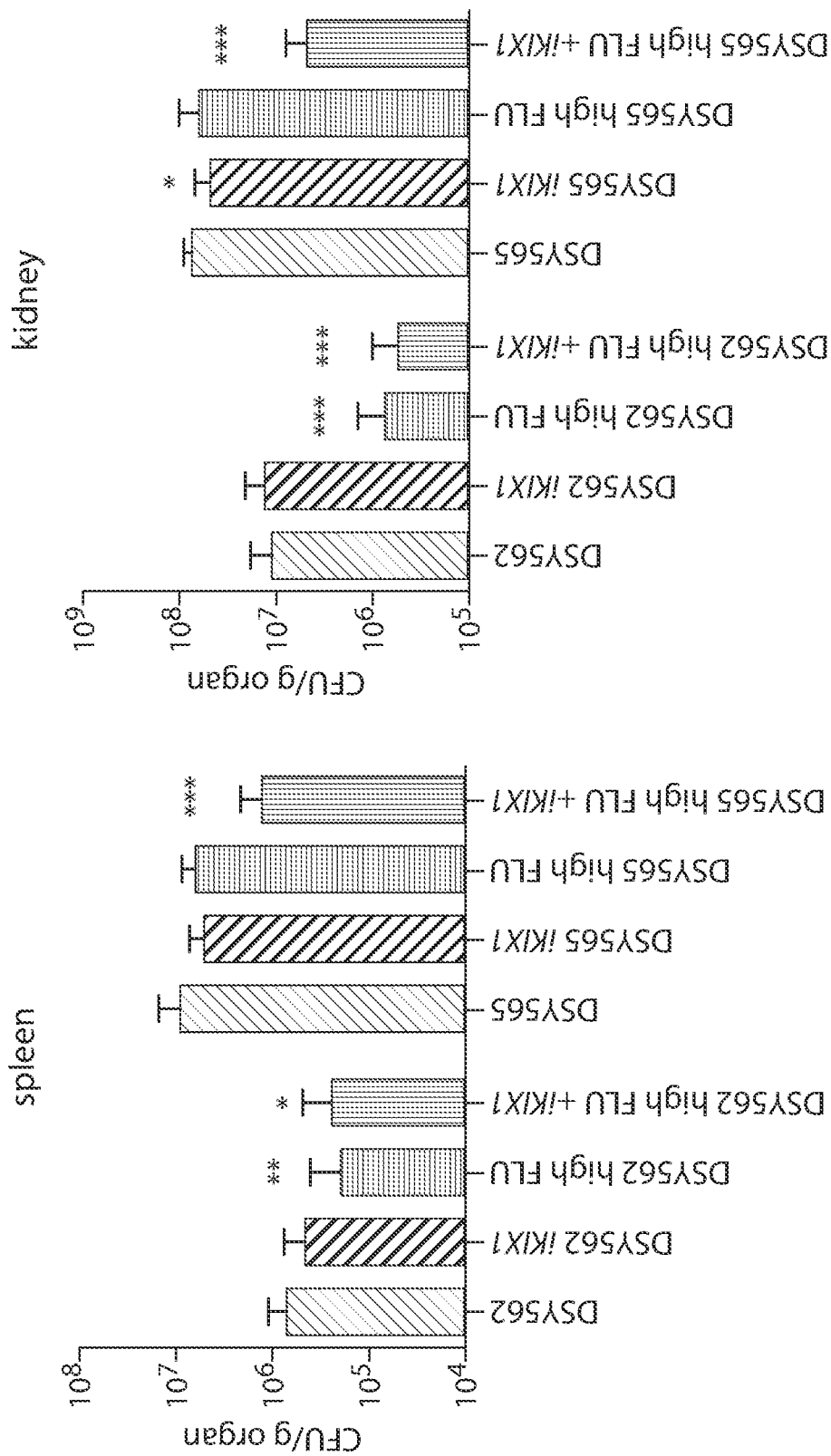
FIG. 13A. Clinical isolates DSY562/DSY565 (azole sensitive and PDR1$^{L280F}$ azole-resistant strains, respectively) behave similarly to SFY114/SFY115 (isogenic PDR1$^+$ and PDR1$^{L280F}$ strains, shown in FIG. 4d) in the mouse infection model, n=10 mice for each treatment condition; *P<0.01, P<0.005 and *P<0.0001.
Figure 13B:
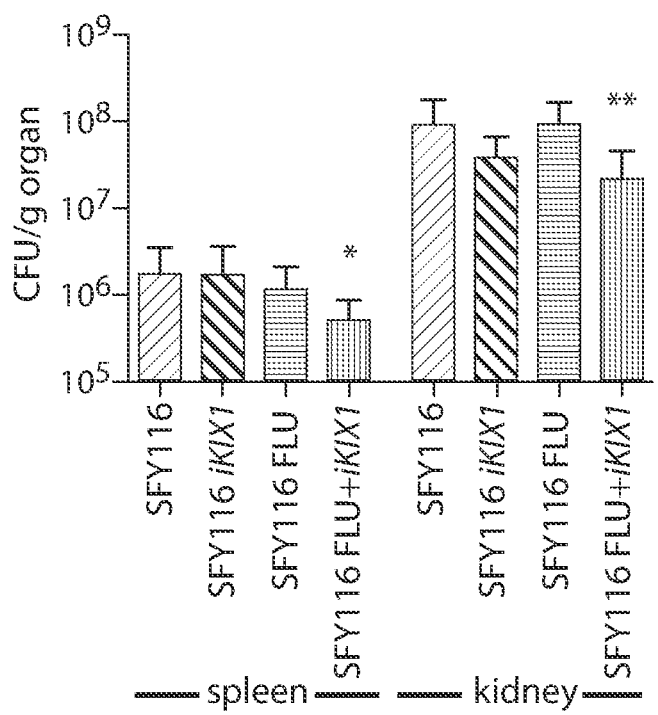
FIG. 13B, iKIX1 combination treatment with fluconazole reduces fungal tissue burdens in the spleen or kidney of mice injected with C. glabrata PDR1$^{P822}$L (SFY116). n=5 mice for each treatment condition; **P<0.01 and *P<0.05.
Figure 13C:
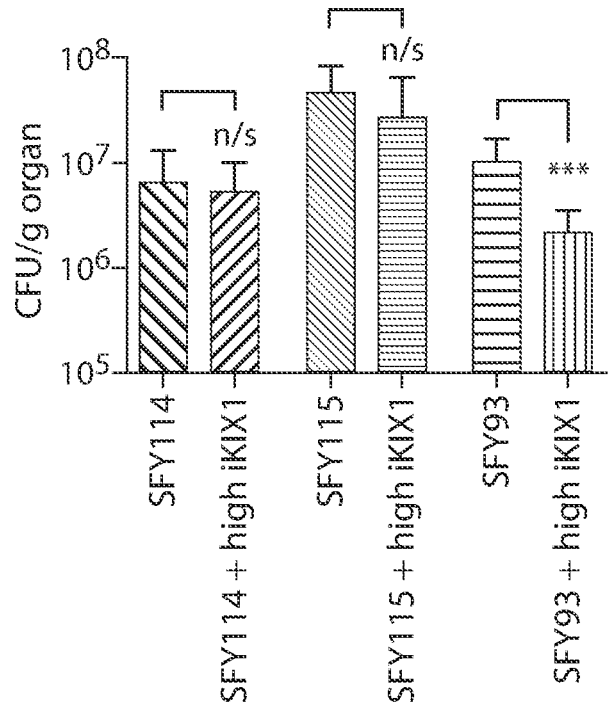
FIG. 13C. 100 mg/kg/day iKIX1 (high iKIX1) treatment of mice infected with SFY93 (pdr1Δ) significantly reduces fungal burden in a mouse infection model (CFU/g kidney) alone as compared to SFY114 (PDR1$^+$) or SFY115 (PDR1$^{L280F}$). n=10 mice for each treatment condition; *P<0.01, P<0.005, *P<0.0001.
Figure 13D:
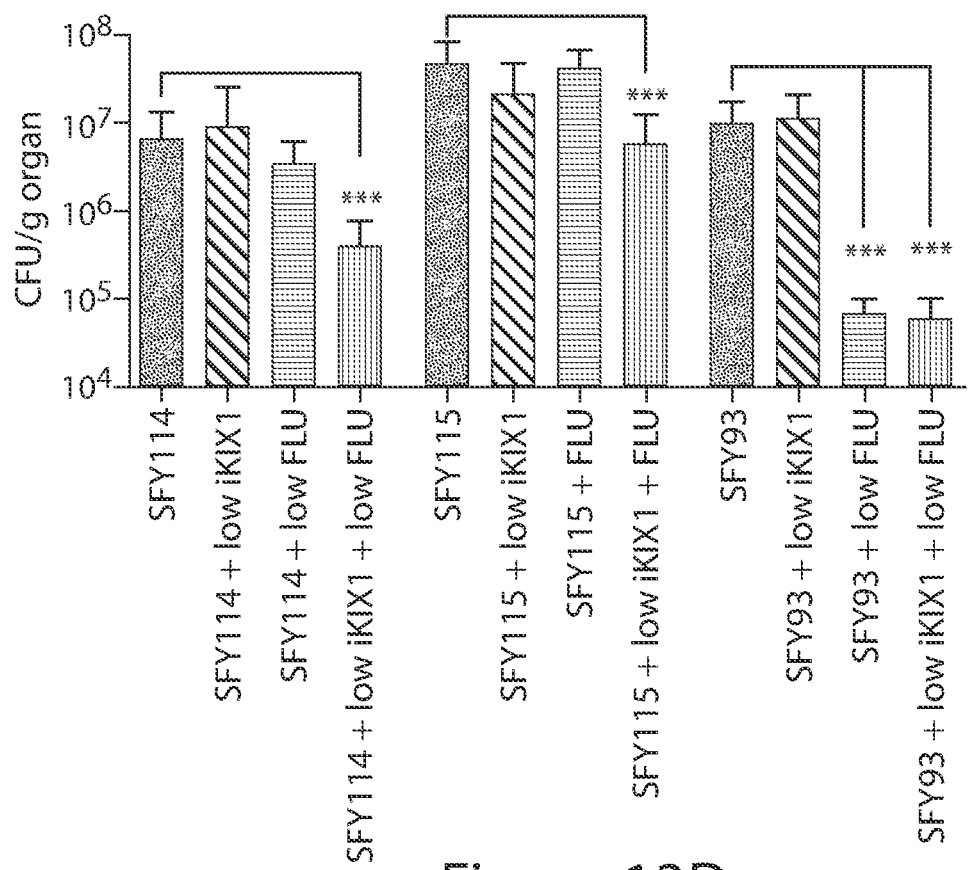
FIG. 13D. Mice infected with SFY114 (PDR1+), SFY115 (PDR1$^{L280F}$) or SFY93 (pdr1Δ) were treated with low (10 mg/kg/day) iKIX1, low fluconazole (low FLU; 25 mg/kg/day), fluconazole at 100 mg/kg/day (FLU) or combination with the two, iKIX1 did not confer additional reductions in CFU/g kidney with SFY93 infection. n=10 mice for each treatment condition. ***P<0.0005.

To evaluate the therapeutic potential of iKIX1 and azole antifungal co-therapy in a mammalian model, an established mouse model of disseminated fungal disease was used (see, e.g., Silva, L. V. et al. Milbemycins: more than efflux inhibitors for fungal pathogens. Antimicrobial agents and chemotherapy 57, 873-886, doi:0.1128/AAC.02040-12 (2013)). Mice were inoculated with *C. glabrata* by tail-vein injection and were dosed peritoneally once-daily with 100 mg/kg fluconazole (high FLU), 100 mg/kg iKIX1, a combination of the two, or vehicle alone. After 7 days, mice injected with a CgPDR1 wild-type strain exhibited significantly reduced tissue fungal burden in the kidney and spleen following fluconazole treatment alone; iKIX1 co-treatment did not result in further reductions (FIG. 4D). In contrast, in mice injected with the azole-resistant CgPDR1$^{L280F}$ strain, only co-treatment with iKIX1 and fluconazole resulted in significant (~10-fold) reductions in fungal burdens in the kidney and spleen (P<0.0001) (FIG. 4D). Similar results were observed with the clinically isolated CgPDR1$^+$ and CgPDR1$^{L280F}$ strains DSY562 and DSY565 (FIG. 13A). Consistent with previous studies, the fungal burden in mice infected with the CgPDR1$^{L280F}$ strain was higher than those infected with wild-type CgPDR1 strains, suggesting that PDR1 mutant strains may be more virulent in vivo (see, e.g., Silva, L. V. et al. Milbemycins: more than efflux inhibitors for fungal pathogens. *Antimicrobial agents and chemotherapy* 57, 873-886, doi:10.1128/AAC.02040-12 (2013)). Similar but less pronounced results were found in mice injected with a CgPDR1$^{P822L}$ strain (FIG. 13B). When mice were injected with a CgPDR1 wild-type strain and dosed with 25 mg/kg fluconazole (low FLU) alone or in combination with iKIX1, fluconazole alone poorly reduced tissue burden, whereas combination treatment resulted in significant (~10-fold) reductions in fungal burdens in both organs (P<0.0001) (FIG. 4D). These results suggest that iKIX1 combination treatment with azole may be therapeutically desirable even in the absence of CgPDR1 gain-of-function mutations. Mice infected with a Cgpdr1 null strain were more sensitive to iKIX1 alone; unlike mice infected with CgPDR1⁻ or CgPDR1$^{L280F}$ strains, low doses of iKIX1 did not further reduce fungal burden in Cgpdr1 null infections (FIG. 13C, FIG. 13D).

Figure 13E:
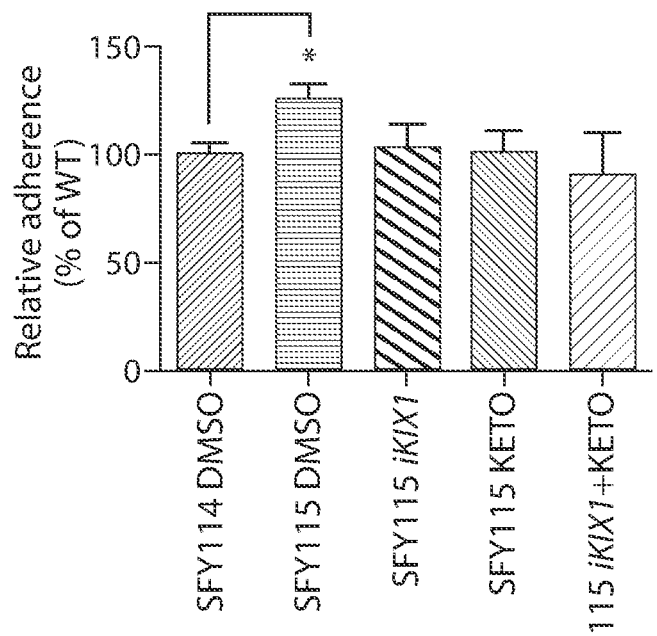
FIG. 13E, iKIX1 and ketoconazole (KETO) reduce adherence of CgPDR1$^{L280F}$ (SFY116) to CHO-Lec2 cells. Adherence is normalized to SFY114 DMSO control; each column represents the average of 4 biological replicates. *P<0.05 as compared to SFY114 DMSO control.
Figure 13F:
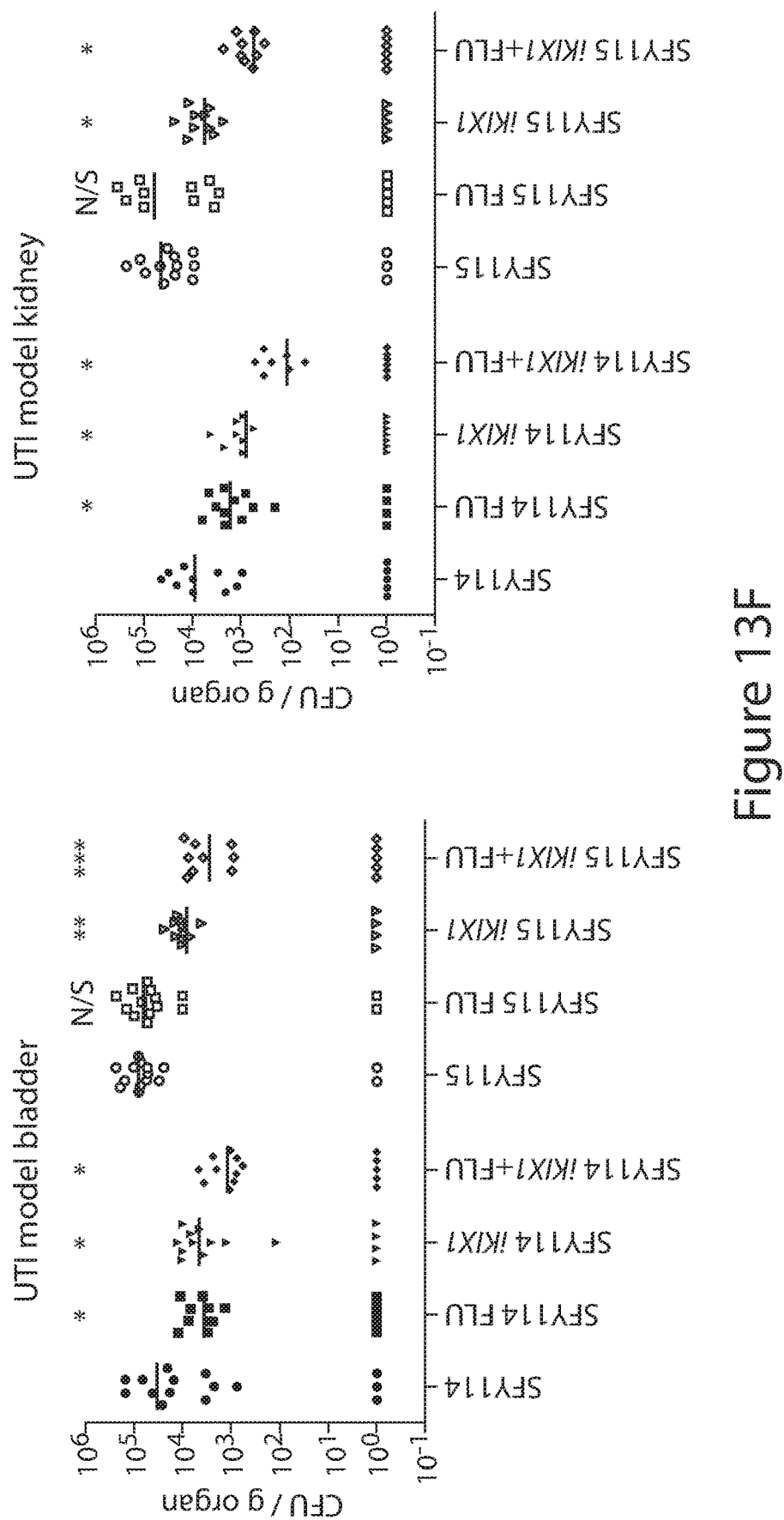
FIG. 13F, iKIX1 (100 mg/kg/day) or fluconazole (FLU) significantly reduces fungal burden in the bladder and kidney in a urinary tract infection model in mice. n=15 mice were infected in each group and points at 0 log$_{10}$ CFU/g organ fell below the detection limit of the method (50 CFU/g organ). *P<0.05, **P<0.005.

CgPDR1 gain-of-function mutations are also known to control adherence to host cells. As previously observed, a PDR1$^{L280F}$ mutant increased relative adherence to epithelial cells as compared to a PDR1 wild-type strain (see, e.g., Vale-Silva, L., Ischer, F., Leibundgut-Landmann, S. & Sanglard, D. Gain-of-function mutations in PDR1, a regulator of antifungal drug resistance in *Candida glabrata*, control adherence to host cells. *Infect Immun* 81, 1709-1720, doi: IAI.00074-13 [pii] 10.1128/IAI.00074-13). Strikingly, iKIX1 treatment alone reduced adherence to levels similar to a PDR1 wild-type strain (FIG. 13E). Ketoconazole alone or co-treatment with iKIX1 also reduced relative adherence to levels comparable to a PDR1 wild-type strain. To assess the role of iKIX1 in modulating adhesion in an infection model, a mouse model of urinary tract infection was used (see, e.g., Chen, Y. L. et al. Convergent Evolution of Calcineurin Pathway Roles in Thermotolerance and Virulence in *Candida glabrata*. G3 (Bethesda) 2, 675-691, doi:10.1534/g3.112.002279 GGG_002279 [pii]). In both the bladder and kidney, iKIX1 alone was sufficient to decrease fungal load after infection with either a PDR1 wild-type strain or a PDR1$^{L280F}$ strain (FIG. 13F), suggesting that iKIX1 may indeed modulate adhesion.

Figure 14:
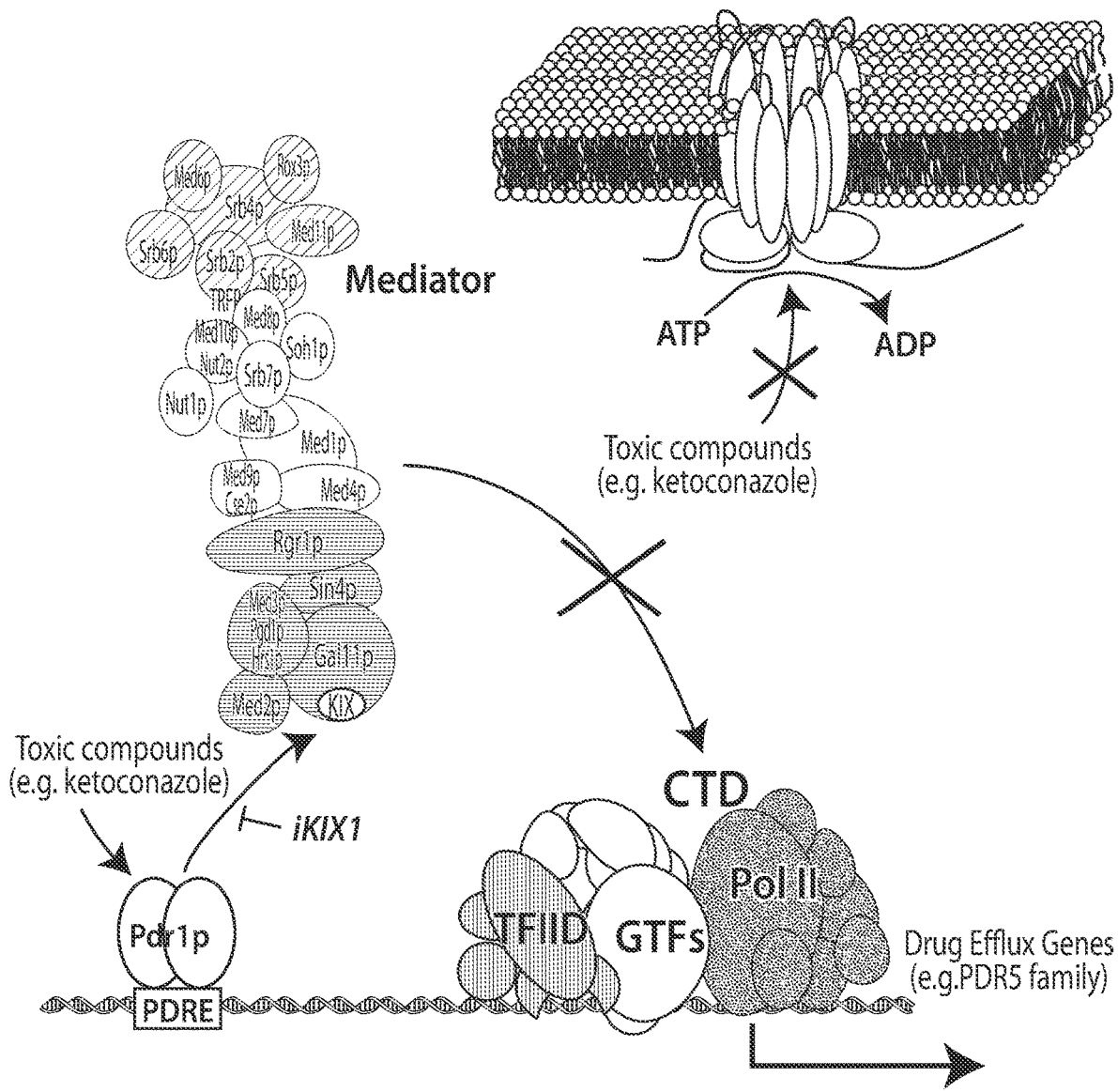
FIG. 14 shows model of iKIX1 function as a co-therapeutic in combination with an azole, blocking the azole-induced recruitment of Gal11/Med15-Mediator to Pdr1 target genes upon azole-treatment and preventing the upregulation of Pdr1 target genes, including those which encode drug efflux pumps.
Figure 15:
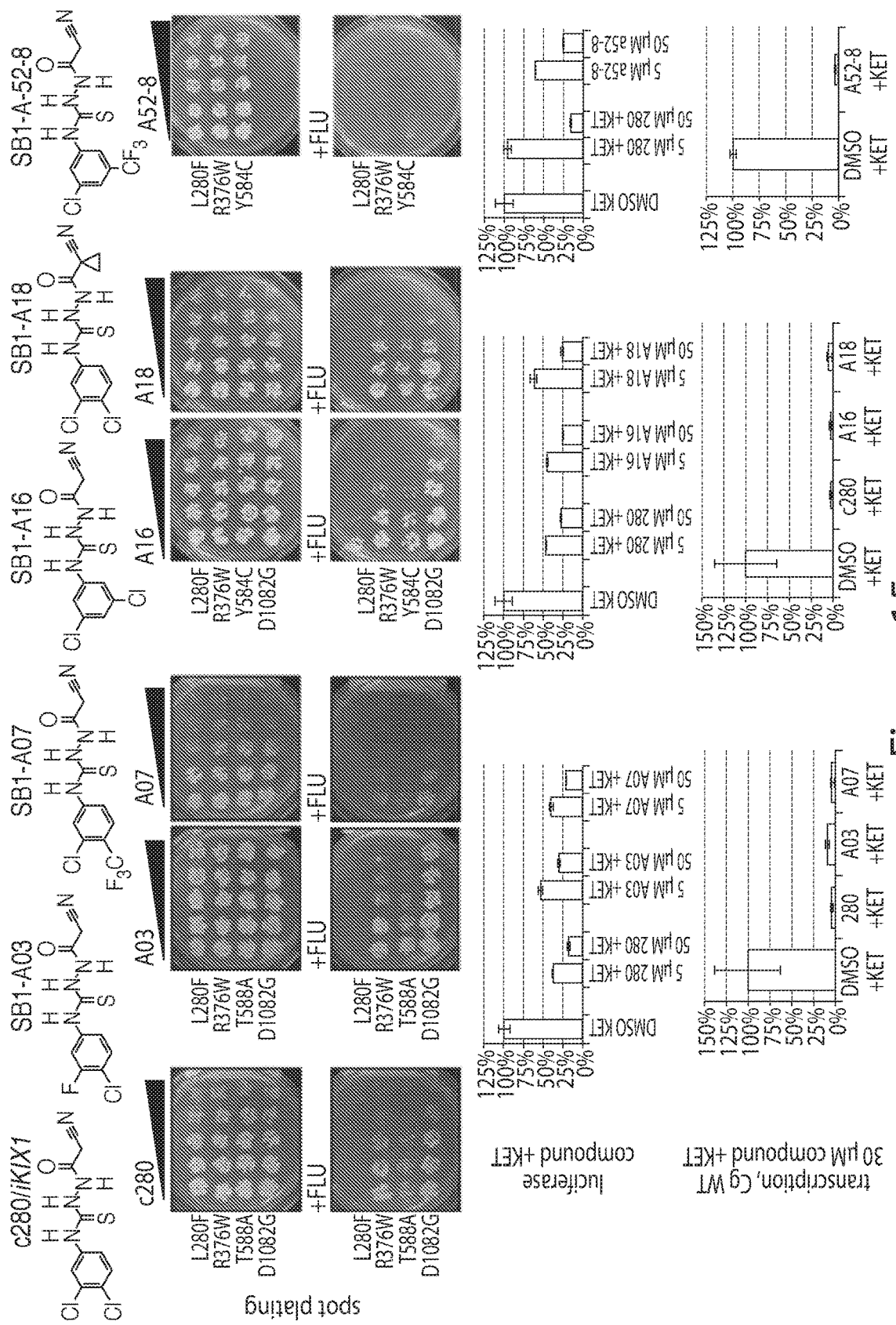
Figure 18:
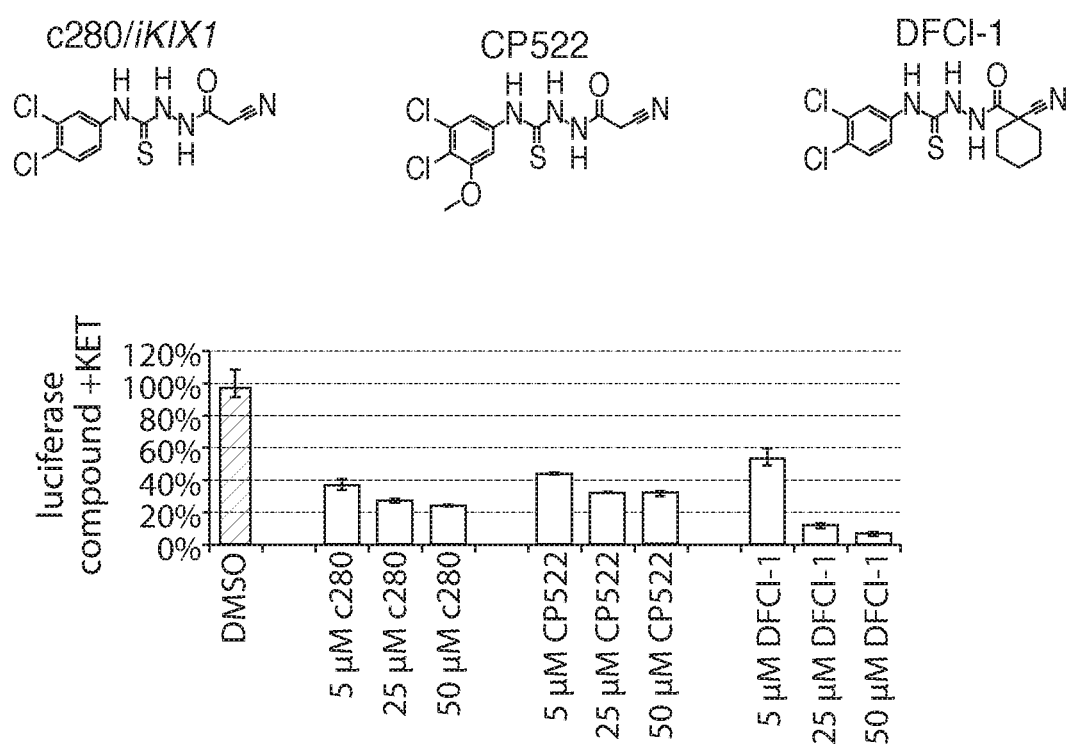

The proportion of azole-resistant *C. glabrata* (up to 20% in the US) and the emergence of multidrug resistance (approximately 40% of echninocandin-resistant isolates are azole-resistant) argues for the need for novel treatments that can target these resistant populations (see, e.g., Farmakiotis, D., Tarrand, J. J. & Kontoyiannis, D. P. Drug-Resistant *Candida glabrata* Infection in Cancer Patients. *Emerg Infect Dis* 20, 1833-1840, doi:10.3201/eid2011.140685; Pfaller, M. A. et al. Frequency of decreased susceptibility and resistance to echinocandins among fluconazole-resistant bloodstream isolates of *Candida glabrata*. *J Clin Microbiol* 50, 1199-1203, doi:JCM.06112-11 [pii] 10.1128/JCM.06112-11). The results herein demonstrate that small molecule disruption of the interaction between the CgGal11A KIX domain and the CgPdr1 activation domain is a therapeutically tractable method for treating infectious diseases (e.g., fungal infections), including resensitizing azole-resistant *C. glabrata* to standard azole antifungal treatment (FIG. 14).

Additional Biological Data

TABLE 1

| Compound Structure | MW | Luciferase activity (5 μM + keto) (% DMSO + keto) | Luciferase activity (50 μM + keto) (% DMSO + keto) | CgCDR1 qRT-PCR (30 μM in PDR1 WT) (% DMSO + keto) | CgCDR1 qRT-PCR (% DMSO + keto) |
|---|---|---|---|---|---|
| 3,4-dichlorophenyl-NH-C(=S)-NH-NH-C(=O)-C(cyclopropyl)(CN) | 329.2 | 62 | 25 | 5 | 10 μm – 12%<br>30 μm – 5% |
| 3-fluoro-4-chlorophenyl-NH-C(=S)-NH-NH-C(=O)-CH₂-CN | 286.71 | 54 | 30 | — | 10 μm – 74%<br>30 μm – 42% |
| 3-chloro-4-trifluoromethylphenyl-NH-C(=S)-NH-NH-C(=O)-CH₂-CN | 336.72 | 40 | 21 | — | 10 μm – 10%<br>30 μm – 3% |

TABLE 1-continued

| Compound Structure | MW | Luciferase activity (5 μM + keto) (% DMSO + keto) | Luciferase activity (50 μM + keto) (% DMSO + keto) | CgCDR1 qRT-PCR (30 μM in PDR1 WT) (% DMSO + keto) | CgCDR1 qRT-PCR (% DMSO + keto) |
|---|---|---|---|---|---|
| 3,5-dichlorophenyl thiosemicarbazide cyanoacetyl | 303.17 | 45 | 25 | — | 10 μm – 17%<br>30 μm – 7% |
| 3-chloro-5-trifluoromethylphenyl thiosemicarbazide cyanoacetyl | 302.18 | 77 | 28 | — | 30 μm – 3% |
| 3,4-dichlorophenyl thiosemicarbazide cyano(phenyl)acetyl | — | 86 | 38 | — | 30 μm – 1% |
| 3,4-dichlorophenyl thiosemicarbazide 1-cyanocyclohexanecarbonyl | — | 53 | 14 | — | 10 μm – 10%<br>30 μm – 2% |
| 3,4-dichloro-5-methoxyphenyl thiosemicarbazide cyanoacetyl | — | 52 | 26 | — | 10 μm – 15%<br>30 μm – 6% | iKIX1 and analogs that show antifungal activity in *Candida glabrata* also show antifungal activity in other clinically relevant pathogenic *Candida* species including *Candida albicans, Candida krusei, Candida tropicalis* and *Candida parapsilosis*. Antifungal susceptibility testing was carried out using broth dilution assays which examined effects of two-fold dilutions of compounds on cellular growth. The minimum inhibitory concentration (MIC) was defined as the drug concentration at which the optical density was equal to or decreased more than 50% from that of the drug-free culture. MIC shown in the table are in μM. (Table 2 and Table 3).

TABLE 2

| compound/analog | compound structure | yeast *Candida glabrata* DSY562 clinical isolate, azole sensitive, PDR1 wild type | *Candida glabraia* DSY565 clinical isolate, azole resistant, PDR1$^{1.280F}$ mutant | *Candida albicans* SC5314 ATCC strain SC5314 | *Candida albicans* DSY2621 deleted for efflux transporters and calcineurin subunit A |
|---|---|---|---|---|---|
| iK1X1 | | 12.5 | 12.5 | 12.5 | 12.5 |
| A02 (inactive analog, negative control) | | >100 | >100 | >100 | >100 |
| A18 | | 6.25 | 12.5 | 6.25 | 6.25 |
| A52-8 | | 3.125 | 6.25 | 3.125 | 3.125 |
| DFCI-1 | | 6.25 | 6.25 | 6.25 | 12.5 |
| A03 | | 12.5 | 25 | 25 | 25 |
| A07 | | 3.125 | 3.125 | 3.25 | 3.25 |

TABLE 2-continued
| | | | | | |
|---|---|---|---|---|---|
| A16 |  | 3.125 | 6.25 | 6.25 | 6.25 |
TABLE 3
| yeast | | Candida krusei | Candida tropicalis | Candida parapsilosis | Saccharomyces cerevisiae |
|---|---|---|---|---|---|
| strain | | DSY471 | DSY472 | DSY473 | DSY2094 |
| compound/ analog | compound structure | ATCC strain 6258 | ATCC strain 75/44508 | ATCC strain 22019 | — |
| iK1X1 | 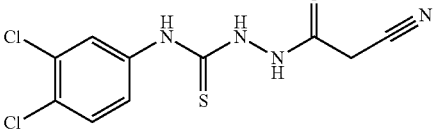 | 6.25 | 6.25 | 25 | 12.5 |
| A02 (inactive analog, negative control) | 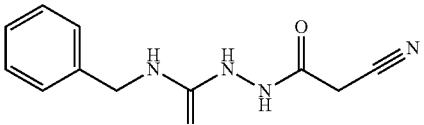 | >100 | >100 | >100 | >100 |
| A18 | 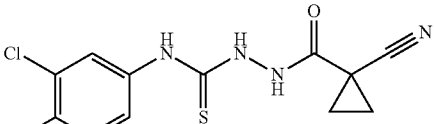 | 6.25 | 12.5 | 25 | 12.5 |
| A52-8 | 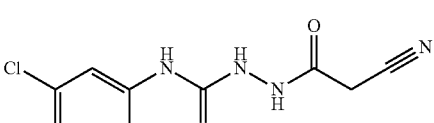 | 3.125 | 3.125 | 12.5 | 3.125 |
| DFCI-1 |  | 3.125 | 6.25 | 12.5 | 6.25 |
| A03 | 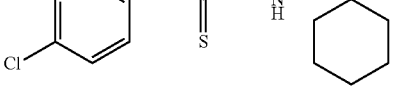 | 12.5 | 12.5 | 50 | 12.5 |

TABLE 3-continued

| | | | | | |
|---|---|---|---|---|---|
| A07 | [structure: Cl and F3C substituted phenyl-NH-C(=S)-NH-NH-C(=O)-CH2-C≡N] | 6.25 | 3.25 | 6.25 | 3.125 |
| A16 | [structure: 3,5-dichlorophenyl-NH-C(=S)-NH-NH-C(=O)-CH2-C≡N] | 3.25 | 3.25 | 12.5 | 3.125 |

Biological Materials and Methods

Fluorescence Polarization-Based High-Throughput Screen

A fluorescein-tagged 30 amino acid C-terminal activation domain of CgPdr1 (FITC-LGTLDEFVNKGDLNE-LYNSLWGDLFSDVYL (SEQ ID NO: 1)) CgPdr1 AD30 was purchased as a synthetic peptide from Pepide2.0. The CgGal11A KIX domain was expressed as a His$_6$-GST fusion protein and purified by affinity chromatography with Ni-NTA resin (Qiagen) and size exclusion chromatography (Sephadex 75, Pharmacia). The $K_d$ for CgPdr1 AD30 binding to CgGal11A KIX was determined to be 320 nM by fluorescence polarization (FP) assay. For small molecule screening, fluorescein-CgPdr1 AD30 was held at a concentration of 30 nM and the GST-tagged CgGal11A KIX was at a concentration of 1 μM (above the Kd). The screen was carried out in duplicate and the volume in each well was 25 μL.

Hit Identification

The Z-score for Fluorescence Polarization and Total Fluorescence was determined for each individual plate. To filter out false positives arising from the auto-fluorescence of the compounds and allow strict filtering for the initial cherry picks, the mean was calculated only from wells without compound. Standard deviation of Fluorescence Polarization was calculated using the readings from the entire plate, whereas standard deviation of Total Fluorescence was calculated using wells without compound. For cherry picking for the in vivo screen only those compounds that exhibited a Z-score greater than 4 in Fluorescence Polarization, and a Z-score of less than 3 in Total Fluorescence, with values consistent between both samples, were considered.

CgPdr1 AD Kd and Titration with iKIX1

To measure the dissociation constant (Kd) of CgPdr1 AD30, FITC labeled CgPdr1 AD30 was held at a concentration of 30 nM and the GST-tagged CgGal11A KIX was prepared with concentrations ranging from 0 to 300 μM. The IC50 for iKIX-1 binding was measured with GST-tagged CgGal11A KIX held at a constant 3 μM concentration, iKIX-1 was titrated from 0 to 1000 μM and 30 nM FITC-labeled CgPdr1 AD30 was added subsequently with an HP D300 digital dispenser (Tecan Group. Maennerdorf, Switzerland). All experiments were carried out in duplicate and the s.d. is reported at each point on the plot.

Analysis of CgPdr1 AD and iKIX1 Binding to CgGal11A KIX

The FP titration curve of the CgPdr1 AD30 was fitted to GraphPad Prisms (La Jolla, Calif., USA) One site-total binding equation (equation 1).

$$Y = \frac{B\max * X}{(K_d + X)} + NS * X + \text{Background} \quad (1)$$

Where Bmax is the maximum specific binding, Kd is the equilibrium binding constant. NS is the slope of nonspecific binding and Background is the amount of nonspecific binding. The curve of the competition assay with iKIX1 was fitted to a decaying exponential (equation 2) in MATLAB (Natick, Mass., USA) and a 190.2 μM IC$_{50}$ was obtained.

$$Y = A * e^{(-b*x^n)} + c \quad (2)$$

Subsequently, this IC$_{50}$ was used to calculate an apparent inhibition constant (Ki) of 18.1 μM for iKIX1 binding; according to a procedure described by Cer and colleagues (see, e.g., Cer R Z, Mudunuri U, Stephens R, Lebeda F J. IC50-to-Ki: a web-based tool for converting IC$_{50}$ to Ki values for inhibitors of enzyme activity and ligand binding. Nucleic acids research. 2009; 37(Web Server issue):W441-5. PMCID: 2703898) (equation 3).

$$K_i = \frac{I_{50}}{\frac{L_{50}}{K_d} + \frac{P_0}{K_d} + 1} \quad (3)$$

Where Ki is the inhibitor concentration, IC$_{50}$ is the concentration of the free inhibitor (iKIX1) at 50% inhibition, L50 is the concentration of the free ligand (CgPdr1 AD30) at 50% inhibition, $K_d$ is the dissociation constant of fluorescein-CgPdr1 AD30 to GST-tagged CgGal11A KIX and P$_0$ is the concentration of the free protein at 0% inhibition.

Cell Growth Inhibition Screen

S. cerevisiae SEY6210 wild-type strains were grown in YPD (U % yeast extract, 2% bacto peptone, 2% dextrose) at 30° C. with shaking overnight until saturation. The next day, cultures were inoculated to an OD$_{600}$ of 0.0007 and grown for 17 hours, to an OD$_{600}$~0.5, 384-well plates were set up in duplicate with either YPD alone or with YPD containing a final concentration of 5 μM ketoconazole. 384-well plates contained 5 two-fold dilutions of each compound, corresponding to a final concentration range of 20 μg/mL to 1.25 μg/mL. Wells were inoculated with cells to a final OD$_{600}$ of 0.00025 in YPD. To identify compounds that potentiate azole inhibition of cell growth, cells were allowed to grow for another 45 hours followed by OD$_{600}$ measurement on an Envision plate reader (Perkin Elmer).

NMR Methods

The sequence corresponding to the CgGal11A KIX domain was cloned into a pET24b plasmid with an N-terminal His6-tag and was transformed into *E. coli* BL21 (DE3) cells. Cells were grown in $^{15}$N, $^{15}$N/$^{13}$C enriched minimal media at 37 C. The cells were induced at an $OD_{600}$ of 0.7 with 1 mM isopropyl β-D-1-thiogalactopyranoside at 25 C. The cells were then lysed by sonication after addition of 1 mg/mL lysozyme. The protein was affinity purified using Ni-NTA resin (Qiagen) and further purified by fast protein liquid chromatography using a size exclusion column (Sephadex 75. Pharmacia). All NMR samples were in PBS buffer (10 mM Na2HPO$_4$, 2 mM K2HPO$_4$, 137 mM NaCl, 2.7 mM KCl, 1 mM EDTA and 0.01% NaN$_3$), pH 6.5, unless otherwise stated. The samples were measured at a concentration of approximately 800 μM.

Backbone assignments were obtained by the standard set of triple resonance experiments (HNCA/HNCOCA, HNCACB/CBCACONH, HNCO/HNCACO) and side-chain resonances were assigned using HCCONH and CCONH experiments in H$_2$O and HCCH-TOCSY in $^2$H$_2$O. Distance constrains were obtained from $^{15}$N- and $^{13}$C-dispersed Nuclear Overhauser Enhancement (NOE) experiments with mixing times of 90 milliseconds and 80 milliseconds, respectively. Stereo-specific methyl assignments were obtained with a stereo-specific methyl (ILV) labeling strategy developed by the Boisbouvier group (see, e.g., Gans P, Hamelin O, Sounier R, Ayala I, Dura M A, Amero C D, et al. Stereospecific isotopic labeling of methyl groups for NMR spectroscopic studies of high-molecular-weight proteins. Angewandte Chemie. 2010; 49(11): 1958-62).

Structure Calculation and Refinement

Peak volumes were integrated and converted to distance restraints in the CcpNmr software suite (see, e.g., Vranken W F, Boucher W, Stevens T J, Fogh R H, Pajon A, Llinas M. et al. The CCPN data model for NMR spectroscopy: development of a software pipeline. Proteins. 2005; 59(4):687-96). One hundred structures were calculated with CYANA and the 10 lowest energy structures were selected for AMBER refinement in explicit water (see, e.g., Guntert P. Automated NMR structure calculation with CYANA. Methods in molecular biology. 2004: 278:353-78). The refinement was performed through the WeNMR web-interface with the AMBER99SB force field, TIP3PBOX and a box distance of 10 Ångstrom (Å) (see, e.g., Bertini I, Case D A, Ferella L, Giachetti A, Rosato A. A Grid-enabled web portal for NMR structure refinement with AMBER. Bioinformatics. 2011; 27(17):2384-90). The quality of the CgGal11A KIX structure was analyzed and validated with the protein structure validation software suite PSVS, the common interface for NMR structure generation (CING) and Procheck-NMR (see, e.g., Bhattacharya A, Tejero R, Montelione G T. Evaluating protein structures determined by structural genomics consortia. Proteins. 2007; 66(4):778-95: Doreleijers J F, Sousa da Silva A W, Krieger E, Nabuurs S B, Spronk C A, Stevens T J. et al. CING: an integrated residue-based structure validation program suite. Journal of biomolecular NMR, 2012; 54(3):267-83. PMCID: 3483101; Laskowski R A, MacArthur M W, Moss D S, Thornton J M. PROCHECK: a program to check the stereochemical quality of protein structures. Journal of Applied Crystallography, 1993; 26(2):283-91). 96.1% of dihedral (φ and ψ) angles occupy the core region of the Ramachandran plot, and 3.6% are in the allowed, 0.3% in the generously allowed and none in the disallowed region.

Chemical Shift Perturbation (CSP) Analysis

CSPs in $^1$H-$^{15}$N HSQCs and $^1$H-$^{13}$C ILV HSQCs of CgGal11A KIX domain were calculated according to equations 4a and 4b, respectively.

$$CSP=[(\Delta proton\ shifts)^\wedge+(\Delta nitrogen\ shifts*0.2)^\wedge]^\wedge 0.5 \quad (4a)$$

$$CSP=[(\Delta proton\ shifts)^\wedge+(\Delta carbon\ shifts*0.3)^\wedge]^\wedge 0.5 \quad (4b)$$

Residues that experienced a CSPs larger than two the standard deviation were considered to be significant and plotted on the structure of the CgGal11A KIX domain. Residues with significant $^1$H-$^{15}$N CSPs are (L23, M24, N27, I29, N30, G31, T35, T36, A37, M40, H43, A44, A49, L51, K54, M65, K68, I69, M72, R73, T75, R76, R79, E82, S83) and (L23, M24, D25, I26, N27, I29, N30, T35, T36, A37, H43, A44, L51, K66, R73, T75, E82) for the CgPdr1AD and iKIX1, respectively. L19, L23 and L51 showed significant ILV CSPs in both titrations.

Ligand Docking

The position of the ligand binding cavity site on the CgGal11A KIX domain was obtained by center of mass calculation of the amino acid residues 10-30, 35-54 and 59-83. In the next step, partial atomic charges and other force field parameters were assigned to the CgGal11A KIX domain with the AMBER 14 force field (see, e.g., D. A. Case J T B, R. M. Betz, D. S. Cerutti, T. E. Cheatham, III. T. A. Darden, R. E. Duke. T. J. Giese, H. Gohlke. A. W. Goetz, N. Homeyer, S. Izadi, P. Janowski, J. Kaus, A. Kovalenko, T. S. Lee, S. LeGrand, P. Li, T. Luchko, R. Luo, B. Madej, K. M. Merz, G. Monard, P. Needham, H. Nguyen, H. T. Nguyen. I. Omelyan, A. Onufriev, D. R. Roe, A. Roitberg, R. Salomon-Ferrer, C. L. Simmerling, W. Smith, J. Swails, R. C. Walker. J. Wang, R. M. Wolf, X. Wu, D. M. York and P. A. Kollman. AMBER 2015. University of California, San Francisco 2015). Partial atomic charges and other force field parameters were assigned to iKIX-1 with the AM1-BCC method and GAFF, respectively (see, e.g., Jakalian A, Jack D B, Bayly C I. Fast, efficient generation of high-quality atomic charges. AM1-BCC model: II. Parameterization and validation. Journal of computational chemistry. 2002; 23(16): 1623-41; Wang J, Wolf R M, Caldwell J W, Kollman P A. Case D A. Development and testing of a general amber force field. Journal of computational chemistry. 2004; 25(9): 1157-74). Docking and scoring of iKIX1 with CgGal11A KIX was carried out using the Pardock and BAPPL modules of Sanjeevini, an automated, linux based freely accessible drug design software suite (see, e.g., Gupta A, Gandhimathi A, Sharma P. Jayaram B. ParDOCK: an all atom energy based Monte Carlo docking protocol for protein-ligand complexes. Protein and peptide letters. 2007; 14(7):632-46; Jain T, Jayaram B. An all atom energy based computational protocol for predicting binding affinities of protein-ligand complexes. FEBS letters. 2005:579(29):6659-66; Jayaram B, Singh T. Mukherjee G, Mathur A, Shekhar S. Shekhar V. Sanjeevini: a freely accessible web-server for target directed lead molecule discovery. BMC bioinformatics. 2012; 13 Suppl 17:S7. PMCID: 3521208). The Pardock docking software samples a number of configurations of the ligand in the binding pocket of the protein and finally provides the top energetically favorable configurations of the ligand bound to the KIX domain. These protein-ligand complexes are then subjected to energy minimization in vacuum with 1000 steps of steepest descent and 1500 steps of conjugate gradient methods using the SANDER module of AMBER 14. The binding free energy of iKIX1, estimated through docking and scoring, is −9.30 kcal/mol.

Chromatin Immunoprecipitation (ChIP) Assays

ChIP was performed according to standard procedures (see. e.g., McConnell A D, Gelbart M E, Tsukiyama T. Histone fold protein Dls1p is required for Isw2-dependent chromatin remodeling in vivo. Mol Cell Biol. 2004; 24(7): 2605-13. PMCID: 371119). Briefly, cells were grown to saturation then washed 2 times with sterilized Milli-Q (Millipore) water, resuspended to an $OD_{600}$ of 0.8 in YP (1% yeast extract, 2% bacto peptone) and then grown for 6 hours at 30° C. with shaking in the presence of DMSO (vehicle) or iKIX1. Cultures were induced with ketoconazole to a final concentration of 40 µM and harvested at the times indicated. 2 mL of culture was harvested at 0' and 15' for matched transcription samples; RNA was prepared as described below. Cells were fixed with 1% formaldehyde (final) for 15 minutes with swirling and then quenched with 125 mM glycine (final) for 5 min. with swirling. Cells were pelleted, washed with TBS+125 mM glycine and then TBS. Cells were lysed in buffer containing 50 mM HEPES, pH 7.5, 140 mM NaCl, 1% Triton X-100, 0.1% sodium deoxycholate, 1 mM EDTA and protease inhibitors and 0.5 mm glass beads. Glass beads were removed by centrifugation before cell lysate was sonicated to obtain 150 to 400 base pair fragments. Chromatin from clarified extracts was immunoprecipitated with HA.11 clone 16B12 monoclonal antibody (Covance MMS—101R) and protein G Dynabeads (Thermo Fisher Scientific) or protein G Dynabeads alone then washed with lysis buffer, high salt lysis buffer, wash buffer and TE, twice each before being eluted from beads in elution buffer at 65° C. for 30 min. Crosslinks were reversed in eluates at 65° C. for 5 hours in the presence of RNase A to 0.2 mg/mL followed by proteinase K treatment 0.2 µg/mL for 2 hours at 42° C. DNA was cleaned and eluted into TE using the Qiagen QIAquick PCR purification kit. No significant Gal11/Med15-HA or HA-Pdr1 association was observed with control genomic region (chr1) or in the absence of HA antibody.

Luciferase Assay

An *S. cerevisiae* pdr1Δ::KANpdr3Δ::KAN strain bearing plasmids carrying CgPDR1-1 and PDRES-luciferase was used for the luciferase assays. Strains were grown overnight in YPD and then washed twice with sterilized Milli-Q water before being resuspended to an $OD_{600}$ of 0.8 in YP. After 20 hours, cultures were split and iKIX1 or DMSO alone were added to final concentrations as indicated. At the same time, ketoconazole to a final concentration of 40 µM (resuspended in ethanol) or ethanol alone (vehicle) were added to cultures. After 24 hours of treatment, an equal volume of 1 mM d-luciferin (sodium salt) in 0.1 M sodium citrate buffer at pH 5.0 was added to 100 µL aliquots (see, e.g., Leskinen P, Virta M, Karp M. One-step measurement of firefly luciferase activity in yeast. Yeast. 2003; 20(13):1109-13). Luminescent signal was acquired over 10 seconds and RLU (relative light units) presented are normalized to growth (assessed by $OD_{600}$) and untreated controls.

Spot Plating

Strains were inoculated & grown in YPD at 30° C. with shaking overnight and 5 mL of YPD was inoculated with 20 µL of overnight culture. Strains were grown to log phase at 30° C. with shaking and then diluted to an $OD_{600}$ of 0.0004, 3 µL of cell suspension was spotted on plates containing gradients with increasing concentration of iKIX1 or vehicle (DMSO), and a fixed concentration of ketoconazole or fluconazole, as indicated. Gradients were made as previously described (see. e.g., Katzmann D J, Hallstrom T C, Voet M, Wysock W, Golin J, Volckaert G, et al. Expression of an ATP-binding cassette transporter-encoding gene (YOR1) is required for oligomycin resistance in *Saccharomyces cerevisiae*. Mol Cell Biol. 1995; 15(12):6875-83. PMCID: 230942). Plates were incubated at 30° C. and growth was assessed after 48 hours.

Minimal Inhibitory Concentration (MIC) Assays iKIX1—ketoconazole drug interactions were assessed by a broth microdilution checkerboard assay as described in EUCAST document 7.1 (see, e.g., EUCAST definitive document EDef 7.1: method for the determination of broth dilution MICs of antifungal agents for fermentative yeasts. Clin Microbiol Infect. 2008; 14(4):398-405). Absorbance was assessed using a Molecular Devices V max Kinetic Microplate Reader at a wavelength of 540 nm. Combination indices were calculated as follows: $CI=(C_{IKIX1}/IC_{IKIX1})+(C_{AZ}/IC_{AZ})$; where $IC_{IKIX1}$ and $IC_{AZ}$ are concentrations of iKIX1 alone or ketoconazole alone, respectively, that result in greater than 50% inhibition of growth as compared to untreated control and iKIX1 and $C_{AZ}$ are the concentrations of iKIX1 and ketoconazole in combination that provide the same effect (greater than 50% inhibition of growth as compared to untreated control). A CI of less than 1 is taken to indicate synergy.

RNA-Seq Experiments

Cells were grown in YPD at 30° C. with shaking overnight (24 hours) then washed twice in 2× volume of Milli-Q water before being resuspended in YP to an $OD_{600}$ of 0.8. Cells were grown with shaking overnight (~16 hours) before splitting and treatment with vehicle (DMSO) or 10 µM iKIX1. Cells were grown with shaking another 8 hours before harvest of non-azole induced samples. Remaining cultures were induced to a final concentration of 40 µM ketoconazole and harvested after 15 minutes by centrifugation at 4,000 rpm for 4 minutes at 4° C. Media was aspirated and cells were snap frozen on dry ice. RNA isolation was performed as previously described (see, e.g., Martin R, Moran G P, Jacobsen I D, Heyken A, Domey J, Sullivan D J, et al. The *Candida albicans*-specific gene EED1 encodes a key regulator of hyphal extension. PLoS One.6(4):e18394. PMCID: 3075580); RNA was then DNase treated using recombinant DNaseI. RNase-free (Roche) according to manufacturer's instructions. Samples were prepared in triplicate and multiplexed RNA-Seq libraries were constructed using PolyA selection and the NEBNext Ultra Directional RNA Library Prep Kit for Illumina (New England Biolabs). Sequencing was carried out on Illumina HiSeq 2500, resulting in approximately 17.68 million of 50 bp paired-end reads per sample. STAR aligner was used to map sequencing reads to transcripts in the reference genomes (S288C for *Saccharomyces cerevisiae* and draft genome from isolate DSY562 for *Candida glabrata*) (see, e.g., Dobin A, Davis C A, Schlesinger F, Drenkow J, Zaleski C, Jha S, et al. STAR: ultrafast universal RNA-seq aligner. Bioinformatics.29(1): 15-21. PMCID: 3530905). Read counts for individual transcripts were produced with HTSeq-count, followed by the estimation of expression values and detection of differentially expressed transcripts using EdgeR (see, e.g., Anders S, Pyl P T, Huber W. HTSeq—a Python framework to work with high-throughput sequencing data. Bioinformatics.31 (2):166-9. PMCID: 4287950; Robinson M D, McCarthy D J, Smyth G K. edgeR: a Bioconductor package for differential expression analysis of digital gene expression data. Bioinformatics.26(1): 139-40. PMCID: 2796818). The data discussed in this publication have been deposited in NCBI's Gene Expression Omnibus and are accessible through GEO series accession number GSE74361 (see, e.g., Edgar R, Domrachev M, Lash A E. Gene Expression Omnibus: NCBI gene expression and hybridization array data repository. Nucleic Acids Res. 2002; 30(1):207-10. PMCID: 99122).

Efflux Assays

Cells were grown in YPD at 30° C. with shaking overnight (24 hours) then washed twice in 2× volume of Milli-Q water before being resuspended in YP to an $OD_{600}$ of 0.8. Cells were treated with vehicle or iKIX1 and grown with shaking for 16 hours. Equivalent numbers of cells (as assessed by $OD_{600}$=3) were concurrently induced with 5 µM of ketoconazole and loaded with 10 µM of rhodamine 6G for 30 minutes at 30° C. with shaking in the dark. Untreated cells were placed on ice and not treated with ketoconazole or rhodamine 6G. All cells were placed on ice and washed twice with cold YP containing either 5 µM ketoconazole+vehicle (DMSO) or 5 µM ketoconazole+30 µM iKIX1 to remove excess rhodamine 6G. Cells were resuspended in room temperature YP with either 5 µM ketoconazole+vehicle (DMSO) or 5 µM ketoconazole+30 µM iKIX1 and 100 µL was transferred to a 96-well plate. An Envision 2103 Multilabel plate reader was used to assess RFU (relative fluorescence units; excitation 485, emission 535) over 60 minutes at 7.5 minute intervals. Efflux rate was calculated as RFU per second with 7.5 minute windows. Experiments were performed in triplicate, with duplicate readings for each sample; error bars indicate s.d.

Transcription Assays and Quantitative Real-Time PCR

Cells were grown in YPD at 30° C. with shaking 24 hours then washed twice in 2× volume of Milli-Q water before being resuspended in YP to an $OD_{600}$ of 0.8. Cells were grown with shaking overnight (~16 hours) before splitting and treatment with vehicle (DMSO) or iKIX1 to concentrations indicated. Cells were grown with shaking another 8 hours before harvest of non-azole induced samples. Remaining cultures were induced to a final concentration of 40 µM ketoconazole and harvested after 15 minutes and subsequent time points, if shown. For harvest and preparation of RNA. cells equivalent to an $OD_{600}$ of 0.4 were centrifuged at 4,000 rpm for 4 minutes and then resuspended in 700 µL Trizol. Cells in Trizol were bead beat with 0.4 mL glass beads for 2×30 seconds and then protocol was followed according to manufacturer's instructions. One µg of RNA was used for DNase I treatment (Roche) and subsequent cDNA synthesis using Roche Transcriptor First Strand cDNA synthesis kit. cDNA was diluted 5× in water and 2.5 µL was used per reaction with Roche SYBR green. Quantitative real-time PCR reactions were run and analyzed on a Roche LightCycler 480 system. Sc transcripts were normalized to ScSCR1 and untreated, uninduced DMSO control; Cg transcripts were normalized to CgRDN25-1 and untreated, uninduced DMSO control.

Viability and Transcription Assays in Mammalian HepG2 Cells

HepG2 (ATCC HB-8065) cell viability was assessed using the CellTiter-Glo assay kit (Promega). HepG2 cells (N=4,500) were seeded in each well in 100 µL MEM+10% FBS in 96-well CellBIND (Corning) plates. After 24 hours, iKIX1 was added to final concentrations indicated for a final volume of 150 µL. HepG2 cells were incubated with iKIX1 for another 72 hours before CellTiter-Glo signal was assessed with an Envision 2103 Multilabel plate reader according to the manufacturer's instructions. HepG2 cells were not authenticated or tested for *mycoplasma* contamination following receipt from ATCC.

For transcription assays, HepG2 cells were seeded in MEM+10% FBS on 12-well poly-D-lysine-coated plates at a concentration of 175,000 cells per mL. After cells attached (4 hours), media was aspirated and iKIX1 was added in fresh MEM+10% FBS to final concentrations indicated. Cells were treated with iKIX1 for 24 hours before RNA was isolated using Trizol according to manufacturer's instructions. Quantitative real-time RT-PCR was carried out as described above.

Plasma Stability and Microsomal Stability Analysis

Microsome stability assays were performed as previously described (see, e.g., Choi J Y, Calvet C M, Gunatilleke S S, Ruiz C, Cameron M D, McKerrow J H, et al. Rational development of 4-aminopyridyl-based inhibitors targeting *Trypanosoma cruzi* CYP51 as anti-chagas agents. J Med Chem. 56(19):7651-68. PMCID: 3864028); for plasma stability, 100% freshly drawn plasma in LiHeparin was used with similar sampling and sample preparation with no addition of microsomes, buffer or NADPH.

In Vivo Pharmacokinetic Analysis of iKIX1

Male Swiss albino mice were dosed via tail vein (IV; intravenous, solution in 5% NMP and 10% solutol in saline, dose: 2 mg/kg) or via oral gavage (PO; suspensions in 0.5% w/v Na CMC with 0.1% v/v Tween-80 in water). Blood and brain samples were collected at 0, 0.083 (for IV only), 0.25, 0.5, 1, 2, 4, 6 (for PO only), 8, 12, and 24 hours for the IV and PO groups. The blood samples were collected from sets of three mice at each time point. Plasma samples were separated by centrifugation and stored below −70° C. until analysis. Brain samples were homogenized using ice-cold phosphate buffer saline (pH 7.4) and homogenates were stored below −70° C. until analysis. All samples were processed and analyzed by C/MS/MS (LLOQ, 2.03 ng/mL for plasma and 10.16 ng/mL for brain). Pharmacokinetic parameters were calculated using the noncompartmental analysis tool of Phoenix WinNonlin (version 5.3).

*Galleria mellonella* Survival Assays

*Galleria mellonella* larvae were injected with 5×10⁶ CFUs of PDR1 wild-type (SFY114, 10 larvae per group) or $PDR1^{L280F}$ (SFY115, 9 larvae per group) *Candida glabrata* and a single injection of PBS alone, iKIX1 alone (25 mg/kg), fluconazole alone (50 mg/kg) or a combination of fluconazole and iKIX1. Each larva was injected through the last right proleg with 40 µL of a cell suspension using a Myjector U-100 Insulin syringe (Terumo Europe). Compound solutions (40 µL) were injected through remaining prolegs one hour after infection. As controls, groups of non-infected larvae were injected with the combination of fluconazole and iKIX1, or not injected with compounds. Larvae were incubated in the dark at 30° C. and % survival was assessed every 24 hours.

Yeast Adherence to Epithelial Cells

Adherence to epithelial cells was tested as previously described (see, e.g., Vale-Silva L, Ischer F, Leibundgut-Landmann S, Sanglard D. Gain-of-function mutations in PDR1, a regulator of antifungal drug resistance in *Candida glabrata*, control adherence to host cells. Infect Immun. 81(5): 1709-20. PMCID: 3648025). Briefly, epithelial Chinese hamster ovary modified cell line Lec2 (CHO-Lec2; ATCC CRL1736) was cultured in high-glucose minimum essential medium (MEM, Life Technologies) with L-glutamine, supplemented with 100 U/mL penicillin, 100 µg/mL streptomycin (Life Technologies), and 10% FBS (Life Technologies). CHO-Lec2 cells were not authenticated or tested for *mycoplasma* contamination following receipt from ATCC. Log-phase epithelial cells were seeded in 24-well plates at a density of 1.0×10⁵ cells/well in 1 mL of culture medium and allowed to grow to full confluence at 37° C. in humid atmosphere with 5% $CO_2$, typically for 72 hours. To prepare *C. glabrata* suspensions for infection, overnight cultures of test strains were diluted in fresh medium containing 30 µM iKIX1 or the same volume of DMSO (vehicle controls) and grown for a minimum of two generations to mid-log phase. Ketoconazole was added to indicated samples for the last 15 minutes of incubation at a concentration of 40 µM. Log-phase yeast cultures were washed and resuspended in PBS. Epithelial cell monolayers were infected with 1:1 mixed yeast suspensions containing $3.0 \times 10^5$ yeast cells and the plates were centrifuged at 200×g for 1 minute. Co-cultures were incubated at 37° C. in humid atmosphere with 5% $CO_2$ for 30 minutes and nonadherent yeasts were removed by washing. Adherent yeasts were recovered by lysis of the epithelial cells in 0.1% Triton X-100 and plated onto YPD agar plates for quantification of CFUs. YPD agar alone and YPD agar plates containing 30 µg/mL of fluconazole were used to distinguish between azole-susceptible and azole-resistant yeast strains.

Mouse Urinary Tract Infection Model

Urinary tract infection (UTI) experiments were performed following a previously described model (see, e.g., Chen Y L, Konieczka J H, Springer D J, Bowen S E, Zhang J, Silao F G, et al. Convergent Evolution of Calcineurin Pathway Roles in Thermotolerance and Virulence in *Candida glabrata*. G3 (Bethesda).2(6):675-91. PMCID: 3362297). Briefly, for tissue burden experiments each *C. glabrata* strain was grown in 10 mL of YPD broth under agitation for 18 hours at 37° C. After growth, cells were centrifuged, washed and resuspended in 10 mL of sterile PBS, and then adjusted to reach a concentration of $5 \times 10^9$ *C. glabrata* $mL^{-1}$. For each strain, a group of 10 isoflurane-anaesthetized mice were infected via intra-urethral catheterization (polyethylene catheter, ~4 cm long; outer diameter, 0.61 mm; Becton Dickinson. Sparks. Md., USA) using 100 µL of the corresponding *C. glabrata* cell suspension for each animal. Mice were sacrificed 7 days after the transurethral challenge, and, for each animal, bladders and kidney pairs were harvested, weighed and homogenized in 1 and 5 mL of sterile saline, respectively. *C. glabrata* inocula and burdens were enumerated by performing serial dilutions and counting CFUs on YPD agar. The *C. glabrata* detection limits were 50 and 10 CFU $mL^{-1}$ for kidneys and bladder homogenates, respectively. For all experimental groups, counts of CFU were analysed by unpaired I-test, and a P-value of less than 0.05 was considered to be significant. For treatment experiments the same procedure was used but animals were inoculated intraperitoneally with fluconazole (100 mg/kg/day) and/or iKIX1 (100 mg/kg/day).

Mouse Disseminated Fungal Burden Model

Experiments were carried out as previously described (27). Unless otherwise indicated, mice were injected with 100 mg/kg/day iKIX1. Low fluconazole concentration was 25 mg/kg/day and high fluconazole concentration was 100 mg/kg/day. Low iKIX1 treatment was 10 mg/kg/day.

Mouse Studies

Female BALB/c mice (20 to 25 g) purchased from Harlan Italy S.r.l (San Pietro al Natisone, Udine, Italy) and inbred in-house were used for mouse studies. The animal experiments were performed under a protocol approved by the Institutional Animal Use and Care Committee at Università Cattolica del S. Cuore, Rome, Italy (Permit number: 721, Feb. 10, 2013) and authorized by the Italian Ministry of Health, according to Legislative Decree 116/92, which implemented the European Directive 86/609/EEC on laboratory animal protection in Italy. Veterinarians of the Service for Animal Welfare routinely checked animal welfare. Statistical differences were measured using a Wilcoxon Mann-Whitney test and P<0.05 was considered statistically significant.

Statistics

Unless otherwise indicated, in vitro experiments were carried out with at least three biological replicates and graphs represent mean+/−s.d. Unless otherwise indicated, statistical differences were measured using an unpaired, two-tailed Student's t-test. P<0.05 was considered as statistically significant. The number of animals used in this study was calculated hypothesizing a prevalence of infection of 99% and a precision of 0.005, using the formula n=t2P1−PD2, where n is the numerosity of the sample, t the distribution, P the prevalence and D the precision. Animals were excluded from analysis if one of the following humane endpoint was reached: body weight (decrease of more than 20% at baseline), body temperature (hypothermia extremely important), matted hair (still expected in the systemic model), posture and behavior (eg. lethargy). After infection with *C. glabrata* strains the animals were randomized in the control and the different treatment groups. Tissue burden evaluation was carried out in a blinded manner, the researcher who performed the tissue burden evaluation did not know if the analyzed organs were from treated or control mouse groups.

SYNTHESIS OF COMPOUNDS

Synthesis of Compound iKIX1

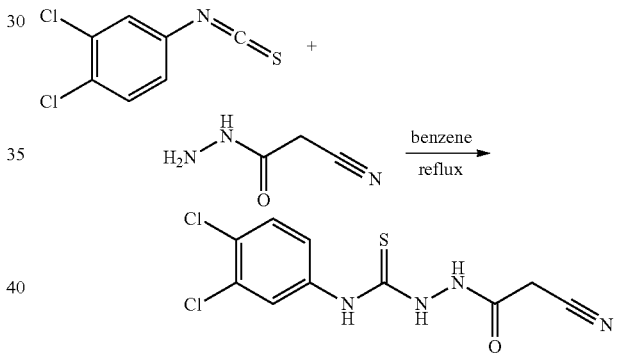

5.00 g (24.4 mmol) 3,4-dichlorophenyl isothiocyanate (Oakwood Chemical) and 2.42 g (24.4 mmol) cyanoacetohydrazide (Acros) were suspended in 50 ml benzene and the reaction mixture was heated with stirring to reflux for 12 hours. The solvent was filtered off and the solid product was recrystallized twice from methanol to yield 2.55 g (8.42 mmol, 35% yield) of white fluffy crystals. ESI-MS m/z 302.93 (M+H); 1H-NMR (400 MHz, dmso) δ 10.37 (s, 1H), 9.97 (s, 1H), 9.79 (br, 1H), 7.88 (br, 0.3H), 7.77 (br, 0.7H), 7.60 (d, 1H, J=8.7 Hz), 7.46 (dd, 1H, J=8.7 Hz. J=2.5 Hz), 3.72 (s, 2H); 13C-NMR (100 MHz, dmso) δ 178.6, 164.1, 152.1, 151.6, 150.5, 150.0, 144.4, 139.5, 130.4, 116.1.

Synthesis of SB1-A-01

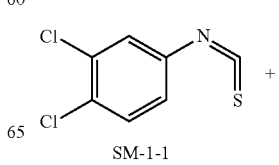

SM-1-1

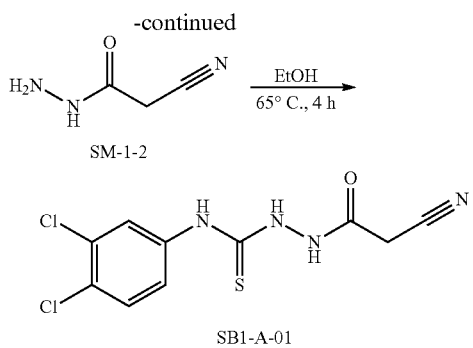

2-(2-Cyanoacetyl)-N-(3,4-dichlorophenyl)hydrazinecarbothioamide (SB1-A-01)

The mixture of SM-1-1 (200 mg, 0.98 mmol) and SM-1-2 (200 mg, 2.02 mmol) in EtOH (15 mL) was stirred at 65° C. for 4 h, then concentrated to remove the solvent. The residue was purified by prep-HPLC (C18 column, CH$_3$CN/H$_2$O. containing 0.05% TFA) to obtain the SB1-A-01 (white solid, 100 mg, yield: 34%). HPLC: 100% (254 nm); LCMS (m/z): 303 [M+H]$^+$; $^1$H NMR (DMSO-d$_6$, 400 MHz): δ 10.40 (s, 1H), 10.00 (s, 1H), 9.90-9.70 (br s, 1H), 7.79 (s, 1H), 7.62 (d, J=8.4 Hz, 1H), 7.47 (dd, J$_1$=8.4 Hz, J$_2$=2.4 Hz, 1H), 3.74 (s, 2H) ppm.

Synthesis of SB1-A-03

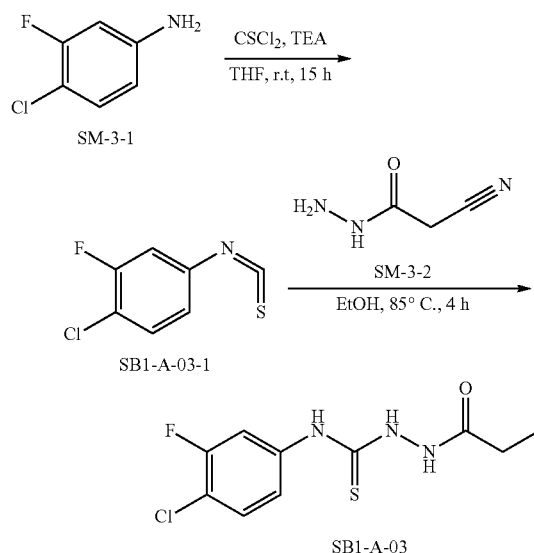

1-Chloro-2-fluoro-4-isothiocyanatobenzene (SB1-A-03-1)

To a solution of SM-3-1 (300 mg, 2.06 mmol), TEA (2 mL) in THF (20 mL) was added CSCl$_2$ (0.3 mL, 3.91 mmol) dropwise, then stirred at r.t overnight. After completion, the mixture was concentrated, the residue was dissolved in ethyl acetate (100 mL), and washed with brine (50 mL×2). The organic layer was dried with Na$_2$SO$_4$, filtered, concentrated to obtain brown sticky oil SB-A-03-1 (330 mg, yield: 85%), which was used directly without further purification.

N-(4-Chloro-3-fluorophenyl)-2-(2-cyanoacetyl)hydrazinecarbothoamide (SB1-A-03)

The mixture of SB1-A-03-1 (330 mg, 1.76 mmol). SM-3-2 (180 mg, 1.82 mmol) in EtOH (20 mL) was stirred at 85° C. for 4 h. then concentrated to removed the solvent. The residue was purified by prep-HPLC (C18 column, CH$_3$CN/H$_2$O, containing 0.05% TFA) to obtain SB1-A-03 (white solid 180 mg, yield: 36%). HPLC: 100% (254 nm); LCMS (m/z): 287 [M+H]+; $^1$H NMR (DMSO-d$_6$, 400 MHz): δ 10.39 (s, 1H), 9.98 (s, 1H), 9.86 (br s, 1H), 7.68 (d, J=9.6 Hz, 1H), 7.57 (t, J=8.8 Hz, 1H), 7.29 (dd, J$_1$=8.8 Hz, J$_2$=1.6 Hz, 1H), 3.76 (s, 2H) ppm.

Synthesis of SB1-A-07

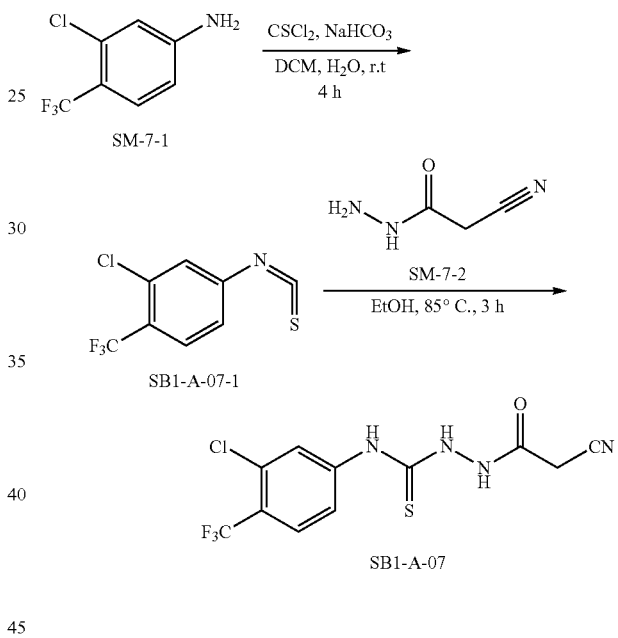

N-(3-Chloro-4-(trifluoromethyl)phenyl)-2-(2-cyanoacetyl) hydrazinecarbothioamide (SB1-A-07)

The mixture of SB1-A-07-1 (396 mg, 1.67 mmol), SM-7-2 (166 mg, 1.67 mmol) in EtOH (20 mL) was stirred at 85° C. for 3 h, then concentrated to remove the solvent. The residue was purified by prep-HPLC (C18 column, CH$_3$CN/H$_2$O, containing 0.05% TFA) to obtain SB1-A-07 (white solid, 170 mg, yield: 30%). HPLC: 96.17% (254 nm); LCMS (m/z): 333 [M+H]$^+$; $^1$H NMR (DMSO-d$_6$, 400 MHz): δ 10.45 (bs, 1H), 10.17 (s, 1H), 9.91 (br s, 1H), 8.00 (s, 1H), 7.85 (d, J=8.4 Hz, 1H), 7.73 (d, J=8.8 Hz, 1H), 3.76 (s, 2H) ppm.

2-Chloro-4-isothiocyanato-1-(trifluoromethyl)benzene (SB1-A-07-1)

To a solution of SM-7-1 (340 mg, 1.74 mmol). NaHCO$_3$ (438 mg, 5.21 mmol). H$_2$O (5 mL) and DCM (20 mL) was added CSCl$_2$ (0.20 mL, 2.63 mmol) dropwise at 0° C., then the mixture was stirred for 4 h. after completion, the reaction mixture was diluted with DCM (200 mL), and washed with brine (50 mL), the organic phase was dried with $Na_2SO_4$, filtered, and concentrated to remove the solvent to obtain SB1-A-07-1 (light brown solid, 400 mg, yield: 97%).

Synthesis of SB1-A-18

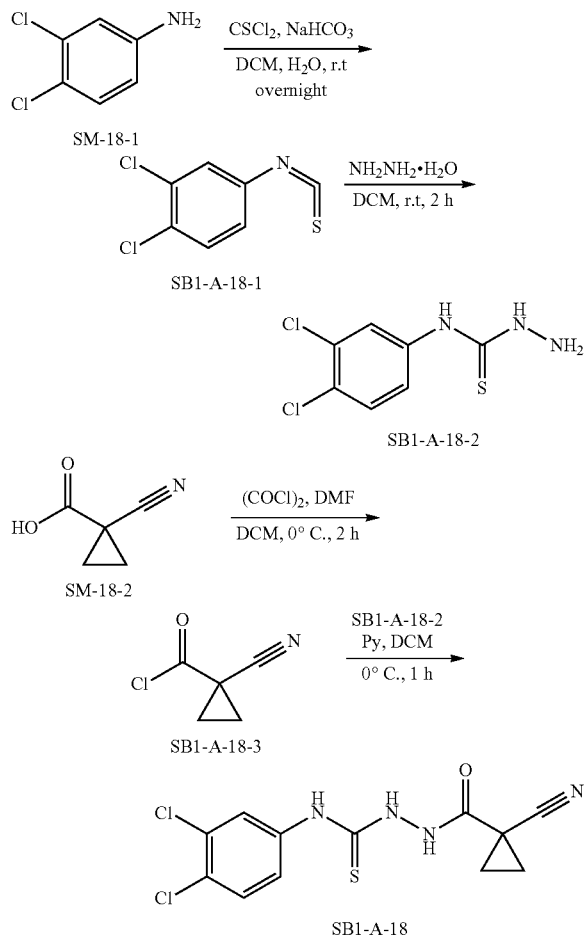

1,2-Dichloro-4-isothlocyanatobenzene (SB1-A-18-1)

To a solution of 3,4-dichloroaniline (300 mg, 1.86 mmol) and $NaHCO_3$ (781 mg, 9.3 mmol) in $H_2O$ (10 mL) and DCM (20 mL) was added thiophosgene (424 mg, 3.73 mmol) at 0° C., the mixture was stirred overnight. After completion, the reaction mixture was extracted with DCM (50 mL), and washed with water, the organic phase was concentrated under reduced pressure to obtain SB1-A-18-1 (300 mg crude product) used for the next step directly.

N-(3,4-Dichlorophenyl)hydrazinecarbothioamide (SB1-A-18-2)

The mixture of 1,2-dichloro-4-isothiocyanatobenzene (200 mg, 0.985 mmol) and $NH_2NH_2$—$H_2O$ (60%) (63 mg, 1.18 mmol) in DCM (10 mL) was stirred at r.t for 2 h, after completion, the reaction mixture was concentrated under reduced pressure to obtain SB1-A-18-2 (231 mg, 100%) which was used for the next step directly. LCMS (m/z): 236.0 $(M+H)^-$.

1-Cyanocyclopropanecarbonyl Chloride (SB1-A-18-3)

To a solution of 1-cyanocyclopropanecarboxylic acid (80 mg, 0.72 mmol) and oxalyl dichloride (136 mg, 1.08 mmol) in DCM (5 mL) was added a drop of DMF at 0° C., then the mixture was stirred for 2 h. after completion the reaction mixture solution was used for next step directly.

2-(1-Cyanocyclopropanecarbonyl)-N-(3,4-dichlorophenyl)hydrazinecarbothioamide (SB1-A-18)

To a solution of N-(3,4-dichlorophenyl)hydrazinecarbothioamide (150 mg, 0.63 mmol) and pyridine (249 mg, 3.15 mmol) in DCM (10 mL) was added the above solution of 1-cyanocyclopropanecarbonyl chloride (4 mL) at 0° C., then the mixture was stirred for 1 h. then concentrated under reduced pressure to remove the solvent, the residue was purified by prep-HPLC (C18 column, $CH_3CN/H_2O$, containing 0.05% TFA) to obtain SB1-A-18 (white solid, 7 mg, yield: 4%). HPLC: 100% (254 nm); LCMS (m/z): 329.0 $[M+H]^*$; $^1H$ NMR (DMSO-$d_6$ 400 MHz): δ 10.34 (s, 1H), 9.87 (s, 1H), 7.78 (s, 1H), 7.61 (d, J=9.2 Hz, 1H), 7.47-7.50 (m, 1H), 1.59-1.70 (m, 4H) ppm.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given. endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

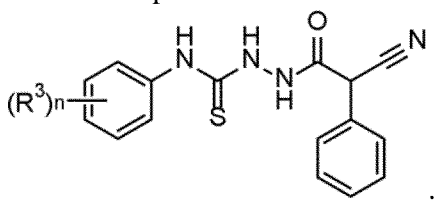

What is claimed is:

1. A compound of Formula (II):

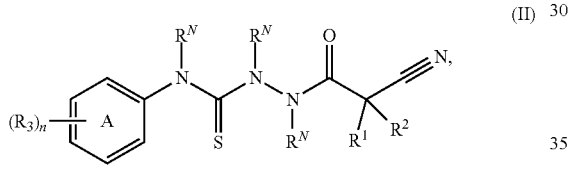

or a pharmaceutically acceptable salt thereof, wherein:
$R^1$ and $R^2$ are independently hydrogen, substituted alkyl, unsubstituted $C_{2-6}$ alkyl, optionally substituted alkenyl, optionally substituted alkynyl, optionally substituted aryl, optionally substituted carbocyclyl, optionally substituted heterocyclyl, or optionally substituted heteroaryl; or optionally $R^1$ and $R^2$ are joined together with the intervening atoms to form optionally substituted carbocyclyl or optionally substituted heterocyclyl;
provided that at least one of $R^1$ and $R^2$ is not hydrogen;
each instance of $R^N$ is independently hydrogen, optionally substituted alkyl, optionally substituted acyl, or a nitrogen protecting group;
each instance of $R^3$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —OR$^{3a}$, —N(R$^{3b}$)$_2$, or —SR$^{3c}$; or optionally two $R^3$ are joined together with the intervening atoms to form optionally substituted carbocyclyl or optionally substituted heterocyclyl;
provided that at least one instance of $R^3$ is selected from the group consisting of halogen, optionally substituted acyl, optionally substituted sulfinyl, optionally substituted sulfonyl, and haloalkyl;
each instance of $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;
each instance of $R^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;
each instance of $R^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and
n is 1, 2, 3, 4, or 5.

2. A compound of Formula (III):

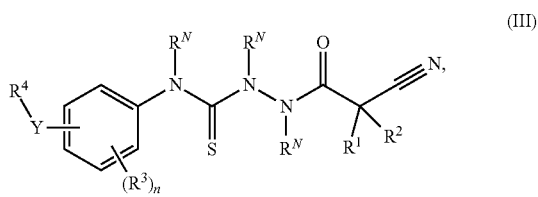

or a pharmaceutically acceptable salt thereof, wherein:
Y is a bond, optionally substituted alkylene, —O—, —NR$^N$—, or —S—;
$R^1$ and $R^2$ are independently hydrogen, optionally substituted alkyl, optionally substituted alkenyl, optionally substituted alkynyl, optionally substituted aryl, optionally substituted carbocyclyl, optionally substituted heterocyclyl, or optionally substituted heteroaryl; or optionally $R^1$ and $R^2$ are joined together with the intervening atoms to form optionally substituted carbocyclyl or optionally substituted heterocyclyl;

each instance of $R^N$ is independently hydrogen, optionally substituted alkyl, optionally substituted acyl, or a nitrogen protecting group;

each instance of $R^3$ is independently hydrogen, halogen, —CN, —SCN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfinyl, optionally substituted sulfonyl, —$OR^{3a}$, —$N(R^{3b})_2$, or —$SR^{3c}$; or optionally two $R^3$ are joined together with the intervening atoms to form optionally substituted carbocyclyl or optionally substituted heterocyclyl;

each instance of $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{3c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

$R^4$ is optionally substituted carbocyclyl, optionally substituted heterocyclyl, optionally substituted aryl, or optionally substituted heteroaryl; and n is 1, 2, 3, or 4.

3. The compound of claim 1, wherein $R^1$ and $R^2$ are joined together with the intervening atoms to form optionally substituted carbocyclyl or optionally substituted heterocyclyl.

4. The compound of claim 1, wherein at least one of $R^1$ and $R^2$ is halogen.

5. The compound of claim 1, wherein one of $R^1$ or $R^2$ is optionally substituted phenyl.

6. The compound of claim 1, wherein each instance of $R^N$ is hydrogen.

7. The compound of claim 1, wherein at least one instance of $R^3$ is selected from the group consisting of halogen, and haloalkyl.

8. The compound of claim 1, wherein Ring A is of one of the following formulae:

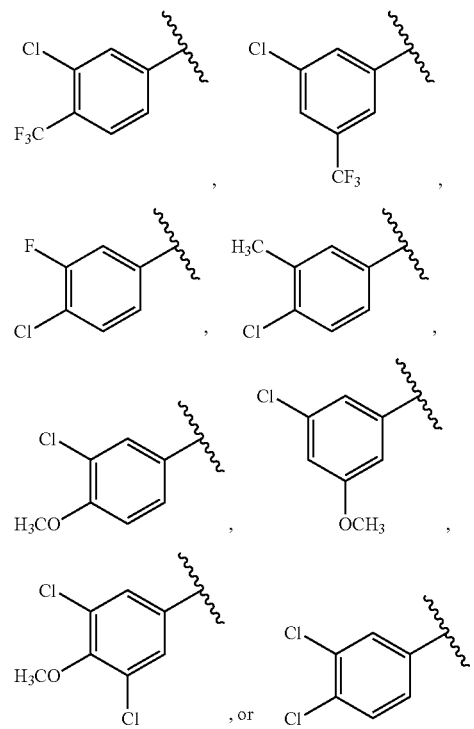

9. The compound of claim 1, wherein the compound is of Formula (II-a):

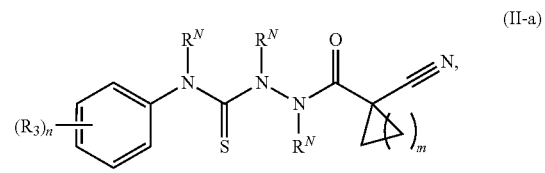

or a pharmaceutically acceptable salt thereof, wherein:

m is 1, 2, 3, or 4.

10. The compound of claim 1, wherein the compound is of one of the following formulae:

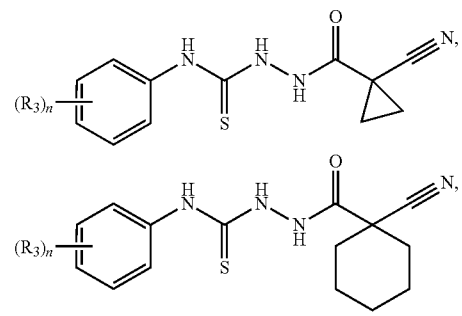

or a pharmaceutically acceptable salt thereof.

11. The compound of claim 1, wherein the compound is of one of the following formulae:

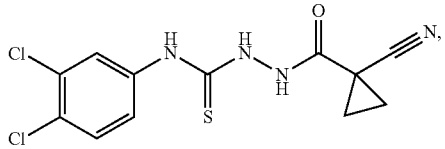

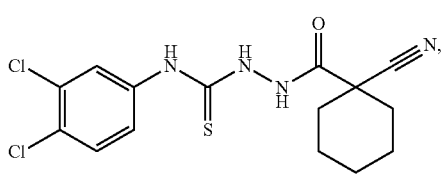

or a pharmaceutically acceptable salt thereof.

12. The compound of claim 1, wherein the compound is of the following formula:

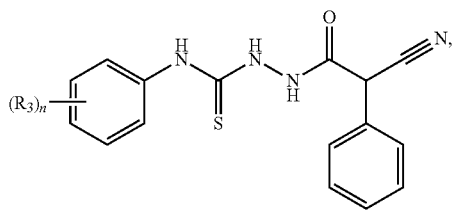

or a pharmaceutically acceptable salt thereof.

13. The compound of claim 1, wherein the compound is of the following formula:

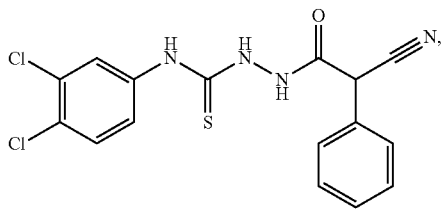 [SMILES: N#CC(C(=O)NNC(=S)Nc1ccc(Cl)c(Cl)c1)c1ccccc1]

or a pharmaceutically acceptable salt thereof.

14. The compound of claim 2, wherein the compound is of the following formula:

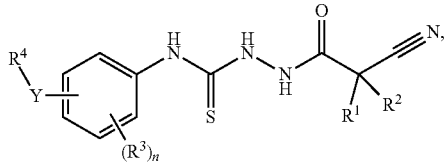

or a pharmaceutically acceptable salt thereof.

15. The compound of claim 2, wherein the compound is of one of the following formulae:

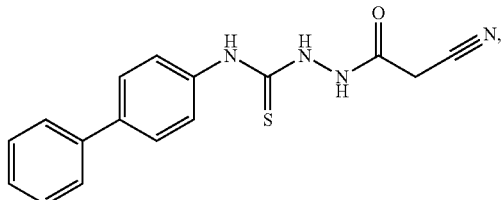

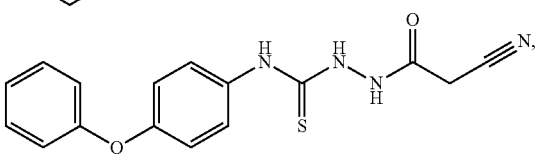

or pharmaceutically acceptable salt thereof.

16. A compound selected from the group consisting of:

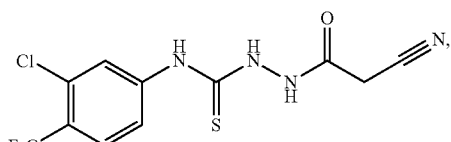

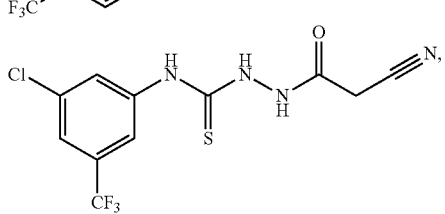

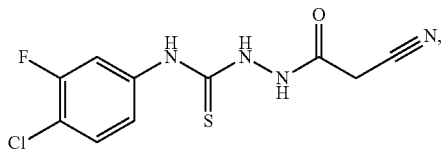

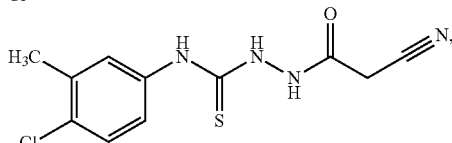

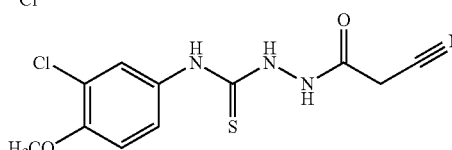

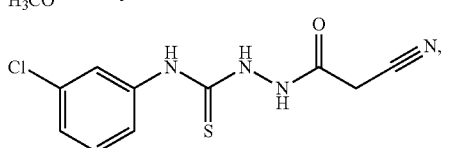

and pharmaceutically acceptable salts thereof.

17. A pharmaceutical composition comprising a compound of claim 1, and a pharmaceutically acceptable excipient.

18. A method for treating a fungal infection in a subject, the method comprising administering to the subject a therapeutically effective amount of a compound of claim 1, or a pharmaceutically acceptable salt thereof.

19. A method of killing a fungus or inhibiting the growth of a fungus, the method comprising contacting the fungus with an effective amount of a compound of claim 1, or a pharmaceutically acceptable salt thereof.

20. The compound of claim 1, wherein at least one instance of $R^3$ is halogen.

21. The compound of claim 1, wherein n is 2; and each instance of $R^3$ is halogen.

22. The compound of claim 1, wherein n is 2; and each instance of $R^3$ is —Cl.

23. The compound of claim 1, wherein the compound is of one of the following formulae:

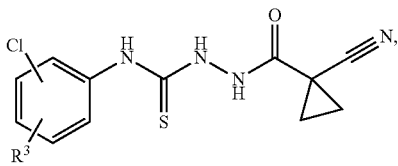

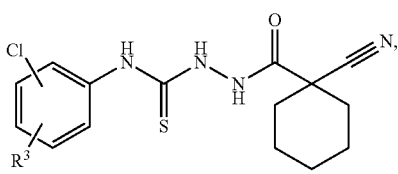

or a pharmaceutically acceptable salt thereof.

24. The compound of claim 1, wherein the compound is of one of the following formulae:

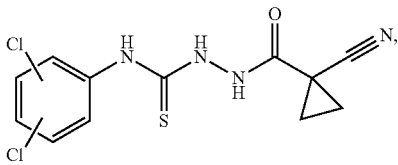

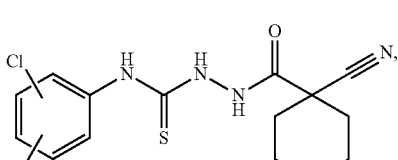

or a pharmaceutically acceptable salt thereof.

25. The compound of claim 1, wherein the compound is of Formula (I-a):

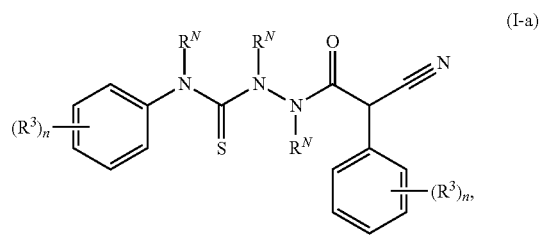

(I-a)

or a pharmaceutically acceptable salt thereof.

26. The compound of claim 1, wherein the compound is of the following formula:

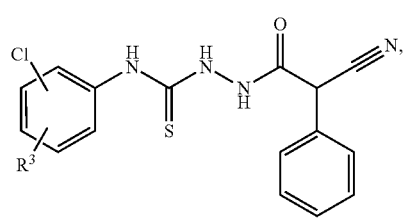

or a pharmaceutically acceptable salt thereof.

27. The compound of claim 1, wherein the compound is of the following formula:

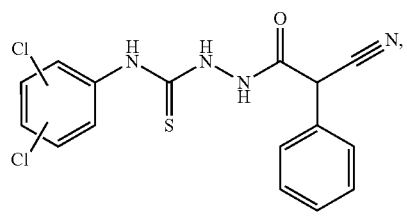

or a pharmaceutically acceptable salt thereof.

28. The compound of claim 2, wherein $R^1$ and $R^2$ are hydrogen.

29. The compound of claim 2, wherein Y is a bond or —O—.

30. The compound of claim 2, wherein $R^4$ is optionally substituted phenyl.

31. The compound of claim 2, wherein Y is a bond or —O—; and $R^4$ is optionally substituted phenyl.

32. The compound of claim 2, wherein each instance of $R^3$ is hydrogen.

33. The compound of claim 2, wherein the compound is of one of the following formulae:

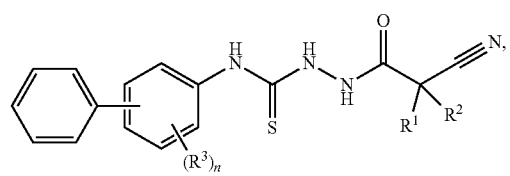

-continued

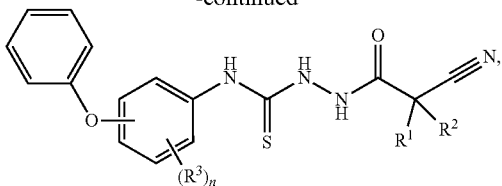

or a pharmaceutically acceptable salt thereof.

34. The compound of claim 2, wherein the compound is of one of the following formulae:

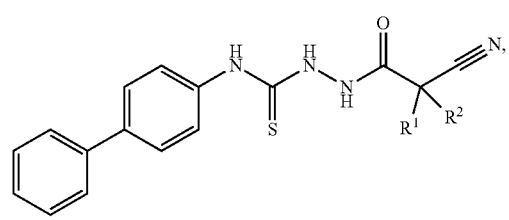

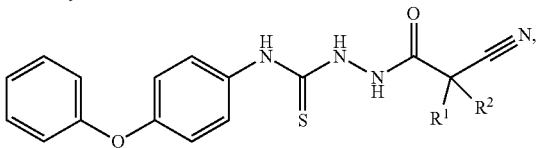

or a pharmaceutically acceptable salt thereof.

35. A pharmaceutical composition comprising a compound of claim 2, and a pharmaceutically acceptable excipient.

36. A pharmaceutical composition comprising a compound of claim 16, and a pharmaceutically acceptable excipient.

37. The compound of claim 1, wherein at least one instance of $R^3$ is —Cl.

38. The compound of claim 1, wherein $R^1$ and $R^2$ are independently hydrogen, substituted alkyl, optionally substituted alkenyl, optionally substituted alkynyl, optionally substituted aryl, optionally substituted carbocyclyl, optionally substituted heterocyclyl, or optionally substituted heteroaryl; or optionally $R^1$ and $R^2$ are joined together with the intervening atoms to form optionally substituted carbocyclyl or optionally substituted heterocyclyl.

39. The compound of claim 1, wherein $R^1$ and $R^2$ are independently hydrogen, optionally substituted alkenyl, optionally substituted alkynyl, optionally substituted aryl, optionally substituted carbocyclyl, optionally substituted heterocyclyl, or optionally substituted heteroaryl; or optionally $R^1$ and $R^2$ are joined together with the intervening atoms to form optionally substituted carbocyclyl or optionally substituted heterocyclyl.

* * * * *

UNITED STATES PATENT AND TRADEMARK OFFICE
CERTIFICATE OF CORRECTION

PATENT NO. : 11,136,291 B2
APPLICATION NO. : 15/998620
DATED : October 5, 2021
INVENTOR(S) : Sara Jean Buhrlage et al.

Page 1 of 2

It is certified that error appears in the above-identified patent and that said Letters Patent is hereby corrected as shown below:

In the Claims

In Claim 1, at Column 95, Lines 28-37, the formula:

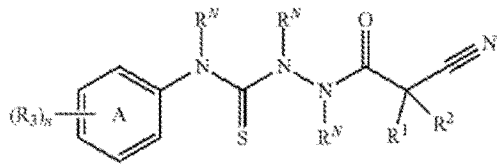

Should be replaced with the formula:

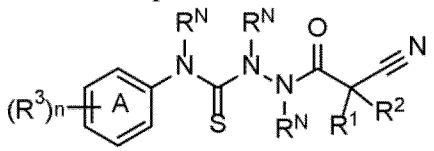

In Claim 9, at Column 98, Lines 37-47, the formula:

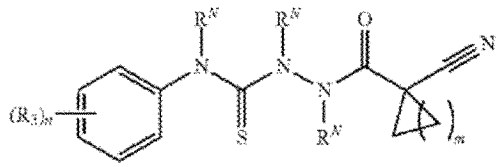

Should be replaced with the formula:

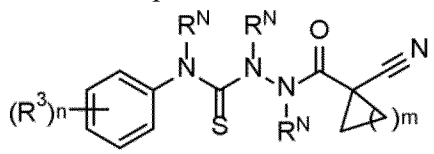

Signed and Sealed this
Fifth Day of July, 2022

Katherine Kelly Vidal
Katherine Kelly Vidal
*Director of the United States Patent and Trademark Office*

CERTIFICATE OF CORRECTION (continued)
U.S. Pat. No. 11,136,291 B2

In Claim 10, at Column 98, Lines 52-57, the first formula:

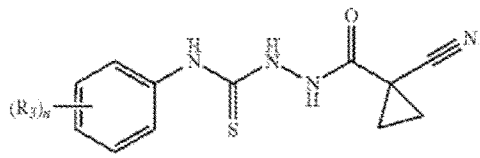

Should be replaced with the formula:

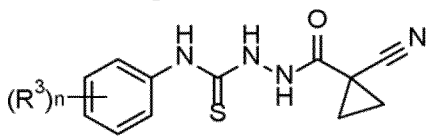

In Claim 10, at Column 98, Lines 60-65, the second formula:

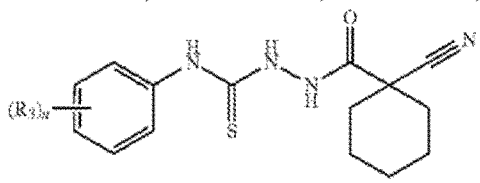

Should be replaced with the formula:

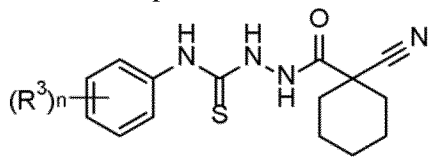

In Claim 12, at Column 99, Lines 25-36, the formula:

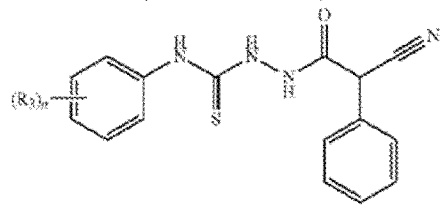

Should be replaced with the formula: